(12) United States Patent
Chiou et al.

(10) Patent No.: US 8,183,297 B2
(45) Date of Patent: May 22, 2012

(54) MEDIUM AND DEVICE FOR PROLIFERATION OF STEM CELLS AND TREATMENT OF CANCER-RELATED STEM CELL WITH RESVERATROL

(75) Inventors: Shih-Hwa Chiou, Taipei (TW); Tsung-Yun Liu, Taipei (TW); Tung-Hu Tsai, Taipei (TW); Jeng-Fan Lo, Taipei (TW); Yi-Ping Yang, Taiwan Country (TW); Fu-Ting Tsai, Taipei (TW); Yu-Chih Chen, Taipei (TW); Chian-Shiu Chien, Taipei (TW)

(73) Assignee: Taipei Veterans General Hospital, Taipei (TW)

( * ) Notice: Subject to any disclaimer, the term of this patent is extended or adjusted under 35 U.S.C. 154(b) by 146 days.

(21) Appl. No.: 12/501,279

(22) Filed: Jul. 10, 2009

(65) Prior Publication Data

US 2010/0010099 A1 Jan. 14, 2010

(30) Foreign Application Priority Data

Jul. 11, 2008 (TW) ................................. 97212434 U
Aug. 27, 2008 (TW) ................................. 97132616 A

(51) Int. Cl.
*A61K 31/05* (2006.01)
*C12N 5/02* (2006.01)
*C12M 1/12* (2006.01)
*A61P 35/00* (2006.01)

(52) U.S. Cl. ..................... 514/733; 435/297.1; 435/404; 435/377

(58) Field of Classification Search ......................... None
See application file for complete search history.

(56) References Cited

U.S. PATENT DOCUMENTS

| 6,008,260 A | 12/1999 | Pezzuto et al. |
| 7,455,860 B2 | 11/2008 | Gokaraju et al. |
| 2006/0257401 A1* | 11/2006 | Stassi et al. ................ 424/144.1 |

OTHER PUBLICATIONS

Kimura et al (J. Nutr. 2001; 131: 1844-1849).*
Zoberi et al. (Cancer Letters. 2002; 175: 165-173).*
Ahlin et al. (Drug Metabolism and Disposition. 2009; 37(12): 2275-2283).*
Garg et al. (Antioxidants and Redox Signaling. 2005; 7(11 & 12): 1630-1647).*
Kerr et al. (Letters in Drug Design & Discovery. Nov. 2006; 3(9): 607-621).*
Kaplan et al. (Nature. Dec. 8, 2005; 438: 820-827).*
Kelly et al. (PLoS ONE. Apr. 2010; 5(4): e10035, 1-18).*
Wang et al (Neuroscience Letters. 2003; 351: 83-86).*
Chiou et al. (PLoS ONE. May 7, 2008; 3(5): e2090, 1-13).*
Aggarwal et al (Anticancer Research. 2004; 24: 2783-2840).*
D. E. Bergsagel et al., Growth Characteristics of a Mouse Plasma Cell Tumor, Cancer Research 28, 2187-2196, Nov. 1968.
Gloria H. Heppner, Tumor Heterogeneity, Perspectives in Cancer Research, Cancer Research 44, 2259-2265, Jun. 1984.
Muhammad Al-Hajj et al., Prospective identification of tumorigenic breast cancer cells, PNAS, Apr. 1, 2003, vol. 100 No. 7, pp. 3983-3988.
Catherine A. O'Brien et al., A human colon cancer cell capable of initiating tumour growth in immunodeficient mice, vol. 445, Jan. 4, 2007, pp. 106-110.
Gavin D. Richardson et al., CD133, a novel marker for human prostatic epithelial stem cells, Journal of Cell Science, Mar. 15, 2204, vol. 117, pp. 3539-3545.
Gerald G. Wulf et al., A Leukemia stem cell with intrinsic drug efflux capacity in acute myeloid leukemia, Blood, 2001, vol. 98, pp. 1166-1173.
Ian Chambers et al., Functional Expression Cloning of Nanog, a Pluripotency Sustaining Factor in Embryonic Stem Cells, Cell, vol. 113, pp. 643-655, May 30, 2003.
Kaoru Mitsui et al., The Homeoprotein Nanog Is Required for Maintenance of Pluripotency in Mouse Epiblast and ES Cells, Cell, vol. 113, pp. 631-642, May 30, 2003.
Hans R. Scholer, Octamania: The POU factors in murine development, TIG, Oct. 1991, vol. 7 No. 10, pp. 323-329.
Maurizio Pesce et al., Oct. 4: Gatekeeper in the Beginnings of Mammalian Development, Stem Cells 2001, vol. 19, pp. 271-278.
Sheila K. Singh et al., Identification of a Cancer Stem Cell in Human Brain Tumors, Cancer Research 63, pp. 5821-5828, Sep. 15, 2003.
Atsushi Yanaihara et al., Cell Proliferation effect of lactoferrin in human endometrial stroma cell, Molecular Human Reproduction, vol. 6 No. 5, pp. 469-473, 2000.
Andrew Grey et al., The Low-Density Lipoprotein Receptor-Related Protein 1 Is a Mitogenic Receptor for Lactoferrin in Osteoblastic Cells, Molecular Endocrinology, vol. 18 No. 9, pp. 2268-2278, 2004.
Phedias Diamandis et al., Chemical genetics reveals a complex functional ground state of neural stem cells, Nature Chemical Biology, vol. 3 No. 5, May 2007, pp. 268-273.
Masami Harimoto et al., Novel approach for achieving double-layered cell sheets co-culture: overlaying endothelial cell sheets onto monolayer hepatocytes utilizing temperature-responsive culture dishes, J Biomed Mater Res vol. 62, pp. 464-470, 2002.
Ging-Ho Hsiue et al., A Novel Strategy for Corneal Endothelial Reconstruction with a Bioengineered Cell Sheet, Transplantation, 2006, vol. 81, pp. 473-476.
Charlie Schmidt, Drug makers chase cancer stem cells, vol. 26 No. 4, Apr. 2008, Nature Biotechnology.
Haojian Zhang et al., Mechanisms That Mediate Stem Cell Self-Renewal and Differentiation, J. Cell. Biochem., vol. 103, pp. 709-718, 2008.
Silvia Bradamanet et al., Cardiovascular Protective Effects of Resveratrol Cardiovascular Drug Reviews, vol. 22, No. 3, pp. 169-188.

(Continued)

*Primary Examiner* — Scott Long
(74) *Attorney, Agent, or Firm* — WPAT, P.C.; Anthony King

(57) ABSTRACT

The invention relates to a device for selecting stem cells with a serum free medium for amplification of stem cells. The invention also relates to a method of treating or preventing diseases caused by cancer-related stem cells. The invention further provides a method of enhancing radiosensitivity of cancer-related stem cells comprising radiotherapy with resveratrol, and the cancer-related stem cell has stronger drug resistance. The present invention further provides that resveratrol promotes differentiation and inhibits teratoma/tumor formation in induced pluripotent stem cells (iPS) and embryonic stem cells.

5 Claims, 38 Drawing Sheets
(5 of 38 Drawing Sheet(s) Filed in Color)

OTHER PUBLICATIONS

Mary Jo Atten et al., Resveratrol regulates cellular PKC $\alpha$ and $\delta$ to inhibit growth and induce apoptosis in gastric cancer cells, Investigational New Drugs 23: 111-119, 2005.

Po-Lin Kuo et al., Resveratrol-induced apoptosis is mediated by p53-dependent pathway in Hep G2 cells, Life Sciences, vol. 72, 2002, pp. 23-34.

Aldo M. Roccaro et al., Resveratrol Exerts Antiproliferative Activity and Induces Apoptosis in Waldenstrom's Macroglobulinemia, Clin Cancer Res, 2008, vol. 14 No. 6, Mar. 15, 2008, pp. 1849-1858.

Geoffrey E. Johnson et al., Radiosensitization of melanoma cells through combined inhibition of protein regulators of cell survival, Apoptosis, 2008, vol. 13, pp. 790-802.

Shih-Hwa Chiou et al., Identification of CD133-Positive Radioresistant Cells in Atypical Teratoid/ Rahbdoid Tumor, PLoS One, May 2008, pp. 1-13, vol. 3, Issue 5.

Chung-Lan Kao et al., Reservatrol-Induced Apoptosis and Increased Radiosensitivity in CD133-Positive Cells Derived from Atypical Teratoid/Rhabdoid Tumor, Int. J. Radiation Oncology Biol. Phys., 2009, pp. 219-228, vol. 74, No. 1.

\* cited by examiner

FIGURE

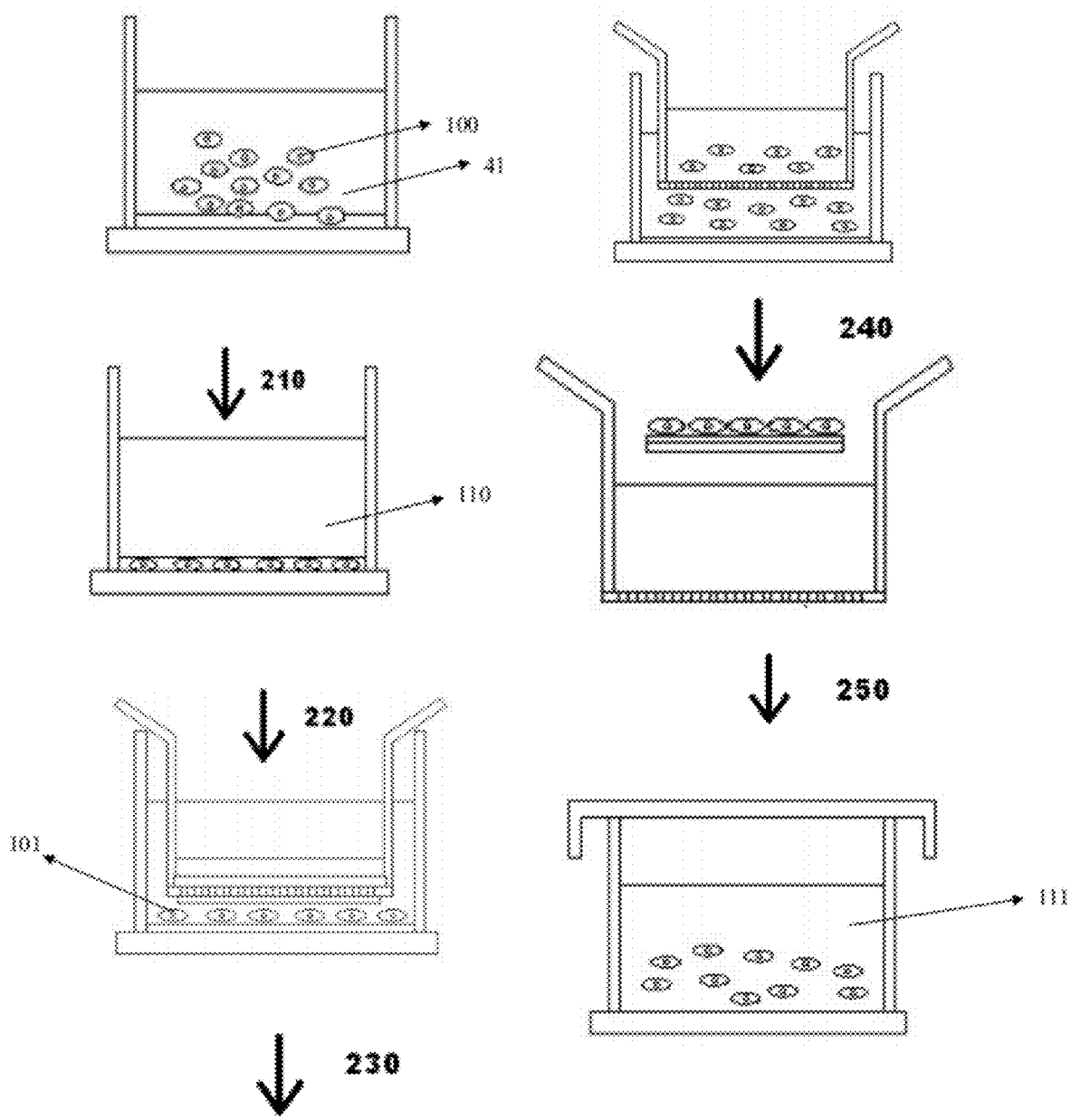

●    $1\times10^4$ dq
○    $1\times10^5$ dr
▼    $5\times10^5$ dq+dr

Fig. 21A
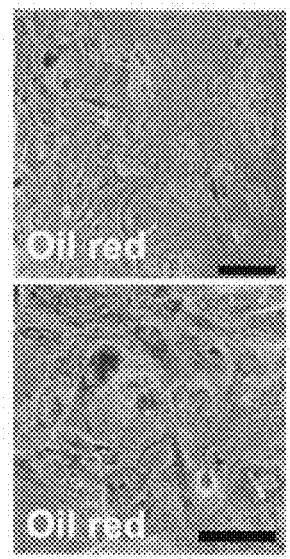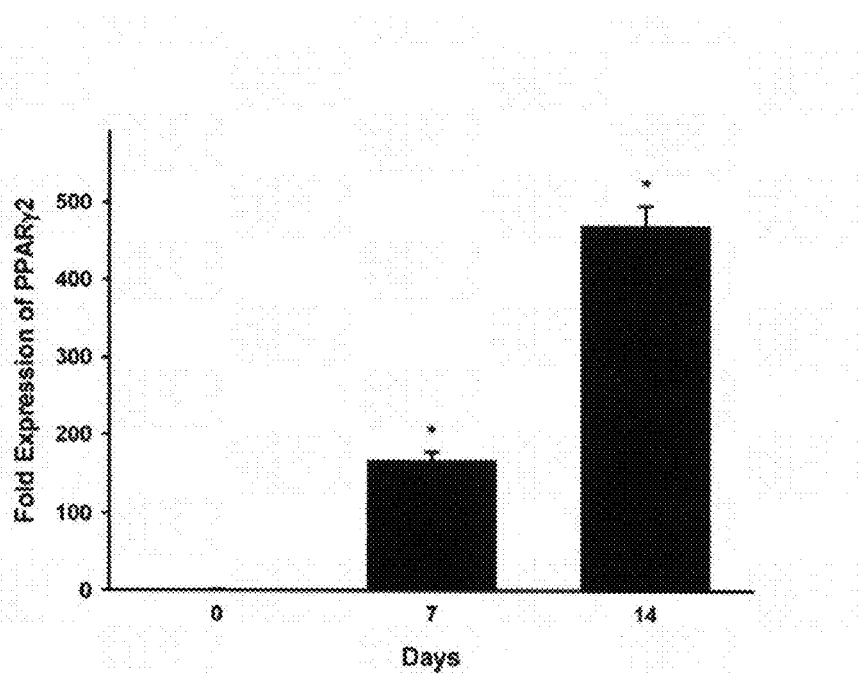
Fig. 21B
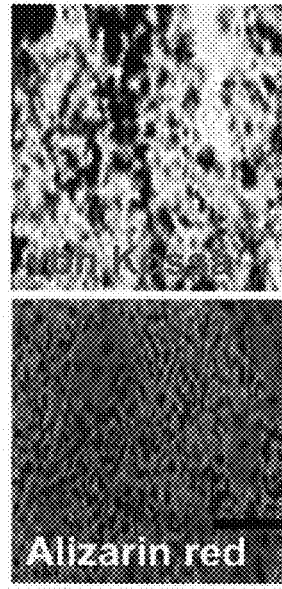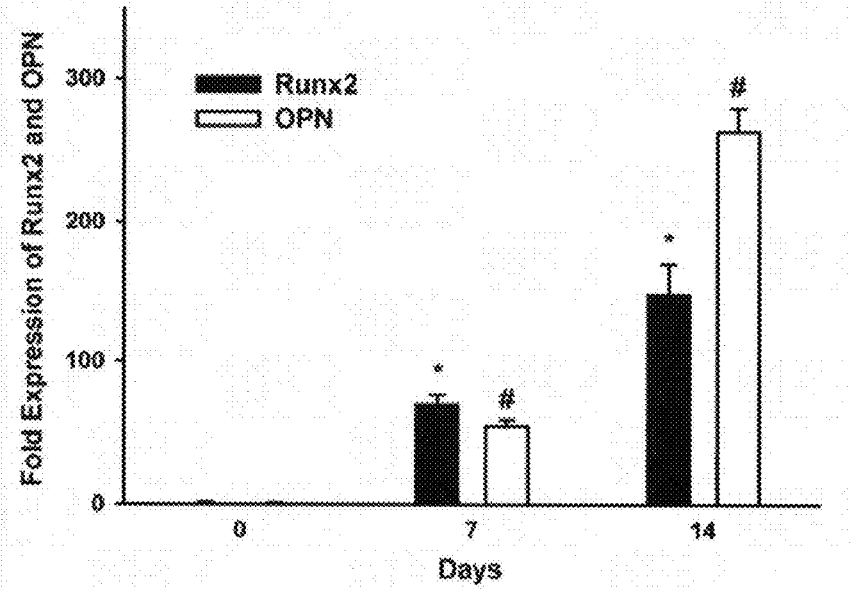

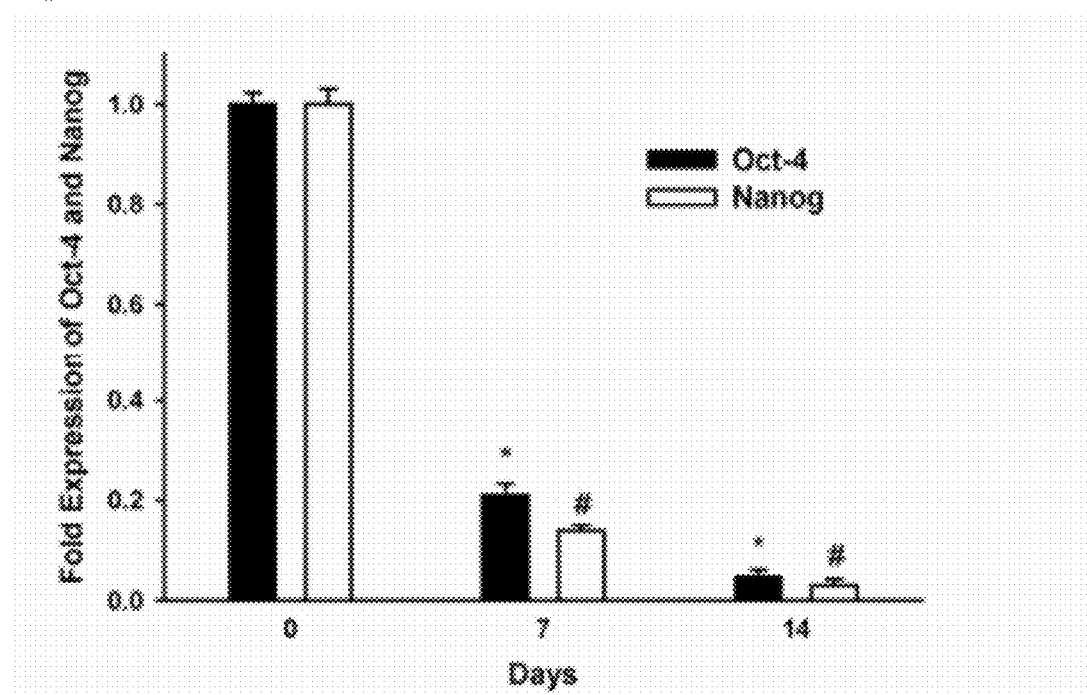

MEDIUM AND DEVICE FOR PROLIFERATION OF STEM CELLS AND TREATMENT OF CANCER-RELATED STEM CELL WITH RESVERATROL

CROSS-REFERENCE TO RELATED APPLICATION

This non-provisional application claims priority under 35 U.S.C. §119(a) on Patent Application No(s). 097132616 filed in Taiwan, R.O.C. on Aug. 27, 2008, the entire contents of which are hereby incorporated by reference.

BACKGROUND OF THE INVENTION

1. Field of the Invention

The invention relates to a device for selecting stem cells with a serum free medium for proliferation of stem cells. The present invention also relates to a method of treating or preventing diseases caused by cancer-related stem cells comprising administrating a therapeutically effective amount of resveratrol.

2. Description of the Related Art

Progenitor cells, also called stem cells, indicate the cells in original and retain the ability to renew themselves through mitotic cell division and can differentiate into a diverse range of specialized cell types. Research in the stem cell field grew out of findings by Canadian scientists Ernest A. McCulloch and James E. Till in the 1960s. According to the potency of differentiation, all the stem cells can basically be divided into three kinds of types: the first kind of type is the totipotent stem cells, which by themself are able to give rise to an entire embryo and have the very strong differentiation ability to prolify infinitly and form multiple cells, tissues, organs, and even individuals. The second kind of type is the pluripotent stem cells, this kind of stem cell also has the potency to specialize into many kinds of cells or tissues. The difference between the second kind and the preceding one is that the pluripotent stem cells are not capable of develop a whole individual and the potential growth is limit in some way. The third kind of type is the unipotent stem cells, which are only able to progress differentiation of one function or two functions cells with closed-relationship. Traditionally, people assume that neural stem cells and so on can only transform into neurons with closed functions like astrocytes and oligodendrocytes. However, the transdifferentiation studies demonstrate that neural stem cells also have the ability of differentiation being hematopoietic cells. Furthermore, rely on the source of the stem cells, all of them can be group into inner cell mass or embryonic germ cells and undifferentiated adult stem cells gathered from tissues. The former comes from teratoma, morula, inner cell mass, embryoid bodies or progenitor cells. The latter comes from neuron, blood, meschymal, epidermal or lipid.

Recently, more and more studies demonstrate that the cells isolated from partial tumor tissues also possess the characteristics of stem cells. Back to 1937, Jacob Furth and colleagues showed that leukemia can be transmitted from one mouse to another using a single undifferentiated leukemia cell. In 1963, Robert Bruce and Hugo Van der Gaag used the spleen colony-forming assay (CFU-S)—a tool first developed by James Till and Ernest McCulloch, and now widely used in stem-cell biology—to show that only a small subset of primary cancer tissue was able to proliferate in vivo. Collectively, these studies underscored the functional heterogeneity in tumours—not every cell is able to proliferate to form a colony in vitro or to give rise to a tumour when transplanted in vivo—and introduced the concept of CSCs. Thus, the CSCs have been proved from the tissues of leukemia, brain tumor, nasopharyngeal carcinoma, lung tumor and so on. (Bergsagel D. E. et al., Cancer Res, 1968, vol. 28, 2187-96 ○ Park C. H. et al., J Natl Cancer Ins, 1971, vol. 46, 411-22 ○ Heppner G. H. et al., Cancer Res, 1984, vol. 44, 2259-65).

Cancer-related stem cells are a sub-population of cancer cells that possess characteristics normally associated with stem cells. These cells are believed to be tumorigenic (tumor-forming), in contrast to the bulk of cancer cells, which are thought to be non-tumorigenic. Cancer-related stem cells have stem cell properties such as self-renewal and the ability to differentiate into multiple cell types. A theory suggests such cells persist in tumors as a distinct population and cause relapse and metastasis by giving rise to new tumors. Development of specific therapies targeted at cancer-related stem cells holds hope for sufferers of metastatic disease.

While stem cells are best defined functionally, a number of molecular markers have been used to characterize various stem cell populations. Although functions have yet to be ascertained for many of these early markers, their unique expression pattern and timing provide a useful tool for scientists to initially identify as well as isolate stem cells.

Cancer-related stem cells are extracted from the organs of adult individuals. At present believed that, the molecular markers and cellular mophology of the cancer-related stem cells are similar with those of the adult stem cells. Detection of surface antigens or specific transcriptional factors is used as molecular markers. Generally acknowledged markers are briefly being classified as four groups as followed. The first subset used to detect the embryonic stem cells includes surface markers such as stage specific embryonic antigen 3 (SSEA3), stage specific embryonic antigen 4 (SSEA4), tumor resistant antigen-1-60 (Tra-1-60) and tumor resistant antigen-1-81 (Tra-1-81) and stemness genes such as IPS-Oct4, Nanog, SOX2, Klf-4, c-Myc and Lin28. The second subset used to affirm the existence of hematopoietic stem cells includes CD34, CD133 and ATP-binding cassette superfamily G member 2 (ABCG2). The third subset used to confirm whether neural stem cells comprises nestin, polysialic acid-neural cell adhesion molecule (PSA-NCAM) and p75 neurotropin R (NTR). The forth subset required to recognize mesenchymal stem cells is STRO-1, an antibody to identify stromal precursors.

Muhammad figured out the specific surface molecular markers aimed at breast cancer-related stem cells, such as CD44, CD24, B38.1 and epithelial specific antigen (Muhammad A. H. et al., 2003, Proc. Natl. Acd. Sci. USA, vol. 100, 3989-88). Other scientists also indicated CD133 as the marker of colon or prostate cancer-related stem cells (Catherine A. O. et al., Nature, 2007, vol. 445, 106-110 ○ Gavin D. et al., J Cell Sci, 2003, vol. 117, 3539-45). Besides, Wolf suggested that side population cells is the characteristic of cancer-related stem cells (Wolf N. S. et al., Exp Hematol, 1993, vol. 21, 614-22 ○ Wolf N. S. et al., Blood, 2001, vol. 98, 1166-73). Moreover, Max S. Wicha and his colleagues utilized aldehyde dehydrogenase 1 (ALDH-1) as a marker to identify normal or malignant human cancer-related stem cells. However, as to stemness genes detection, the genes mentioned above could be proved in the following references, such as Chamber I. et al., Cell, 2003, vol. 113, 643-55; Mitsui K. et al., Cell, 2003, vol. 113, 631-42; Schöler, H. R. et al., Trends Genet, 1991, vol. 7, 323-329; Maurizio P et al., Stem Cells, 2001, vol. 19, 271-8).

Isolation and cultivate stem cells after identifying the characteristic of them for sequential basic research of gene regulation, human repair or the application of being drug candidate screening platform. Selective culture medium provides cells not only an amount of nutrients to replicate, but also acts as a screening tool of identifying subsets toward particular differentiation pathway. Take neural stem cells for example, cells was cultured with serum free medium containing insulin, transferrin, sodium selenite, fibroblast growth factor, fibronectin and so on for increasing a great amount of neural epithelial progenitor cells possessing the expression of nestin. Besides, sonic hedgehog was added to the cultured differentiated neural cells and led cells tend to augment numbers of cells expressing NKx6.1 and Olig2, the characteristic of ventral lateral neurons.

In some embodiments, embryonic stem cells were cultivated as embryoid bodies for four days with the medium further containing fibronectin. Therefore, approximately 85% of all like neural epithelial cells subset in morphology expressed the surface marker of neural epithelial cells, nestin. Furthermore, to add fibroblast growth factor 2 would promote cellular survival and amplification greatly, but enhance the neural cells to differentiate. If removal of fibroblast growth factor 2, there would be a great amount of cells dead. Treat cell as above, another problem presented was that there was still expression of epithelial cells' marker, such as cytokeratin 18. At the same time, pluripotent stem cells present and could be recognized from some cellular population by detecting whether stage specific embryonic antigen 1 or not.

Another method used medium to selectively promote neural cells tend to differentiate was treating embryonic stem cells in nearly low cells density with leukemia inhibitory factor. Like this, we could get neural cell clusters comprising about 100% neural progenitor cells expressing nestin. Some researchers were under the impression that such cells were neural stem cells because this kind of cells would response to leukemia inhibitor factor, but fibroblast growth factor 2. Another interesting opinion was that retinol acid is not apparently essential to differentiated neural cells. Back to the words, treating cells only with leukemia inhibitory factor would get low survival rate of its, about one of 2000. Hence, such method is not a normal approach to differentiate neural cells.

Cytokines is considered to be related closely to amplification and differentiation of neural stem cells. Several cytokines might induce the important activated differentiation. Nevertheless, there is no such cytokine able to induce neural progenitor cells to transform into functional stem cells in vitro. Interleukins are some of them, such as interleukin 1, interleukin 7, interleukin 9, interleukin 11 and so on. Neurotrophie factor can affect whole processing of differentiation. If treat neural stem cells with brain-derived neurotrophie factor, plenty of them will possess the characteristic of neurons. As to growth factors, such as epithelial growth factor, neural growth factor, or basic fibroblast growth factor, they also influence the differentiation of neural stem cells. The responses to assorted, various concentrations and multiple combined treating are distinct from each others. Even the same factors applied to different stages of development and differentiation of neural stem cells, they cause diverse regulations. Therefore, to cultivate cells in the presence of epithelial growth factor and basic fibroblast growth factor would direct embryonic neural stem cells to develop toward neurons, astrocytes and oligodendrocytes. Fetal and adult brain neural stem cells, treated with or without epithelial growth factor and basic fibroblast growth factor developed majorly into astrocytes. These studies suggested that the epithelial growth factor or basic fibroblast growth factor-induced differentiation is complicated. Besides, referring to chemicals, retinoic acid is commonly used on account of its important roles in the process of embryo growth, especially in the development of neurons.

Related techniques derived from selectively culturing cancer-related stem cells are compared as following.

Human breast tumor tissues after cellular matrix being trypsinized were injected subcutaneously into severe combined immunodeficient mice as previous study described in Muhammad A. H. et al, PNAS, 2003, vol. 100, 3983-3988. Human cancer-related stem cells were able to form tumor tissues in mice in vivo. Afterwards, human cancer-related stem cells possessing the properties of highly differentiation and self-renewal were isolated from mice for only discussing the mechanism, but the procedure could not be done in a great quantity.

Cancer-related stem cells were selected from brain tumor primary tissue cultures with cancer spheroid cells selecting medium and the methodology was published by Sheila K. S. and his associates in the Chinese journal of Cancer Research in the same year. In brief, the scientific group provided us a steady and effective selective culture medium in vitro, a serum-free medium containing 20 ng/ml human recombinant epithelial growth factor, 20 ng/ml basic fibroblast growth factor, 10 ng/ml leukemia inhibitory factor, 1× neural survival factor and 60 µg/ml acetyl cysteine. The disadvantage of its was so expensive that plenty of experiments used above recombinant proteins needed enough budgets (Sheila K. S. et al., Cancer Research, 2003, vol. 63, 5821-5828).

Another proof of stimulating the proliferation of endometrial stroma cells was cultivating isolated cells with 10 ng/ml lactoferrin in vitro (Atsushi Yanaihara et al., Molecular Human Reproduction, 2000, vol. 6, 469-473). Andrew Grey and his colleague promoted the differentiation and survival of osteoblasts by treating cells with lactoferrin in vitro (Andrew Grey et al., Molecular Endocrinology, 2004, vol. 16, 2268-2278). The medium containing 2% fetal bovine serum was supplied in previous reference, and medium containing 5% fetal calf serum was in latter one. The above two culturing systems were not suitable for highly throughput screening with such serum-contained medium.

Li, Ming-Chu and his fellow workers illustrated how to select and identify the cancer-related stem cells from primary human medulloblasts. In brief, cancer-related stem cells isolated from patients' tissues to be single-cell suspension followed by inoculating into the serum-free medium consisting of epithelial growth factor, fibroblast growth factor and B27 supplement to cultivate in suspension. In order to assertain the percentage of cancer-related stem cells, they tested monocolony forming assay accompanied with subculturing spheroid cells continuously. Thereafter, the cancer-related stem cells grew in the medium with serum and the phenomenon were investigated (Li, M. C. et al., Cancer (in Chinese), vol. 2).

Ouyang, Zhen and his colleague obtained spheroid cells and subsequently cultured them with serum-free DMEM/F12K medium comprising 20 µg/ml epithelial growth factor, 20 µg/ml basic fibroblast growth factor, 2 µmole/L L-Glutamine, 4 U/L insulin, 100 U/mL Penicillin G and 100 U/mL Streptomycin with pH of 7.2 to 7.5. The Stro-1+ cells were isolated by immunomagnetic beads as cancer-related stem cells (Ouyang. Z. et al., Zhongguo Zuzhi Gongcheng Yanjiu yu Linchuang Kangfu, 2007, vol. 11(24), 4706-4709).

Akio S. discussed how important the epithelial growth factor was in the progress of cells' proliferation. The culturing condition was serum-free DMEM/F12K medium containing streptomycin, penicillin G, B27 supplement, 20 µg/ml epithelial growth factor, 20 µg/ml fibroblast growth factor, 1000

U/ml leukemia inhibitory factor. Besides, the authors suggested that only epithelial growth factor could induce the formation of spheroid cells and increase the capability of self-renew (Akio S. et al., J. BioChem, 2008, vol. 3, 1-10).

Others desired to find out the ways of how to identify neural stem cells so as to have a cure for neuropathy or have an idea to discover the presence of brain tumors. Mouse neural stem cells were selected and grew in the NSC medium consisting of 20 μg/ml epithelial growth factor, 20 μg/ml fibroblast growth factor and 2 μg/ml heparin. Medium was exchanged at two or three day-interval (Phedias et al., Nature Chemical Biology, 2007, vol. 3, 268-273).

In conclusion, at present selective culture to screen cancer-related stem cells is nothing more than using medium consisting of salts, vitamins, amino acids and even further to add some cytokines to promote the amplification of cells. Thereafter, isolated by traditional Transwell® approach and then scratch them or by flow cytometry employed with immunomafnetic beads. As rapidly as the development of biotechnology, such as genetic engineering, embryonic engineering, cellular engineering, tissue engineering and so on, more and more in vitro methods present to satisfy predicted purpose. The major applications of stem cells were being supply sources for translating every kind of cells, tissues and organs, hence cell culturing methodology and device of being used conveniently, clear mechanism, speed and suitable for curing diseases or high throughout screening of new dug candidates will be the critical points of development and modification. However, recently thermoresponsive materials such as poly (N-isopropyl acrylamide) (PNIPAAm), was applied to tissue engineering. Harimoto M and his fellow workers disclosed a novel method of co-culturing double cellular layers in the reference named "Ectopic transplantation of hepatocyte sheets fabricated with temperature-responsive culture dishes" (Harimoto M et al., J Biomed Mater Res., 2002, 62(3):464-70). Another research group also claimed a method to rebuild the corneal epithelial cells by making use of the cellular film of bioengineering (Hsiue G H et al., Transplantation, 2006, 81(3):473-6). Besides, Japanese CellSeed company further applied the thermoresponsive materials into culturing devices, such as culturing dishes or microplates.

Drug candidates screening is one step of modern medicine research and development procedure to detect and acquire compounds possessing particular bioactivity. In more details, it is a process to select compounds targeting specific bio-function and owning high efficacy through experimentation normalized by standard operation protocols.

Screening model being used in the drug screening experiments as a model of pharmacology experiments. For acquiring standardization and quantify, animal studies were commonly used in traditional pharmacology experiments, but not drugs screening. In light of the difference of experimental models, drugs screening could be classified into biochemistry-level and cell-level screening. Cell-level screening model, a mode more approaching physical condition, applied cell culturing techniques to obtain the target cells, which were purposed to have some specific therapeutic reactions. Thereafter, those cells treated with the drug candidates to determine the bio-activity of them through assays similar with biochemistry-level detection. There were four factors which were not only the critical elements in the process of virtual drugs screening, but a bottleneck to limit the accuracy of it, to build a proper pharmacophore model, to test exactly, to predict the molecular structures of the target proteins, and to calculate the charge of the free energy between the candidates and target cells. Although the accuracy needed to be raised, the high speed and low-priced of it make itself to become one of the fast development drugs screening systems. Scientists further pointed out cancer-related stem cells could resist currently medical therapy and proceed DNA repair after radiotherapy. Deserved to be mentioned, above features could be observed in parent cells stronger and more frequently than daughter cells. A topic report in Nature Biotechnology addressed that pharmaceutical companies had been traced cancer-related stem cells. Studies on cancer-related stem cells had been one of the strategies of researching and developing the anti-cancer drugs in some biotechnology or pharmaceutical firms, such as GlaxoSmithKline, Geron corp. (LA, US), Stemline Therapeutics, Inc. (NY, US), OncoMed Pharmaceuticals, Raven Biotechnologies Inc., Arius Research Inc., and Immunocellular Therapeutics Ltd. GlaxoSmithKline' Tyverb, a breast cancer small molecule drug, got FDA's approval and is going to reach the market first (Charlei S., Nature Biotechnology, 2008, vol. 26, 366-367).

EP 0513896 B1 disclosed a novel medium for the preservation of live organs, biological tissues or cells. This medium is composed of a liquid biological nutrient base such as a cell culture medium, enriched by a small amount of peroxidase enzyme proteins such as lactoperoxidase and/or enzymatic proteins with ferriheme such as lactoferrin. In particular, the invention can be applied to the preservation of corneas, but there were not mentioned that the medium can be used to proliferating stem cells.

The purpose of this invention is to supply the cell culturing methodology of being used conveniently, clear mechanism, speed and suitable for curing diseases or high throughout screening of new dug candidates. All references, including publications, patent applications, and patents, cited herein are hereby incorporated by reference to the same extent as if each reference were individually and specifically indicated to be incorporated by reference and were set forth in its entirety herein.

Tumor formation in vitro displayed significant resistance to radiotherapy. The expression of embryonic stem cell genes such as Oct-4 and Nanog have been correlated with tumorigenesis and self-renewing activity, and can affect some aspects of tumor behavior such as recurrence and resistance to therapy. Recently, the expression of Oct-4, Nanog, and was shown in cancer-related stem cells derived from human oral, breast, and brain tumors, suggesting that their expression may be implicated in self-renewal and tumorigenesis via activating downstream target genes (Zhang H et al., J cell Biocham, 2008, vol. 103, 709-718).

Resveratrol (3,4',5-tri-hydroxy-trans-stilbene), a natural polyphenol, is mostly found in grapes, red wine, and peanuts (Bradamante S et al., Drug Rev, 2004, vol. 22, 169-188). It possesses several pharmacological effects that are closely related to health therapies including cardiac protection as well as anti-viral, anti-inflammatory, and anti-aging activities and lifespan extension. Importantly, recent researches demonstrated that resveratrol (RV) has an anti-cancer effect and inhibits tumorigenesis by inducing apoptosis via Fas-, P53-, and P21$^{WAF/CIP1}$-mediated pathways (Atten M J et al., Invest New Drug, 2005, vol. 23, 111-119; Kuo P L et al., Life Sci, 2002, vol. 72, 23-24; Roccaro A M et al., Clin Cancer Res, 2008, vol. 14, 1849-1858). Furthermore, some reports indicated that RV can also increase radiosensitivity in several cancer cell lines including melanoma, cervix carcinoma, chronic myeloid leukemia (K-562), and multiple myeloma (IM-9) (Johnson G E et al., Apoptosis, 2008, vol. 13, 790-802; Baatout S et al., Int J Mol Med. 2004, vol. 13, 895-902).

U.S. Pat. No. 7,455,860 discloses "Dietary supplement formulation for controlling inflammation and cancer", relating to a dietary supplement which is a phytochemical composition. This composition is capable of controlling inflammatory conditions and preventing and curing cancer in mammals. The composition comprises a synergistic mixture of standardized Boswellia extract, salts of glucosamine, and curcuminoids optionally containing bromelain, chondroitin, methylsulphonylmethane, resveratrol, extracts of white Willow and ginger, and quercetin.

U.S. Pat. No. 6,008,260 discloses "Cancer chemopreventative composition and method", which relates to a composition and method of cancer chemoprevention. The composition and method utilize resveratrol as a cancer chemopreventative agent in mammals, including humans.

Previous studies suggested that resveratrol (RV) could also increase radiosensitivity via several mechanisms, including inactivation of NF-κB and increased S phase cell cycle arrest. Recent studies showed that RV-induced apoptosis not only inhibits tumor growth but also acts as a radiochemosensitizer for anti-cancer therapy (Johnson G E et al., Apoptosis, 2008, vol. 13, 790-802; Baatout S et al., Int J Mol Med, 2004, vol. 13, 895-902). However, the treatment of role of RV in cancer-related stem cell and RV-mediated radiosensitizing effects in the treatment of cancer-related stem cells were still undetermined.

Adult stem cells from bone marrow and other tissues have been shown to be able to differentiate into many types of cells, including osteocytes, chondrocytes, smooth muscle cells, hepatocytes, cardiomyocytes, neurons, and retinal cells. They are considered promising resources for restorative cell therapy of various diseases. Recently, Yamanaka and colleagues demonstrated that induced pluripotent stem (iPS) cells could be generated from mouse embryonic fibroblasts as well as from adult human fibroblasts via the retrovirus-mediated transfection of four transcription factors, i.e., Oct3/4, Sox2, c-Myc, and Klf4. These iPS cells are indistinguishable from embryonic stem (ES) cells in morphology, proliferative abilities, surface antigens, gene expressions, epigenetic status of pluripotent cell-specific genes, and telomerase activity. The major advantage of iPS cells over ES cells is that iPS cells can be derived from patient's own somatic cells, thereby avoiding immune rejection after transplantation and ethical concerns raised in ES cells. However, previous studies have shown that transplanted iPS cells are likely to from teratoma in vivo because of the genetic changes intrinsic to the iPS cells generation process may pose risk of enhancing tumorigenesis through both the introduced genes themselves and in theory via the potential changes at specific integration sites, a feature also found in ES cells. The ability to form teratomas in vivo has been a landmark and routine assay for evaluating the pluripotency of ES as well as iPS cells, however, teratoma formation from pluripotent stem cells is considered as an unacceptable obstacle for the application of stem cell therapy in regenerative medicine. Thus, the regenerative medicine field is faced with a dilemma situation in that if one seeks to make stem cells safer by lowering Myc levels, a tandem reduction in the "stemness" of those cells may prove inevitable. The same appears to be true for other master stem cell regulators such as KLF4. Lowered levels of KLF family members including KLF4 substantially impaired ESC pluripotency and self-renewal, forcing ESC to differentiate. In other words, it is very hard to preserve self-renewal and pluripotency while eliminating tumorigenicity. Therefore, measures to overcome the tumorigenicity of iPS cells are crucial for successful treatment of patients with iPS cells.

SUMMARY OF THE INVENTION

This present invention provides a device for selecting stem cells, consisting of, but not exclusive to, (a) an upper chamber, comprising: (i) a filter membrane between upper chamber and lower chamber, (ii) the filter membrane attached with NIP-PAMS, (iii) cell enrichment medium; and (b) a lower chamber coating with the cytomovement attractants.

The present invention also provides a novel serum-free medium for proliferation of embryonic stem cells, adult stem cells or tumor stem cells, consisting of, but not exclusive to, lactoferrin. Salts, vitamins, amino acids, epithelial growth factor, basic-fibroblast growth factor or transferrin may further be added.

This invention also provides a method for treating or preventing diseases caused by cancer-related stem cells or improving the survival rate comprising administrating a therapeutically effective amount of resveratrol.

This invention further provides a method of enhancing radiosensitivity of cancer-related stem cells comprising radiotherapy with resveratrol, and the cancer-related stem cells have stronger drug resistance.

This invention further provides a method of promoting induced pluripotent stem cells (iPS) and embryonic stem cells to be differentiated or preventing tumor formation comprising administrating an individual an effective amount of resveratrol.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 demonstrates the schematic diagram of culturing stem cells herein.

FIG. 21 shows potential for adipogenic and osteogenic differentiation in iPS cells. (A) After 14 days of adipogenic induction, iPS cells were able to differentiate into adipocytes with positive oil red O staining and much higher expression of PPARr2 (an adipogenic gene). mRNA. (B) Following 14 days of osteogenic differentiation, iPS cells differentiated into osteocyte-like cells with a mineralized matrix, as detected by von Kossa and Alizarin red staining, and markedly elevated expression of Runx2 and OPN (two osteogenic markers). (C) The mRNA levels of Oct-4 and Nanog significantly decreased in iPS cells after 7 and 14 days of osteogenic induction. Data shown here are the mean±SD of three independent experiments. *, #P<0.05 compared to control (Day 0). Bar=50 μm.

FIG. 25 shows iPS cells were cultured either in control medium (iPS) or in osteogenic induction medium (OIM) for 7 days, followed by injection of $2\times10^6$ cells into subcutaneous sites of nude mice fed with resveratrol (iPS+OIM+RV) or control vehicle (iPS+OIM). Six weeks after transplantation, RNA was extracted from the grafts from the three groups (Each group, N=6) and then quantitative RT-PCR was performed to measure expressions of Oct-4 (A), Nanog (B), Klf-4 (C), and c-Myc. Data shown here are the mean±SD of three independent experiments. *P<0.05.

DETAILED DESCRIPTION OF THE INVENTION

Figure 1A:
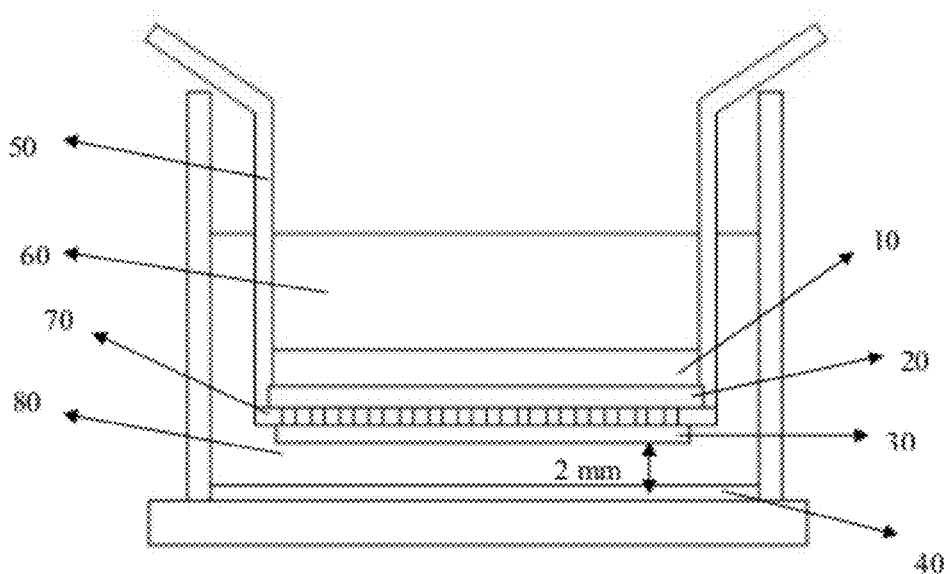
FIG. 1 shows a device for selecting cancer-related stem cell with a serum free medium of this invention.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Certain embodiments of this invention are described herein, including the best mode known to the inventors for carrying out the invention. It should be understood that the illustrated embodiments are exemplary only, and should not be taken as limiting the scope of the invention.

The present invention provides a serum-free medium for proliferation of stem cells comprising lactoferrin. In a preferred embodiment, the medium further comprising salts, vitamins, amino acids, epithelial growth factor, basic-fibroblast or transferring.

The term 'stem cell' used herein, refers to cells found in most, if not all, multi-cellular organisms. They are characterized by the ability to renew themselves through mitotic cell division and differentiating into a diverse range of specialized cell types, which includes but is not limited to embryonic stem cells, adult stem cells, tumor stem cells or progenitor cells.

The term 'lactoferrin' used herein, refers to a globular multifunctional protein with antimicrobial activity and is part of the innate defense, mainly at mucoses. Lactoferrin is found in milk and many mucosal secretions such as tears and saliva. Lactoferrin is also present in secondary granules of PMN and also is secreted by some acinar cells. Lactoferrin can be purified from milk or produced recombinantly.

The present invention further provides a method of treating or preventing diseases caused by cancer-related stem cells comprising administrating a therapeutically effective amount of resveratrol.

The term 'cancer-related stem cell' used herein includes but is not limited brain cancer-related stem cells, oral cancer-related stem cells, head and neck cancer-related stem cells, breast cancer-related stem cells, stomach cancer-related stem cells, pancreas cancer-related stem cells, liver cancer-related stem cells, kidney cancer-related stem cells, bladder cancer-related stem cells, colon cancer-related stem cells, and prostate cancer-related stem cells.

The term 'resveratrol' used herein refers to a phytoalexin produced naturally by several plants when under attack by pathogens such as bacteria or fungi. Resveratrol has also been produced by chemical synthesis and is sold as a nutritional supplement derived primarily from Japanese knotweed. Resveratrol has been shown at times to extend the life span of yeast and mice. In mouse and rat experiments, anti-cancer, anti-inflammatory, blood-sugar-lowering, chelating and other beneficial cardiovascular effects of resveratrol have been reported. Most of these results have yet to be replicated in humans.

The present invention further provides a method of enhancing radiosensitivity of cancer-related stem cells comprising radiotherapy with resveratrol. The effective amount is 50 to 150 μM, more preferably is 50 to 100 μM, and the most preferably is 50 μM.

This present invention further provides a device for selecting stem cells, consisting of, but not exclusive to, (a) an upper chamber, from top to down, comprising: (i) a filter membrane between upper chamber and lower chamber, (ii) the filter membrane attached with NIPPAMS, (iii) cytomovement attractants; and (b) a lower chamber coating with the cytomovement attractants. Besides, cytomovement attractants, such as fibronectin, poly-onithine, lamimin or thymosin B4 is further spread onto the micro porous membrane or lower compartment to facilitate cellular movement.

This present invention further provides a method for selecting stem cells comprising (a) applying cells isolated from tissues with medium into the lower chamber of the present device; (b) inserting the upper chamber into lower chamber, and (c) lowering the temperature of upper chamber to segregate the cell-contained NIPPAMs layer from the unit. For instance, the upper unit can be cool down by placing into cold water. Subsequently, cell-contained NIPPAMs layer was added cells sorting solution to extract the cells.

This present invention further provides a method for identifying cancer-related stem cell, comprising the characteristics (a) increasing the formation of spheroid cells; (b) changing expression of stemness genes IPS-Oct4, Nanog, SOX2, Klf-4, c-Myc and Lin28; (c) positive response for CD133, ATP-binding cassette superfamily G member 2 (ABCG2), ALDH-1 and CD117 and increasing amount of side population; (d) in vitro tumor occurrence; (e) tumorgenesis after heterogeneity transplanted in vivo; and (f) anti-chemotherapy and anti-radiosensitization.

The present invention also provides that RV treated cancer-related stem cells which is radioresistance treating with Taxol and Doxorubicin had more stronger drug resistance compared with cancer-related stem cells without treating RV, and the result is caused by elevation of the ATP-binding cassette transporter genes including ABCC1, ABCC2, and ABCB1.

The term 'Taxol' used herein refers to a mitotic inhibitor used in cancer chemotherapy. Taxol is now used to treat patients with lung, ovarian, breast cancer, head and neck cancer, and advanced forms of Kaposi's sarcoma. Taxol is also used for the prevention of restenosis. Taxol stabilizes microtubules and as a result, interferes with the normal breakdown of microtubules during cell division.

The term 'Doxorubicin' used herein is a drug used in cancer chemotherapy. It is an anthracycline antibiotic, closely related to the natural product daunomycin, and like all anthracyclines it intercalates DNA. It is commonly used in the treatment of a wide range of cancers, including hematological malignancies, many types of carcinoma, and soft tissue sarcomas.

The term 'stemness gene' used herein means a gene in maintaining properties that are common to all stem cells.

The term 'Oct-4' used herein is an abbreviation of Octamer-4, which is a homeodomain transcription factor gene of the POU family. This product of this gene is critically involved in the self-renewal of undifferentiated embryonic stem cells. As such, it is frequently used as a marker for undifferentiated cells.

The term 'Nanog' used herein is a gene expressed in embryonic stem cells (ESCs) and is thought to be a key factor in maintaining pluripotency. Nanog functions in concert with other factors such as POU5F1 and SOX2 to establish ESC identity.

The term 'Klf-4' used herein is gut-enriched Krüppel-like factor (GKLF) gene which product acts as a transcriptional activator or repressor depending on the promoter context and/or cooperation with other transcription factors.

The term 'Sox-2' used herein is a transcription factor gene that is essential to maintain self-renewal of undifferentiated embryonic stem cells.

The term 'c-Myc' used herein is a transcription factor gene that is essential to maintain self-renewal of undifferentiated embryonic stem cells. It regulates expression of 15% of all genes through binding on Enhancer Box sequences (E-boxes) and recruiting histone acetyltransferases (HATs).

The term 'MDR-1' used herein is a gene which is located on the long arm of chromosome 7 and consists of a core promoter region and 29 exons. The product of the gene protein functions as an energy-dependent drug efflux pump and reduces the intracellular concentrations of a wide range of drugs and xenobiotics.

The term 'ABCG2' used herein means ATP-binding cassette, sub-family G (WHITE), member 2, is a human gene. ABCG2 has also been designated as CDw338 (cluster of differentiation w338). This protein of this gene is a member of the White subfamily, and this protein functions as a xenobiotic transporter which plays a major role in multi-drug resistance.

The term 'MRP-1' used herein also known as CD9, is a human gene. The protein encoded by this gene is a member of the transmembrane 4 superfamily, also known as the tetraspanin family. Most of these members are cell-surface proteins that are characterized by the presence of four hydrophobic domains. The proteins mediate signal transduction events that play a role in the regulation of cell development, activation, growth and motility. This encoded protein is a cell surface glycoprotein that is known to complex with integrins and other transmembrane 4 superfamily proteins. It can modulate cell adhesion and migration and also trigger platelet activation and aggregation. In addition, the protein appears to promote muscle cell fusion and support myotube maintenance.

The term 'survivin', also called Baculoviral IAP repeat-containing 5 (BIRC5), is a human gene that is part of the inhibitor of apoptosis family (IAP). The survivin protein can inhibit caspase activation therefore leading to negative regulation of apoptosis or programmed cell death. The survivin protein is expressed highly in most human tumours and fetal tissue. It is known that survivin localizes to the mitotic spindle by interaction with tubulin during mitosis and may play a contributing role in regulating mitosis.

This invention further provides a method of downregulating stemness gene of cancer-related stem cells comprising treatment of cancer-related stem cells with resveratrol. The stemness gene of cancer-related stem cells include but is not limited to Oct-4, Nanog, Klf-4, Sox-2, c-Myc, MDR-1, ABCG2, MRP-1, and Survivin.

The present invention also provides a method of promoting induced pluripotent stem cells (iPS) and embryonic stem cells to differentiate and inhibiting tumorigenicity comprising administrating an individual an effective amount of resveratrol.

The term 'induced pluripotent stem cells (iPS)' used herein is a type of pluripotent stem cell artificially derived from a non-pluripotent cell, typically an adult somatic cell, by inducing a "forced" expression of certain genes. Induced Pluripotent Stem Cells are believed to be identical to natural pluripotent stem cells, such as embryonic stem cells in many respects, such as the expression of certain stem cell genes and proteins, chromatin methylation patterns, doubling time, embryoid body formation, teratoma formation, viable chimera formation, and potency and differentiability, but the full extent of their relation to natural pluripotent stem cells is still being assessed.

The term 'embryonic stem cells' used herein are stem cells derived from the inner cell mass of an early stage embryo known as a blastocyst.

The term "stem cell therapy" refers to a type of cell therapy that introduce new cells into damaged tissue in order to treat a disease or injury. Many medical researchers believe that stem cell treatments have the potential to change the face of human disease and alleviate suffering. The ability of stem cells to self-renew and give rise to subsequent generations that can differentiate offers a large potential to culture tissues that can replace diseased and damaged tissues in the body, without the risk of rejection. The "stem cell therapy" used in the present invention includes but is not limited to iPS cell therapy and ES cell therapy.

A recent breakthrough has demonstrated that ectopic expression of four genes is sufficient to reprogram murine and human fibroblasts into induced pluripotent stem (iPS) cells. However, the teratoma formation iPS cells is still a safety problem and an open question. In the present invention, it is found that resveratrol can facilitate differentiation in both iPS and embryonic stem cells, as shown by increased mineralization, up-regulation of osteogenic markers, and decreased elastic modulus. Transplantation experiments using iPS cell-derived osteocyte-like cells further demonstrated that oral intake of resveratrol could up-regulate osteopontin expression and inhibit teratoma formation in vivo. In sum, resveratrol can facilitate differentiation of iPS cells and ES cells and decrease tumorigenicity of iPS cells and ES cells, may through activation of SirT1 which inhibits the activity of surviving. These findings implicate roles of resveratrol and iPS cells or ES cells in the stem cell therapy in the future clinical.

EXAMPLES

Example 1

Preparation of Thermoresponsive Hydrogel Stripped Easily Layer

The procedure of preparation of thermoresponsive hydrogel stripped easily layer shown in FIG. 1. In brief, The carrier was exposed to vacuum over at 40 mtorr followed by passing Arkansas gas till the pressure went to 250 mtorr, and then polymerized by plasma (power: 50 W; time: 10 min) to produce free radicals and activate the surface. The carrier was being immersed in 6% NIPAAMs (wt/volume) solution with 0.026 gram of ammonium peroxodisulfate (APS), 0.04 mL of N,N,N-tetra-methylethylene-diamine (TEMED) and 0.5 gram of N,N-methyl-enebisacrylamide (NMBA). 0.01 g/L of Vit-B2 was adding into the NIPAAMs solution in the ratio of 4:1 (NIPAAMs solution: Vit-B2) and spreading onto the carrier. Thereafter, 65° C. water-bathing last for 1 hour could make the surface of the carrier be polymerized. Later, washed the carrier by ddH2O overnight for removal of unlinked monomer. Finally, UV was applied to illuminate the carrier.

In the beginning, sterile and nylon mesh possessed Transwell® were applied to plasma treating and co-polymerization. In brief, Transwell® was exposed to vacuum over at 40 mtorr followed by passing Arkansas gas till the pressure went to 250 mtorr, and then polymerized by plasma (power: 50 W; time: 10 min) to produce free radicals and activate the surface. The Tranwell was being immersed in 10% NIPAAm (wt/volume) solution with ammonium peroxodisulfate (APS), N,N,N-tetra-methylethylene-diamine (TEMED) and N,N-methyl-enebisacrylamide (NMBA), illuminated at 256 nm of wave length and 1000 W of power and cooled it till the temperature down to 15° C. The cooling duration treated the polymerization more homogeneous.

6 well culture plates coated with fibronectin processed as FIG. 1. Cells were seeded onto the coated wells with 80% seeding cell density followed by cultivating in medium consisting of serum-free DMEM/F12 medium, N2 supplement, 10 ng/mL recombinant betaFGF, 10 ng/mL EGF, 1 µg/mL lactoferrin and 1% antibiotics. Medium were changed every 3 days till the formation of spheroid cells. Cells were transferring to the freshly prepared Transwells®. Spheroid cells were penetrating through the outer membrane of wells, nylon mesh, porous thermoresponsive surface and final matri-gel layer. In the end, cell sorting solution, BD354253, was used to isolating the cells from the matri-gel layer. FIG. 1 shows a device and the preparation of thermoresposive N-isopropylacrylamide (NIPPAMs) with serum free medium of this invention to proliferation of stem cells. The upper panel (a) represents the device of this invention. 10, a stem cells isolation coating layer; 20, a N-isopropylacrylamide layer; 30, a cell moving facilitated membrane; 40, a matrigel layer; 50, a Transwell®; 60, an upper compartment; 70, a micro porous membrane, and 80, a lower compartment. The following panel (b) depicts the flowchart illustrating the preparation of NIPPAMs. 21, the step of plasma surface treatment; 22, the step of adding mixed well NIPPAMs contained mixture; 24, the step of grafting polymerization, incubating the compartment for 1 hr in a 65° C. water bath and 26, a photolithography process, exposing the compartment to UV light for 24 hours.

Example 2

Identification of Cancer-Related Stem Cells

Isolation of Stem Cells from Normal Tissue 6 well culture plates coated with fibronectin processed as FIG. 1. Cells were seeded onto the coated wells with 80% seeding cell density followed by cultivating in medium consisting of serum-free DMEM/F12 medium, N2 supplement, 10 ng/mL recombinant betaFGF, 10 ng/mL EGF, 1 µg/mL lactoferrin and 1% antibiotics. Medium were changed every 3 days till the formation of spheroid cells. Cells were transferring to the freshly prepared Transwells®. Spheroid cells were penetrating through the outer membrane of wells, nylon mesh, porous thermoresponsive surface and final matri-gel layer. In the end, cell sorting solution, BD354253, was used to isolating the cells from the matri-gel layer. FIG. 2 demonstrates the schematic diagram of culturing stem cells herein. 41, a culture medium containing serum; 100, isolated cells; 101, the spheroid cells; 110, the cancer-related stem cells culture medium (serum-free); 111, culture medium; 210, a step of cultivating in the medium containing serum for 3 days; 220, a step of cultivating in the medium without serum for 3 days and then putting it into Transwell®; 230, a process of cultivating for 3 to 7 days; 240, a step of obtaining the cell-contained layer by cooling upper compartment, and 250, a process of transferring the cell-contained layer to another culture plate or space.

Cultivation of Spheroid Cells from Primary Tumors

Tumor samples were donated from OSCC patients and primary tumor cell were isolated by following the procedure described (J Oral Pathol Med., 33(2004)79-86). The primary cells were then cultured in tumor sphere medium consisting of serum-free DMEM/F12 medium, N2 supplement, 10 ng/mL human recombinant bFGF and 10 ng/mL EGF.

Real-Time Reverse Transcription-Polymerase Chain Reaction (RT-PCR).

Total RNA of parental oral cancer cells or derived OC-SLCs was extracted by using the $RNA_{easy}$ kit (Qiagen, Valencia, Calif.), respectively. Briefly, the total RNA (1 µg) of each sample was reversely transcribed by Superscript II RT (Invitrogen, Carlsbad, Calif.). Then, the amplification was carried out in a total volume of 20 µl containing 0.5 µM of each primer, 4 mM $MgCl_2$, 2 µl LightCycler™-FastStart DNA Master SYBR green I (Roche Molecular Systems, Alameda, Calif.) and 2 µl of 1:10 diluted cDNA. The GAPDH housekeeping gene was amplified as a reference standard. GAPDH primers were designed: GAPDH(f): GGGCCAAAAGGGT-CATCATC (nt 414-434, GenBank accession no. BC059110.1), GAPDH(r): ATGACCTTGCCCACAGCCTT (nt 713-733). PCR reactions were prepared in duplicate and heated to 95° C. for 10 minutes followed by 40 cycles of denaturation at 95° C. for 10 seconds, annealing at 55° C. for 5 seconds, and extension at 72° C. for 20 seconds. Standard curves (cycle threshold values versus template concentration) were prepared for each target gene and for the endogenous reference. To confirm the specificity of the PCR reaction, PCR products were electrophoresed on agarose gel and stained with ethidium bromide.

FACS Analysis.

For cell surface marker identification, single cell suspension of from trypsinized spheres was stained with anti-CD133, CD117 (c-Kit) or ABCG2 and secondary fluorescein (FITC)- or phycoerythrin (PE)-coupled antibodies (DAKO, Carpinteria, Calif.). OC-SLCs were fixed with 2% paraformaldehyde and analyzed by FACS Calibur apparatus (Becton Dickinson, San Diego, Calif.).

Radiation Treatment for Cell Viability Analysis

The Gamma Radiation (ionizing irradiation; IR) was delivered by Theratronic cobalt unit T-1000 (Theratronic International, Inc., Ottawa, Canada) at a dose rate of 1.1 Gy/min (SSD=57.5 cm). Cells were seeded on 24-well plates at a density of $2 \times 10^4$ cells/well in medium, after post-IR 24 hours, then followed and analyzed by the MTT assay (Sigma-Aldrich Co.). The amount of MTT formazon product was determined by measuring the absorbance at 560 nm (SpectraMax 250, Molecular Devices, Sunnyvale, Calif., USA).

Chemical Treatment for Cell Viability Analysis

Cells were seeded on 24-well plates at a density of $2 \times 10^4$ cells/well in medium, after post-chemical therapy 24 hours, then followed and analyzed by the MTT assay (Sigma-Aldrich Co.). The amount of MTT formazon product was determined by measuring the absorbance at 560 nm (SpectraMax 250, Molecular Devices, Sunnyvale, Calif., USA). The drugs for chemotherapy are consisted of visplatin, VP-16, doxorubicin, or paclitaxel.

In Vitro Cell Invasion Analysis and Soft Agar Assay

Each well (35 mm) of a six-well culture dish was coated with 2 ml bottom agar mixture (DMEM, 10% (v/v) FCS, 0.6% (w/v) agar). After the bottom layer had solidified, 2 ml top agar-medium mixture (DMEM, 10% (v/v) FCS, 0.3% (w/v) agar) containing $2 \times 10^4$ cells was added, and the dishes were incubated at 37° C. for 4 weeks. The plates were stained with 0.5 ml of 0.005% Crystal Violet for 1 hour, then the number of colonies was counted by a dissecting microscope.

Immunofluorescence Staining and Immunohistochemistry

The protocol followed is the one described in the previous study. Briefly, an avidin-biotin complex method was used for the immunofluorescence staining in the differentiated spheroid and neuronal-like cells. Each slide was treated with antibodies for CD133 (MACS, Miltenyi Biotec), GFAP (Chemicon), and MAP2 (Chemicon), phospho-ATM (Ser-1981; Upstate, Lake Placid, N.Y.) and BCL-2 (Chemicon). Immunoreactive signals were detected with a mixture of biotinylated rabbit antimouse IgG and Fluoesave (Calbiochem, La Jolla).

In Vivo Analysis of Tumor Growth and Metastasis

All procedures involving animals were in accordance with the institutional animal welfare guideline of Taipei Veterans General Hospital. $1 \times 10^4$ cancer-related stem cells, $1 \times 10^6$ non-cancer-related stem cells, and $5 \times 10^6$ cancer-related stem cells mixed with non-cancer-related stem cells were injected into the lung of SCID mice (BALB/c strain) each aged 8 weeks. In vivo GFP imaging was visualized and measured by an illuminating device (LT-9500 Illumatool TLS equipped with excitation illuminating source (470 nm) and filter plate (515 nm). The tumor size was measured by a caliper and the volume was calculated according to the formula: (Length× $Width^2$)/2. The integrated optical density of green fluorescence intensity was captured and then analyzed by Image Pro-plus software.

Statistical Analysis

The results are reported as mean±SD. Statistical analysis was performed using Student's-t test or the one-way or two-way ANOVA test followed by Turkey's test, as appropriate. A $p<0.05$ was considered to be statistically significant.

Result

Isolation and Cultivation of Stem Cells from Normal Tissues

Figure 3:
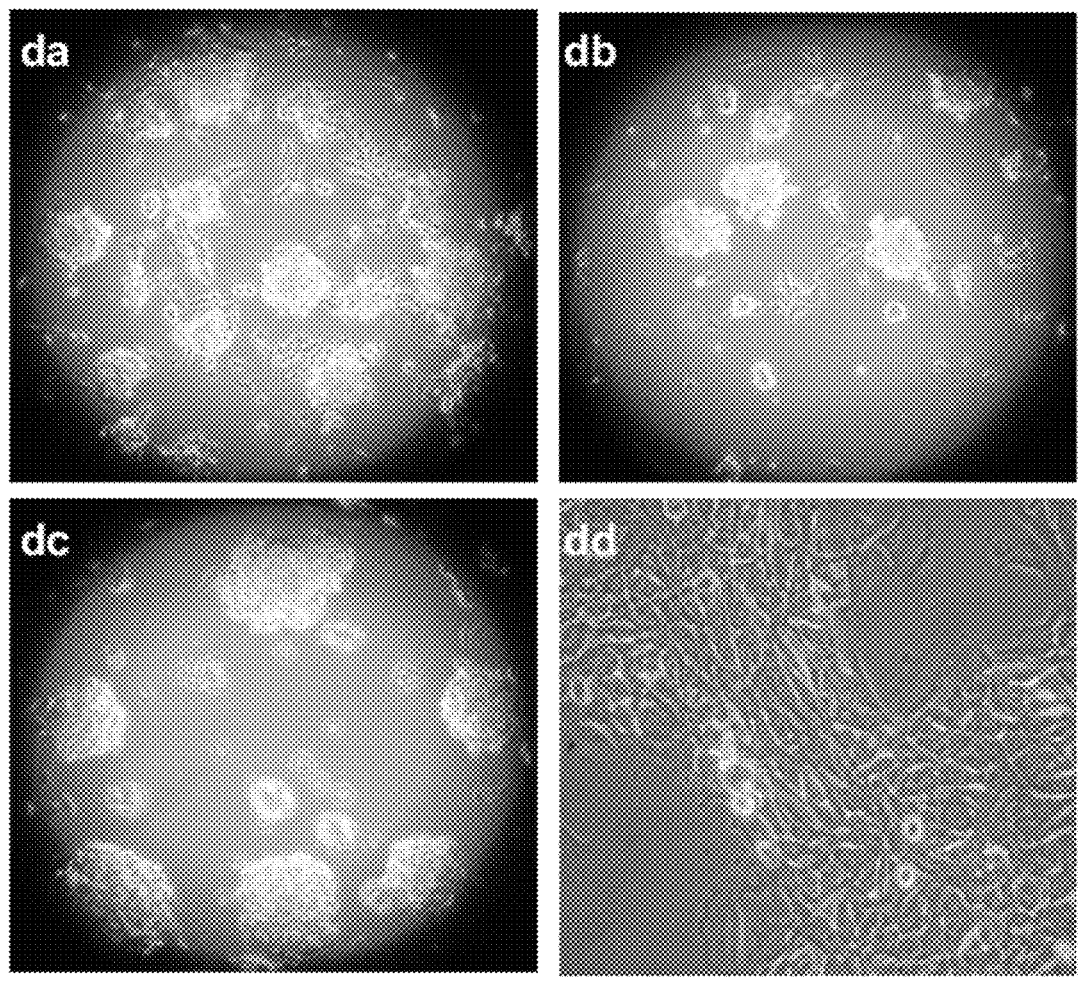
FIG. 3 shows the normal stem cells selected by making use of a device with a serum free medium of this invention. dd is control group, the cells not selected by the device cultured in the same condition.

The device illustrated in FIG. 2 was used to isolate stem cells from normal tissues. While spheroid cells is forming, putting them into freshly prepared Transwell®. Spheroid cells were penetrating through the outer membrane of wells, nylon mesh, porous thermoresponsive surface and final matri-gel layer by the characteristic of chemoattracting. In FIG. 3, dd, blank control group, is indicated cells cultured in the same condition and duration without being selected by the apparatus and the morphology of those cells is flat over the bottom of the culture plate. Obviously, the cells through screening demonstrated as spheroid cells.

Isolation Cancer-Related Stem Cells from Tumor Tissues

Figure 4A:
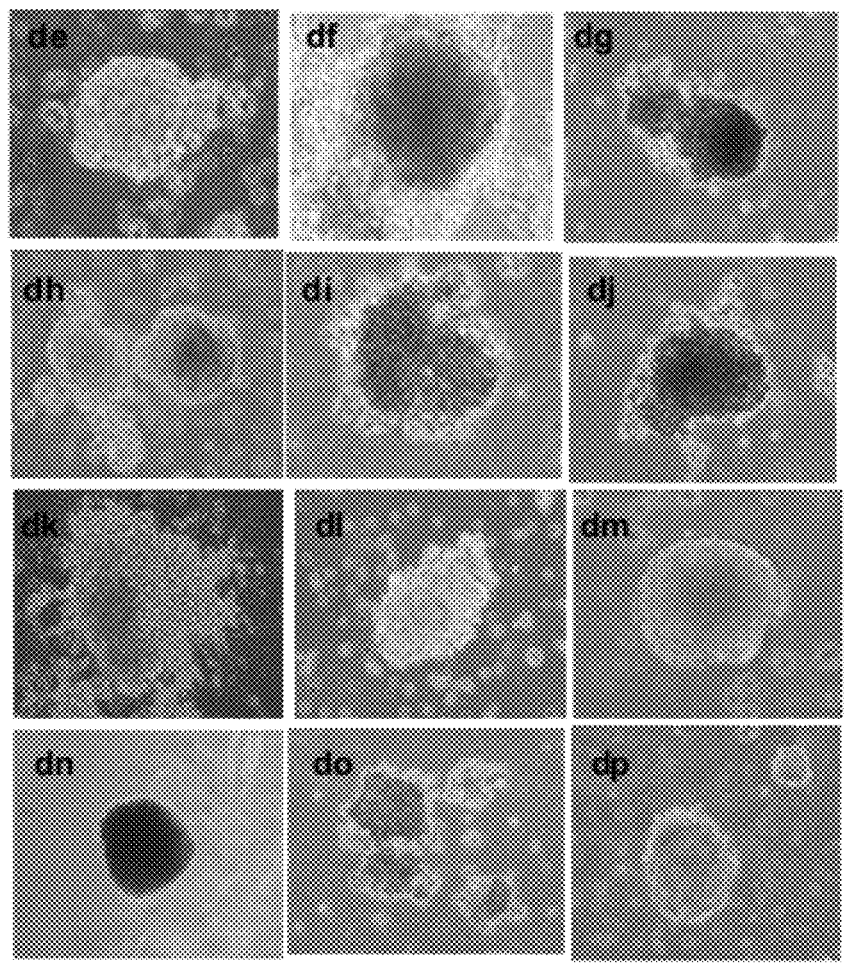
FIG. 4 depicts the formation of spheroid bodies isolated from different kinds of tumor tissues.
Figure 4B:
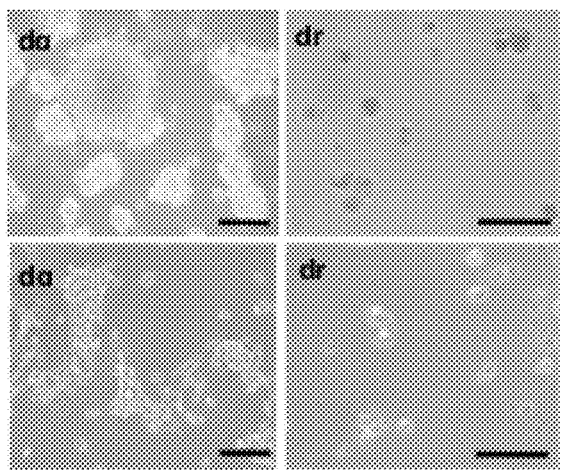
Figure 4C:
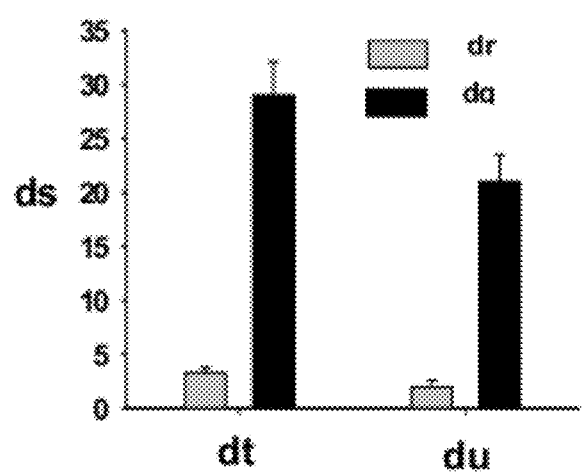

The transformation of spheroid cells from tumor cells derived from different carcinoma tissues illustrated in FIG. 4. FIG. 4 depicts the formation of spheroid bodies isolated from different kinds of tumor tissues. (a), the morphology of spheroid bodies. de is from brain tumor; df is from oral tumor; dg is from head and neck tumor; dh is from breast tumor; di is from stomach tumor; dj is from pancreas tumor; dk is from liver tumor; dl is from kidney tumor; dm is from bladder cancer; dn is from colon cancer; do is from prostate cancer; dp is from ovary cancer. (b), the morphology of stem cells collected from lung cancer. dq, cancer-related stem cells; dr, non-cancer-related stem cells. (c), the potency of forming spheroid bodies. dq, cancer-related stem cells; dr, non-cancer-related stem cells; ds, spheroid bodies per visual field; dt, parental cells no. 1; du, parental cells no. 2. All samples above could be observed the formation of spheroid cells. Our experiments further suggested that even from two different parent cell sources, there were no difference between cancer-related stem cells or non-cancer-related stem cells in the forming ability of spheroid cells (FIG. 4(c)).

The Expression Profile of Embryonic Stemness Genes

Figure 5A:
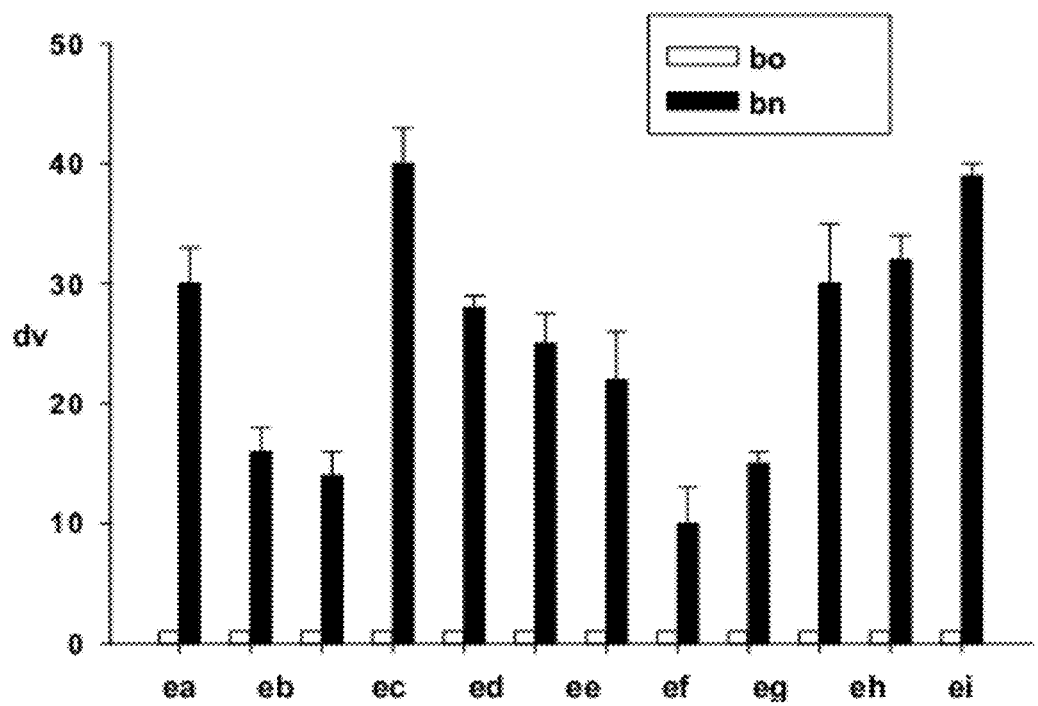
FIG. 5 demonstrates the expression profile of embryonic stemness gene.
Figure 5B:
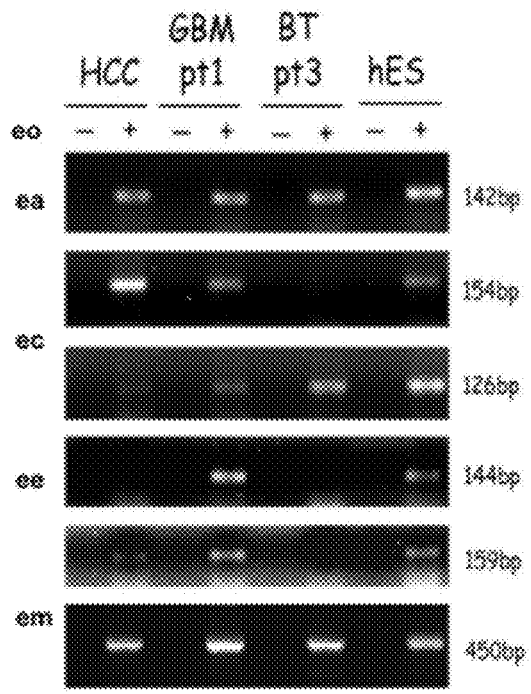

Expression of progenitor/stem cell genes such as Oct-4, Oct-4A, Nanog, nestin, Sox-2, Mushashi, C-Myc, beta-CAT, Bmil, MDR-1, MRP-1, ABCG2 and Klf4 was examined transcriptionally. FIG. 5 demonstrates the expression profile of embryonic stemness gene. (a) CD133 positive cells or CD133 negative cells was detected. (b) demonstrates the mRNA expression pattern. bn, CD133(+) cells; bo, CD133(−) cells; dv, the relative expression level of mRNA; ea, Oct-4; eb, Oct-4A; ec, Nanog; ed, nestin; ee, Sox-2; ef, Mushashi; eg, C-Myc; eh, beta-CAT; ei, Bmil; ej, MDR-1; ek, MRP-1; el, ABCG2; em, Klf4; en, GAPDH; eo, combination with or without radiation; HCC; pt1, parental cells no. 1; pt3, parental cells no. 3; hES, human embryonic stem cells; GBM; BT.

Presently, CD133 is known as a molecular marker of stem cell. The data showed that the expression patterns of stemness genes of CD133 positive cells were all elevated.

Characterization of Progenitor/Stem Cell Properties in Isolated Cells

Figure 6A:
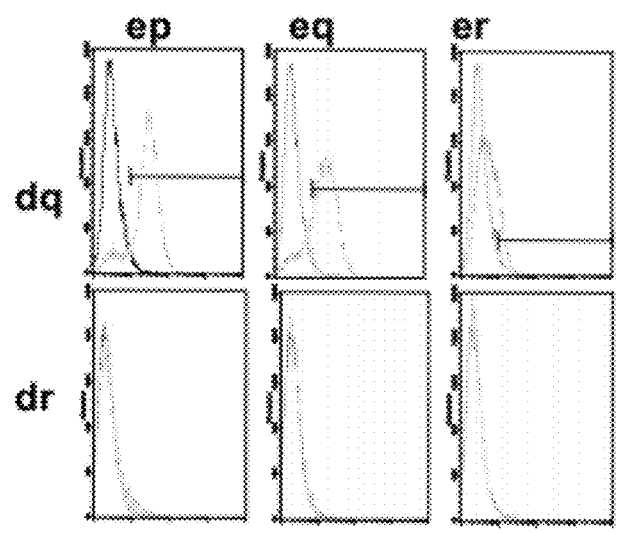
FIG. 6 shows the expression profile of specific molecular markers or surface markers by using the assay of flow cytometry.
Figure 6B:
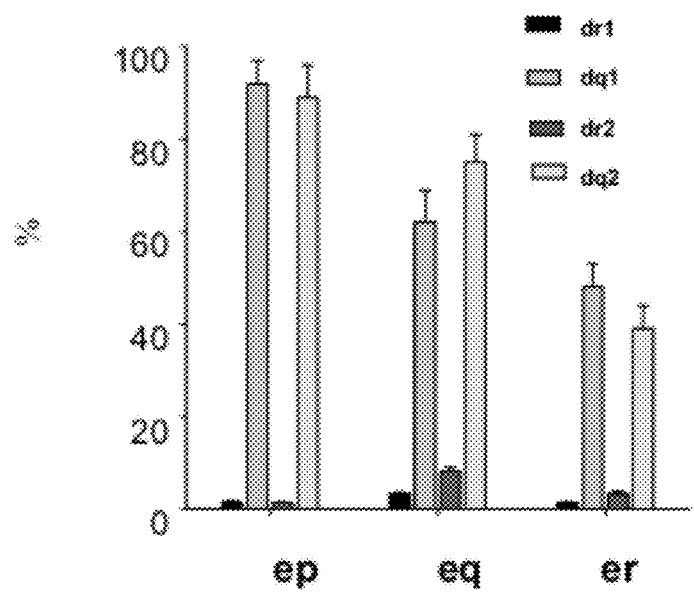
Figure 6C:
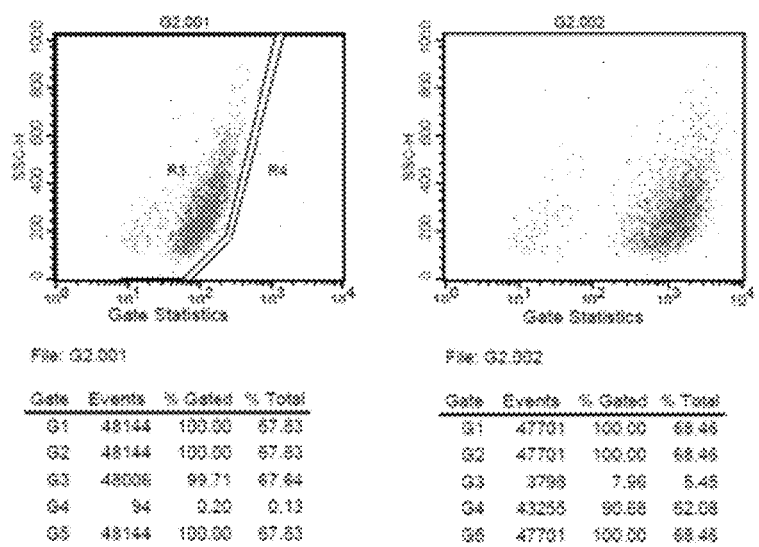
Figure 6D:
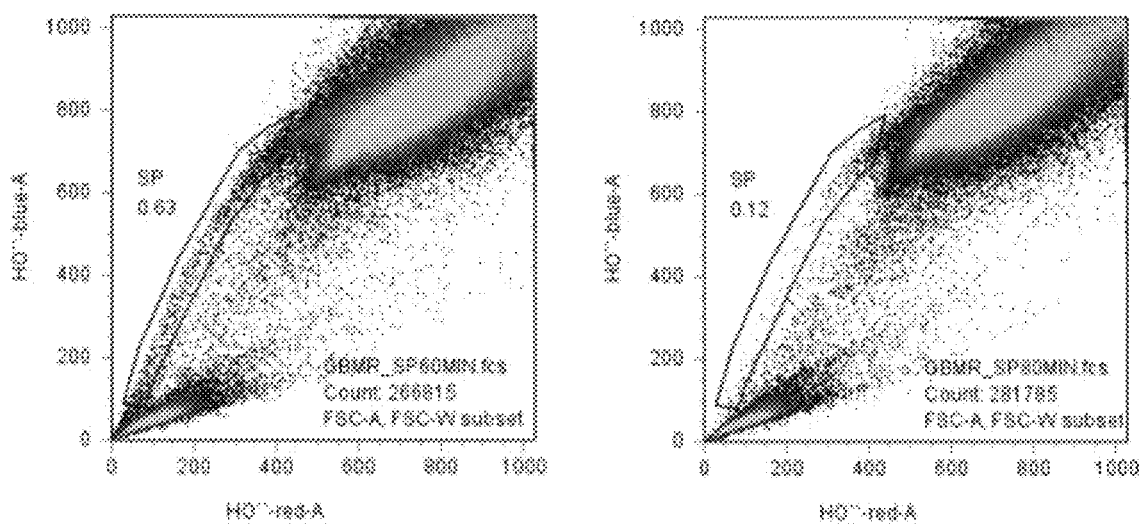

To further ascertain the properties of progenitor cells/stem cells primarily activated, we applied the flow cytometry to detect cellular surface markers. As shown in FIG. 6(a), some surface markers, like CD133, ABCG2 and CD117(c-Kit), expressed by cancer-related stem cells. However, CD133 and CD117 were two surface molecules recognized as the markers of non-cancer or cancer-related stem cells. Interestingly, cancer-related stem cells isolated by the device were also expressing ABCG2. Even selected from different parental cellular sources, the trend was the same (see FIG. 6(b)). Besides, expression of ALDH and the presence of side population were correlated with the production of cancer-related stem cells. FIG. 6 shows the expression profile of specific molecular markers or surface markers by using the assay of flow cytometry. (a) SB and/or stem-like cells from normal tissues of tumors were stained positively for stem cell markers (CD133 and CD117), and ATPase transporter (ABCG2) detected and analyzed by FACS analysis. (b) The individual percentage of the two cell surface markers-CD133 and ABCG2 was similarly consistent by FACS analysis suggesting that our isolated SB and/or stem-like cells from normal tissues of tumors mirrored the similarity of normal stem cell or cancer-related stem cells isolated from other solid tumor cells. (c) The detection of Aldehyde dehydrogenase (ALDH) of SB and/or stem-like cells by using FACS. (d) The higher percentage of subset of "Side Population" was also detected in SB and/or stem-like cells from normal tissues of tumors, which isolated and enriched by using this novel system. dq, cancer-related stem cells; dr, non-cancer-related stem cells; ep, detection of CD133 expression; eq, detection of ABCG2; er, detection of CD117; es, the numbers of positive cells; dr1, non-cancer-related stem cells from patient no. 1; dq1, cancer-related stem cells from patient no. 1; dr2, non-cancer-related stem cells from patient no. 2; dq2, cancer-related stem cells from patient no. 2.

Enhanced Tumorigenicity of Isolated Cancer-Related Stem Cells by In Vitro Invasion and Soft Agar Foci Formation Assay.

To evaluate the enhancement of tumorigenicity of isolated cancer-related stem cells, in vitro matrigel combined Transwell® invasion and soft agar colony formation assays were examined. FIG. 7 shows the evaluation of in vitro Tumorigenecity of stem cell derived from cancer. (a) To further evaluate the enhancement of tumorigenicity of isolated stem-like cells from malignant cancers, we examined in vitro Matrigel-combined Transwell® invasion and soft agar colony formation assays. (b) Compared with non-stem-like cells, stem-like cells derived from malignant cancers showed higher invasion activity through Matrigel Transwell invasion assay (left panel, $p<0.001$). In addition, the foci formation ability of stem-like cells derived from malignant cancers were enhanced when compared with the non-stem-like cells derived from malignant cancers (right, panel, $p<0.001$). dr, non-cancer-related stem cells; dq, cancer-related stem cells; et, cell numbers; eu, the amount of colonies; pt1, from parental cells no. 1; pt2, from parental cells no. 2.

Figure 7A:
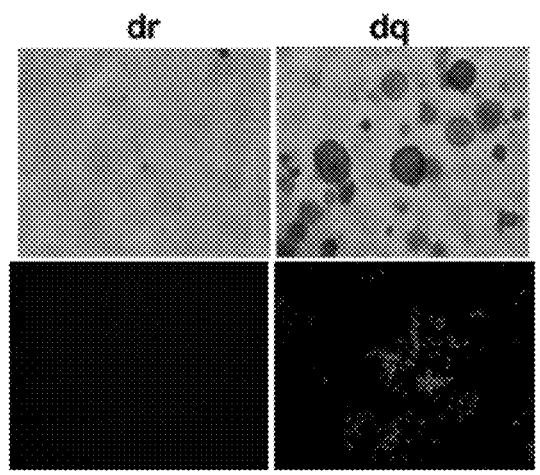
FIG. 7 shows the evaluation of in vitro Tumorigenecity of stem cell derived from cancer.
Figure 7B:
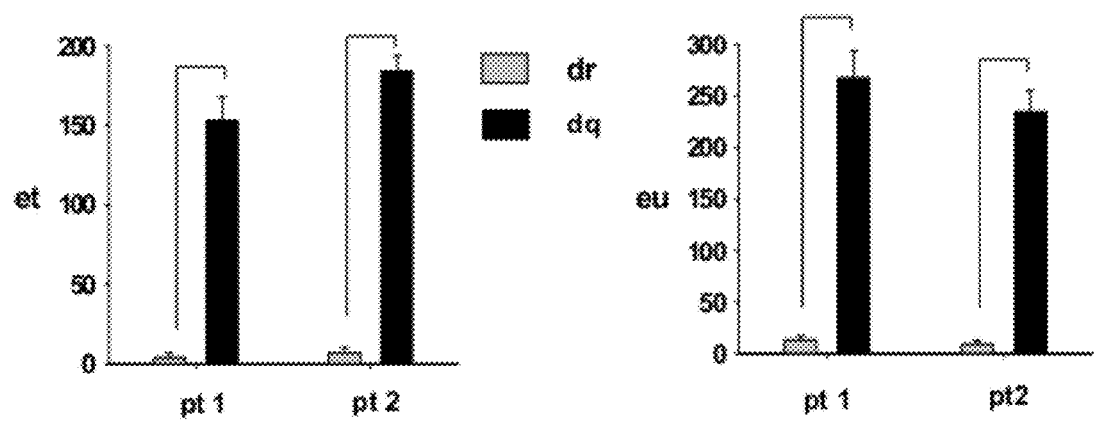

Substantially, the isolated cancer-related stem cells showed higher invasion activity through matrigel Transwell invasion assay (FIG. 7(a), $p<0.05$). Similarly, the foci formation ability of the cancer-related stem cells was enhanced when compared to that of the parental cells. Interestingly, while being plated with the same cell number during the foci formation assay, parental cells from different sources showed similar colony formation ability.

Elevated In Vivo Tumorigenicity

Figure 8A:
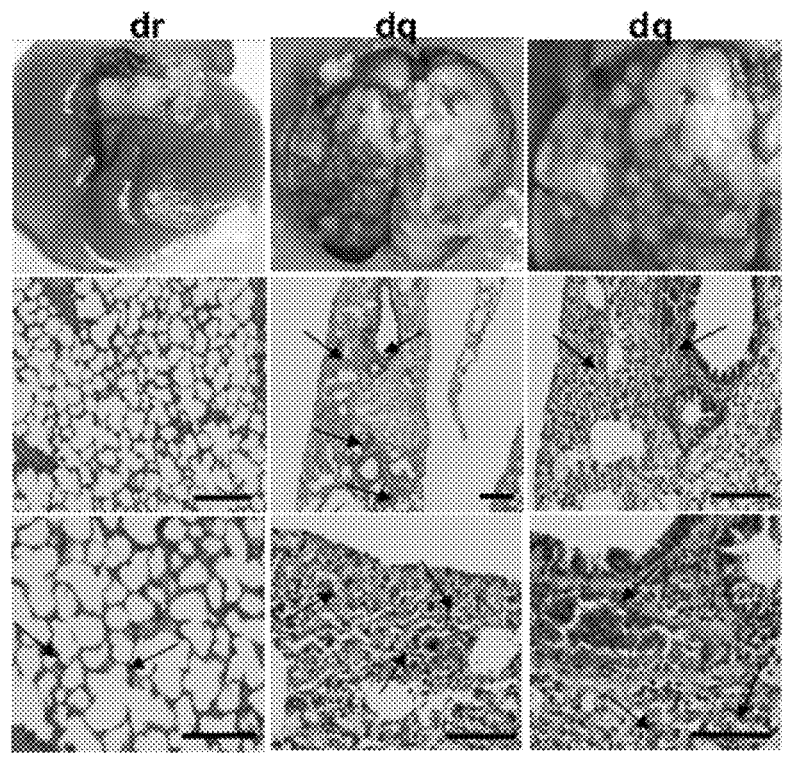
FIG. 8 is the evaluation of in vivo tumor formation ability—xenotransplantation tumoriassy.
Figure 8B:
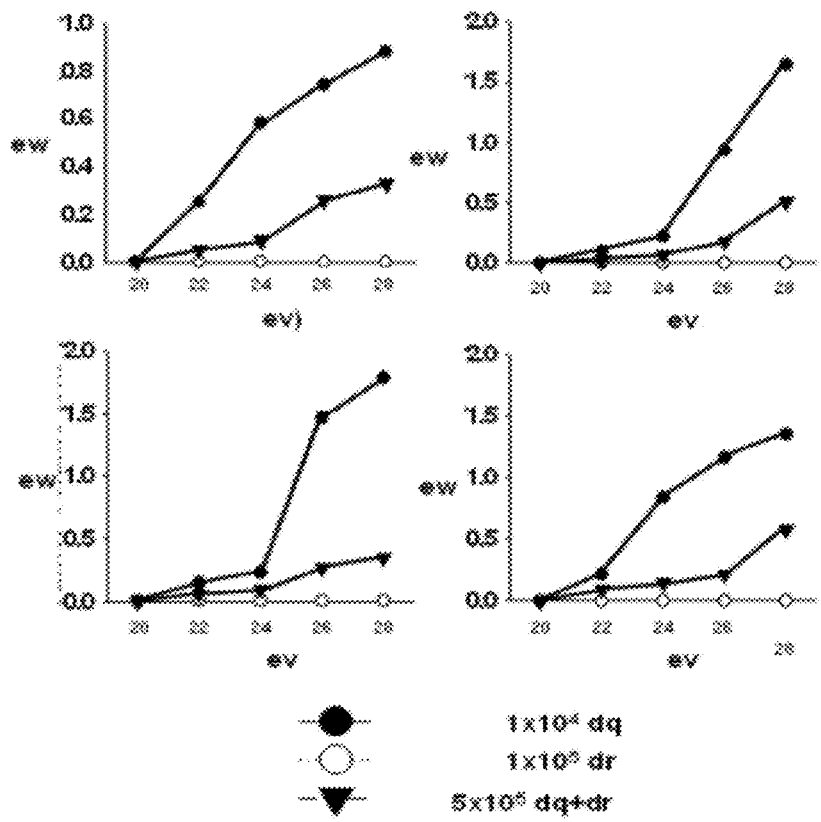

In order to further confirm the enriched tumor-initiating abilities of cancer-related stem cells isolated in vivo, the parental non-cancer-related stem cells and cancer-related stem cells-were injected into nude mice for transplanted tumorigenicity analysis. The morphologies of mice's lung were investigated and shown in FIG. 8(a), the foci formation ability of transplanted group were higher than other groups. However, we also detected the tumor volume of transplanted mice. Related data was shown in FIG. 8(b). Cancer-related stem cells generated tumor when only $1\times10^4$ cells were injected into mice. Compared with $1\times10^6$ cells non-cancer-related stem cells-transplanted or $5\times10^6$ unselected cells-transplanted mice, the data suggested that cancer-related stem cells were enriched for tumor-initiating cells by at least 100-fold. Moreover, even non-cancer-related stem cells were also extracted from tumor tissues. There was no focus formed in non-cancer-related stem cells-transplanted mice till 28 days. FIG. 8 is the evaluation of in vivo tumor formation ability-xenotransplantation tumoriassy. We further evaluated the in vivo tumor-restoration and proliferative ability of cancer stem-like cells and non-cancer stem-like cells by xenotransplanted tumorigenicity analysis. (a) Four weeks after $10^4$ cells were injected into the tail veins of SCID mice, a significant increase in the multiple nodules of tumor formation on lung surface was noted in the cancer stem-like cells-injected group but not in the non-cancer-related stem cell group. Diffuse infiltrations of cancer stem-like cells from the lung parenchyma to the alveolar cavity were observed. The histological examination demonstrated that the prominent neovascularization and thrombus formation were detected in the pulmonary parenchyma of cancer stem-like cells-injected SCID mice. In contrast, no significant tumor foci or neovascular formation was found in the lungs of non-cancer-related stem cell-injected SCID mice. We further investigated the in vivo tumor growth rate in $10^4$ cancer stem-like cells, $10^6$ non-cancer-related stem cells, and $5\times10^6$ parent tumor cells from the same patient. The finding demonstrated that the tumor growth rate of the $10^4$ cancer stem-like cells group was significantly higher than that of the $10^6$ non-cancer-related stem cells group and $5\times10^6$ parental tumor cell group (FIG. 8(b)). dr, non-cancer-related stem cells; dq, cancer-related stem cells; ev, time (days); ew, tumor volume (cm3).

Enhanced the Resistance of Radio/Chemotherapy

The property of resistance to irradiation treatment and chemotherapy is the major clinical criterion to characterize "cancer-related stem cells (CSCs)". The multidrug (chemotherapy)-resistant abilities of cancer-related stem cells and non-cancer-related stem cells was determined. We further tested four common chemotherapeutic agents including cisplatin, VP16 (etoposide), doxorubicin, paclitaxel. Compared with non-cancer-related stem cell, cancer-related stem cell are significantly resistant to the four tested chemotherapeutic agents (p<0.01).

Figure 9A:
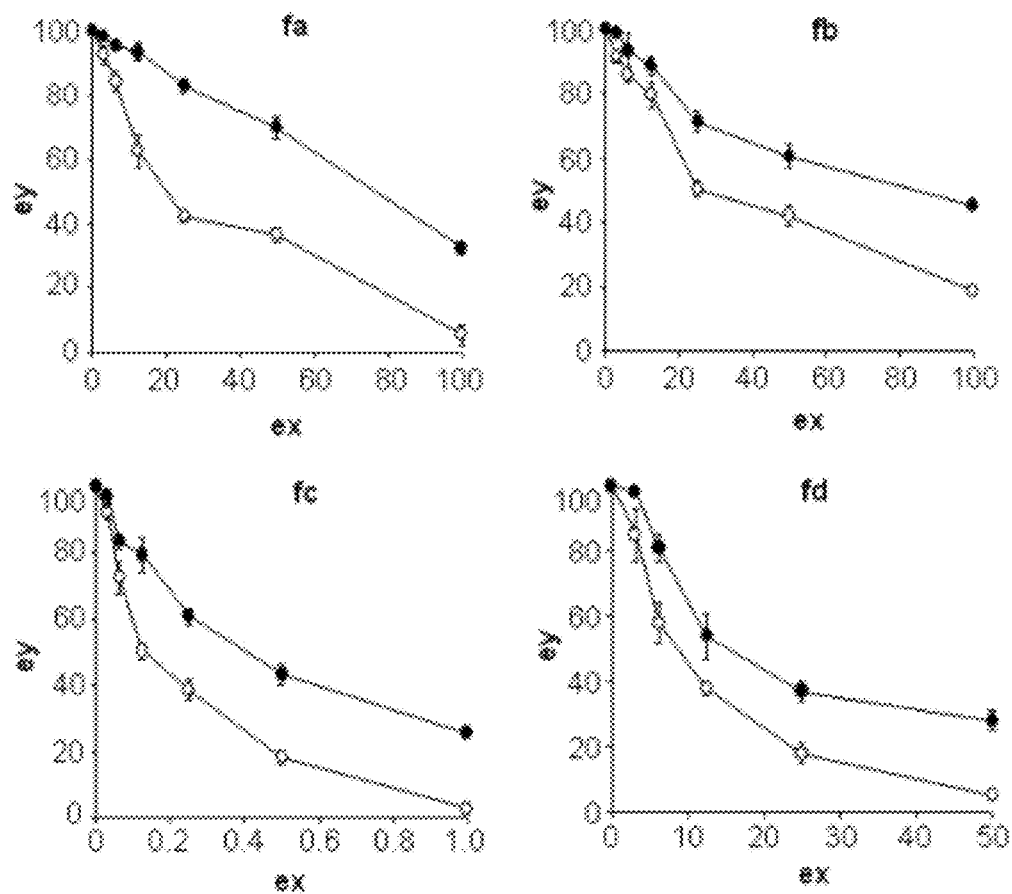
FIG. 9 depicts the property of resistance to irradiation treatment and chemotherapy is the major clinical criterion to characterize "cancer-related stem cells (CSCs)".
Figure 9B:
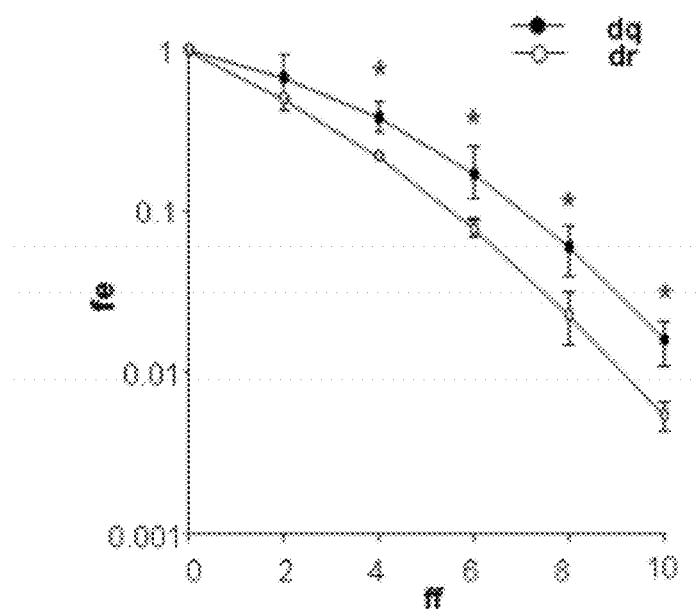

FIG. 9 depicts the property of resistance to irradiation treatment and chemotherapy is the major clinical criterion to characterize "cancer-related stem cells (CSCs)". (a) The multidrug (chemotherapy)-resistant abilities of cancer-related stem cell and non-cancer-related stem cell was determined. We further tested four common chemotherapeutic agents including cisplatin, VP16 (etoposide), doxorubicin, paclitaxel. Compared with non-cancer-related stem cell, cancer-related stem cell are significantly resistant to the four tested chemotherapeutic agents (p<0.01).

(b) To further determine the radiation effect on the rate of tumor growth, we used an ionizing radiation (IR) dose from 0 to 10 Gy to treat both cancer-related stem cell and non-cancer-related stem cell. As shown in FIG. B. after IR treatment, the survival rate and number of non-cancer-related stem cell were significantly higher than those of non-cancer-related stem cell (p<0.01). We further found that the cancer-related stem cell possess a higher degree of radioresistance (p<0.01; (b)). Moreover, we investigated the combined treatment effect of radiochemotherapy in cancer-related stem cell. Experiments were conducted with cisplatin (10 μM) alone, VP-16 (10 μM) alone, or combined cisplatin and VP-16 on IR (2 Gy)-treated LC-CD133$^+$. fa, cisplatin; fb, VP-16; fc, Doxorubicin; fd, paclitaxel; fe, survival fraction; ff, radiation dose (Grey); ex, concentration (μM); ey, survival fraction (%); ez, concentration (nM).

Example 3

Resveratrol (RV) Treatment Increased Radiosensitivity and Prolonged the Survival of CSCs Xenotransplanted Treated Group Isolation of CD133$^+$ Cell Subsets from AT/RT Tissues This research followed the tenets of the Declaration of Helsinki and all samples were obtained after patients had given informed consent. Dissociated cells from the samples of brain tumors from AT/RT patients were labeled with 1 ml CD133/1 micromagnetic beads per million cells using a CD133 cell isolation kit (MACS, Miltenyi Biotec). CD133$^+$ cells were cultured in serum-free DMEM/F12 (GIBCO) medium supplemented with N2 supplement (R&D), 10 ng/ml human recombinant bFGF (R&D) and 10 ng/ml EGF. Gamma radiation was delivered by a Theratronic cobalt unit T-1000 (Theratronic Internation, Inc., Ottawa, Canada) at a dose rate of 1.1 Gy/min (SSD=57.5 cm). For evaluation of cell proliferation, cells were seeded on 24-well plates at a density of $2 \times 10^4$ cells/well in medium, followed by the methyl thiazol tetrazolium assay (MTT assay; Sigma-Aldrich Co.). The amount of MTT formazan product was determined using a microplate reader and an absorbance of 560 nm (SpectraMax 250, Molecular Devices, Sunnyvale, Calif., USA).

Real-Time RT-PCR

Real-time RT-PCR was performed as previously described. Briefly, total RNA (1 μg) of each sample was reverse-transcribed in a 20 μl volume using 0.5 μg oligo dT and 200 U Superscript II RT (Invitrogen, Carlsbad, Calif.). The primer sequences used for real-time RT-PCR are shown in Table 1. The amplification was carried out in a total volume of 20 μl containing 0.5 μM of each primer, 4 mM MgCl$_2$, 2 μl LightCycler™-FastStart DNA Master SYBR green I (Roche Molecular Systems, Alameda, Calif.) and 2 μl of 1:10 diluted cDNA. PCR reactions were prepared in duplicate and heated to 95° C. for 10 minutes followed by 40 cycles of denaturation at 95° C. for 10 seconds, annealing at 55° C. for 5 seconds, and extension at 72° C. for 20 seconds. Standard curves (cycle threshold values versus template concentration) were prepared for each target gene and for the endogenous reference (GAPDH) in each sample. Quantification of unknown samples was performed using LightCycler Relative Quantification Software version 3.3 (Roche Molecular Systems, Alameda, Calif.).

TABLE 1

The primer sequences used for real-time RT-PCR in example 3

| Gene | Accession No. | Sequences (5' to 3') | Product size (in bp) | Tm (° C.) |
|---|---|---|---|---|
| Oct-4 | NM_002701 | F: ACCGAGTGAGAGGCAACC<br>R: TGAGAAAGGAGACCCAGCAG | 133 | 55 |
| Oct-4A | NM_002701 | F: GTGGAGAGCAACTCCGATG<br>R: TGCTCCAGCTTCTCCTTCTC | 86 | 60 |
| SOX-2 | NM_003106 | F: CGAGTGGAAACTTTTGTCGGA<br>R: TGTGCAGCGCTCGCAG | 74 | 60 |
| Nanog | NM_024865 | F: ATTCAGGACAGCCCTGATTCTTC<br>R: TTTTTGCGACACTCTTCTCTGC | 76 | 60 |
| Nestin | NM_006617 | F: AGGAGGAGTTGGGTTCTG<br>R: GGAGTGGAGTCTGGAAGG | 112 | 50 |
| Musashi | NM_002442 | F: TCCCTCGGCGAGCACA<br>R: GACAGCCCCCCCACAAA | 64 | 60 |
| Myc | NM_002467 | F: GGAACGAGCTAAAACGGAGCT<br>R: GGCCTTTTCATTGTTTTCCAACT | 71 | 60 |
| MDR-1 | NM_000927 | F: TGGCAAAGAAATAAAGCGACTGA<br>R: CAGGATGGGCTCCTGGG | 76 | 60 |
| MRP-1 | X60111 | F: GCTTCCTCTTGGTGATATTCG<br>R: GCAGTTCAACGCATAGTGG | 176 | 50 |

TABLE 1-continued

The primer sequences used for real-time RT-PCR in example 3

| Gene | Accession No. | Sequences (5' to 3') | Product size (in bp) | Tm (° C.) |
|---|---|---|---|---|
| ABCG2 | NM_004827 | F: CATGTACTGGCGAAGAATATTTGGT<br>R: CACGTGATTCTTCCACAAGCC | 74 | 60 |
| Bmi1 | NM_005180 | F: AAATGCTGGAGAACTGGAAAG<br>R: CTGTGGATGAGGAGACTGC | 124 | 50 |
| Beta-catenin | NM_001098209 | F: CCAGCCGACACCAAGAAG<br>R: CGAATCAATCCAACAGTAGCC | 130 | 50 |

In Vitro Cell Invasion Analysis and Soft Agar Assay

The 24-well plate Transwell® system with a polycarbonate filter membrane of 8-µm pore size (Corning, United Kingdom) was used. Cell suspensions were seeded in the upper compartment of the Transwell® chamber at a density of $1\times10^5$ cells in 100 µl serum-free medium. After 24 hours, the filter membrane was fixed in 4% formalin for 1 hour. The opposite surface of the filter membrane was stained with Hoechst 33342 for 3 min. The soft agar assay was performed as follows. The bottom of each well (35 mm) of a six-well culture dish was coated with 2 ml agar mixture (DMEM, 10% (v/v) FCS, 0.6% (w/v) agar). After the bottom layer solidified, 2 ml top agar-medium mixture (DMEM, 10% (v/v) FCS, 0.3% (w/v) agar) containing $2\times10^4$ cells was added, and dishes were incubated at 37° C. for 4 weeks. The plates were stained with 0.5 ml 0.005% Crystal Violet for 1 hour, and then the number of colonies was counted using a microscope.

Enzyme-Linked Immunosorbent Assay (ELISA) and Terminal dUTP Nick-End Labeling (TUNEL) Assay The activities of caspases-8 and -3 were determined by ELISA kit (Medical & Biological Laboratories Co., Ltd, Nagoya, Japan) and quantified by reading at 490 nm (MRX; Dynatech Laboratories, Chantilly, Va., U.S.A.). Each individual sample was analyzed in triplicate. Furthermore, apoptotic cells were identified by the terminal dUTP nick-end labeling (TUNEL) method (In situ Cell Death Detection Kit, POD, Roche Boehringer Mannheim Corp., Ind., U.S.A.). Briefly, cells with cover slips were washed with 1× phosphate-buffered saline (PBS), fixed with 4% of paraformaldehyde for 10 min, permeabilized with 0.1% of Triton X-100 for 5 min, and incubated with the TUNEL reagent provided for 1 h. Chromogenic development was then applied using 3-amino-9-ethyl-carbazole, and slides were counterstained using H&E.

In Vivo Analysis of Tumor Growth and Metastasis

All procedures involving animals were in accordance with the institutional animal welfare guideline of Taipei Veterans General Hospital. $10^4$ CD133$^+$ and CD133$^-$ AT/RT cells were injected into the striatum of the brain of each SCID mouse (BALB/c strain); each mouse was 8 weeks of age. Tumor size was measured using calipers and the volume was calculated according to the formula: (length×width$^2$)/2 and then analyzed using Image Pro-plus software.

Statistical Analysis

The results are reported as mean±SD. Statistical analysis was performed using Student's-t test or a one-way or two-way ANOVA test followed by Turkey's test, as appropriate. P<0.05 was considered to be statistically significant.

Result

Isolation and Characterization of CD133-Positive Cells from AT/RT Tissues

Figure 10A:
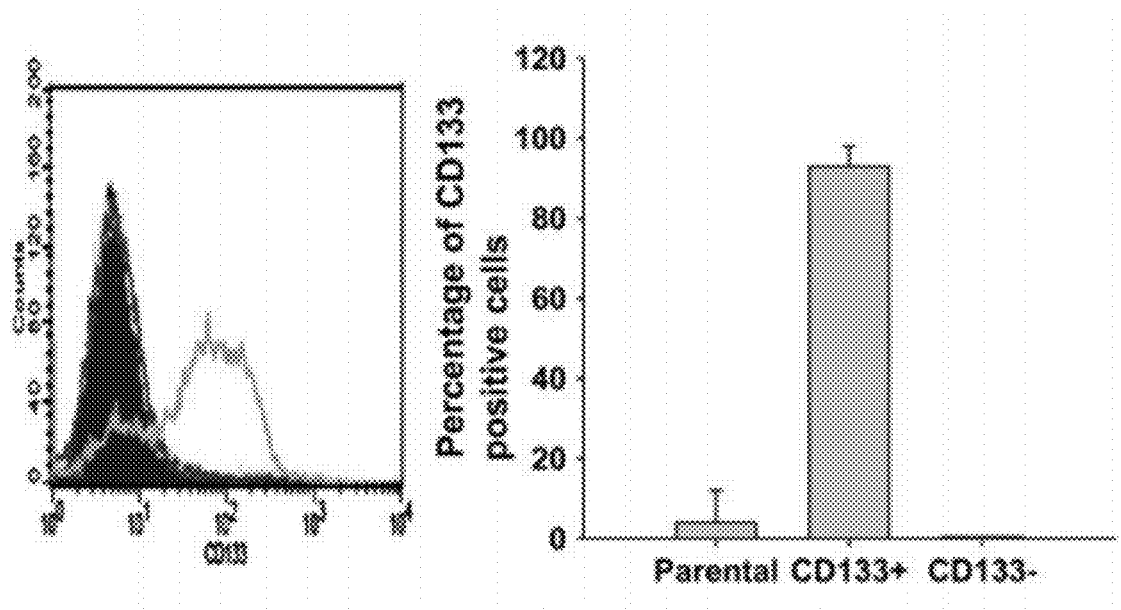
FIG. 10 shows the evaluation of cytotoxic effects of resveratrol (RV) in cancer-related stem cells (CSCs) cells.
Figure 10B:
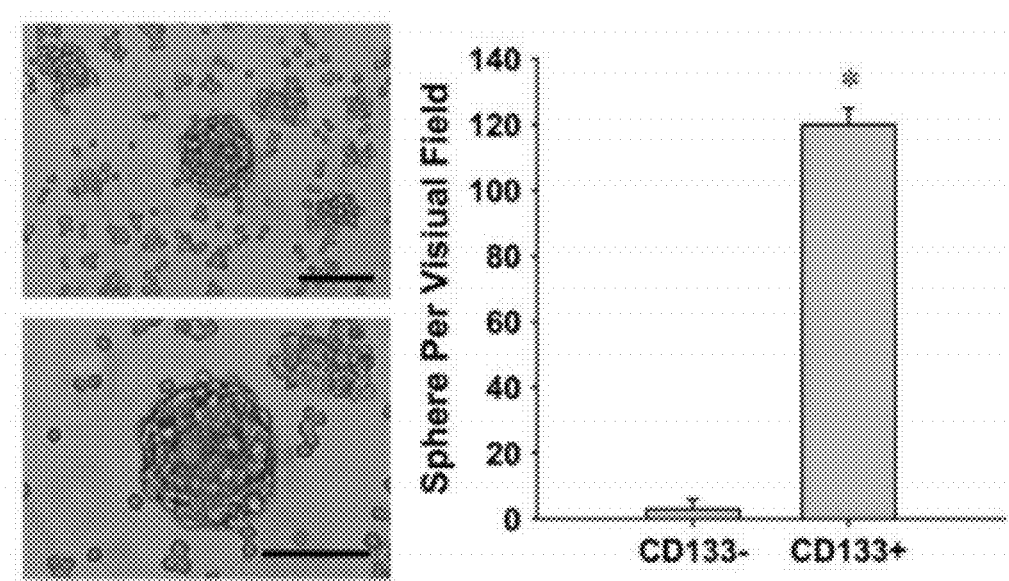
Figure 10C:
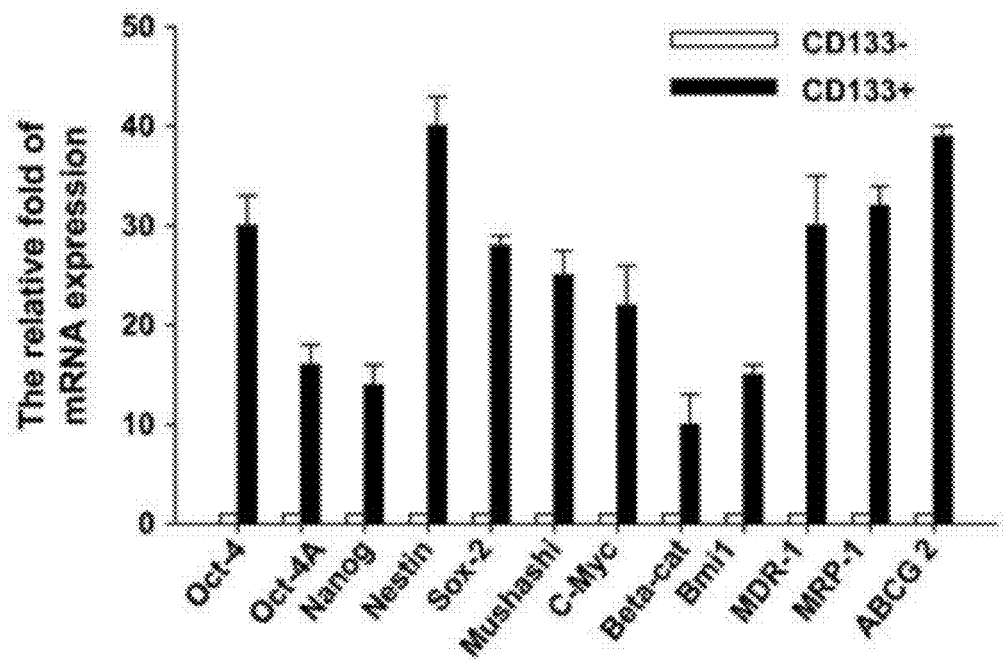
Figure 10D:
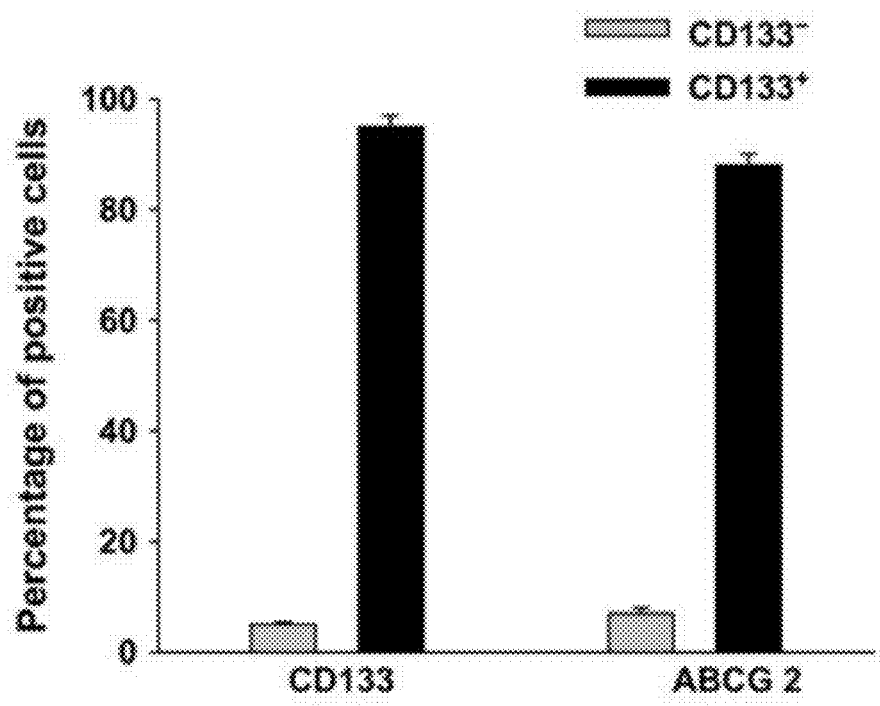

CD133$^+$ were isolated from tissue samples provided by the 5 AT/RT patients (FIG. 10A). It has been reported that cancer-related stem cells can be cultured in suspension to generate floating spheroid-like bodies (SB) and maintain the self-renewal capabilities in serum-free media with bFGF and EGF. It was found that CD133$^+$ isolated from these 5 AT/RT patients could stably proliferate to form SB in DF-12 serum-free medium with bFGF and EGF. In these 5 patients, Patient 5 showed the highest percentage of CD133$^+$ (36.4%) and the most robust in vivo tumorigenicity, and presented the properties of CSCs. The ability of Patient 5-derived CD133$^+$ to form SB was significantly greater than that of CD133$^-$ (FIG. 10B; p<0.05). Furthermore, quantitative real-time RT-PCR showed that the mRNA expression levels of stemness genes (Oct-4, Oct-4A, Nanog, Sox-2, Neestin, Mushashi, c-Myc, beta-catenin, and Bmi-1) and drug-resistant genes (MDR-1, MRP-1, and ABCG2) were upregulated in CD133$^+$ as compared with CD133$^-$ cells (FIG. 10C). The result of FACS scan showed that AT/RT-CD133$^+$ derived from SB under serum-free/bFGF/EGF medium could be stained positively for stem cell marker (CD133) in addition to the ATPase transporter (ABCG2) (FIG. 10D). The individual percentages of the two cell surface markers (CD133 and ABCG2) were also consistent with FACS data, suggesting that our isolated AT/RT-CD133$^+$ might be similar to cancer-related stem cells isolated from other solid tumor cells.

Evaluation of Cytotoxic Effects of Resveratrol in AT/RTCD133$^{+/-}$

Figure 11A:
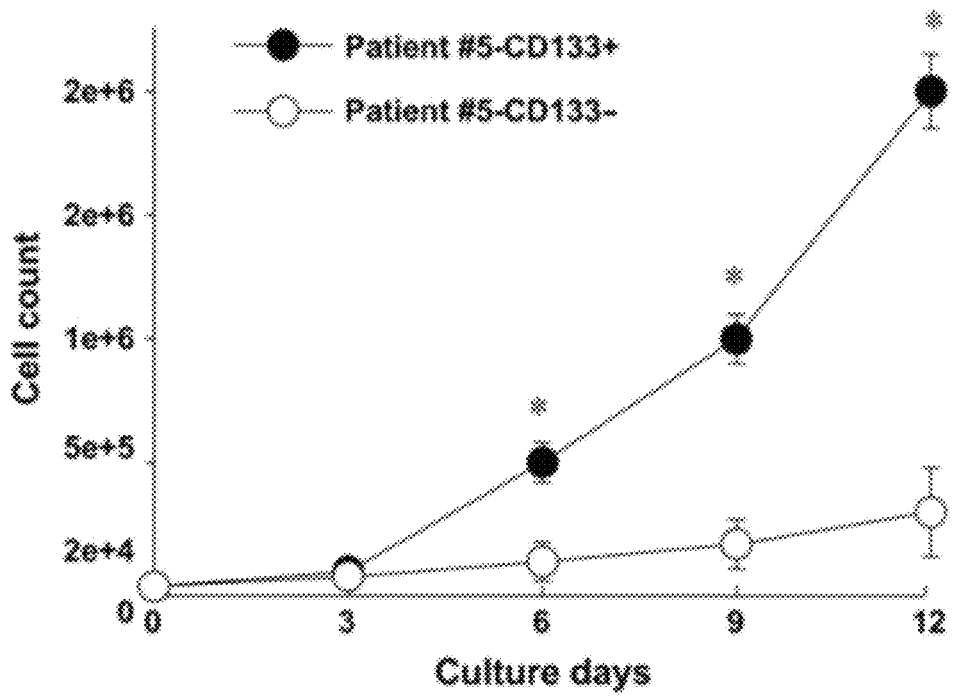
FIG. 11 is resveratrol increased radiosensitivity and apoptotic activity in cancer-related stem cells (CSCs), and inhibited cell growth of CSCs.
Figure 11B:
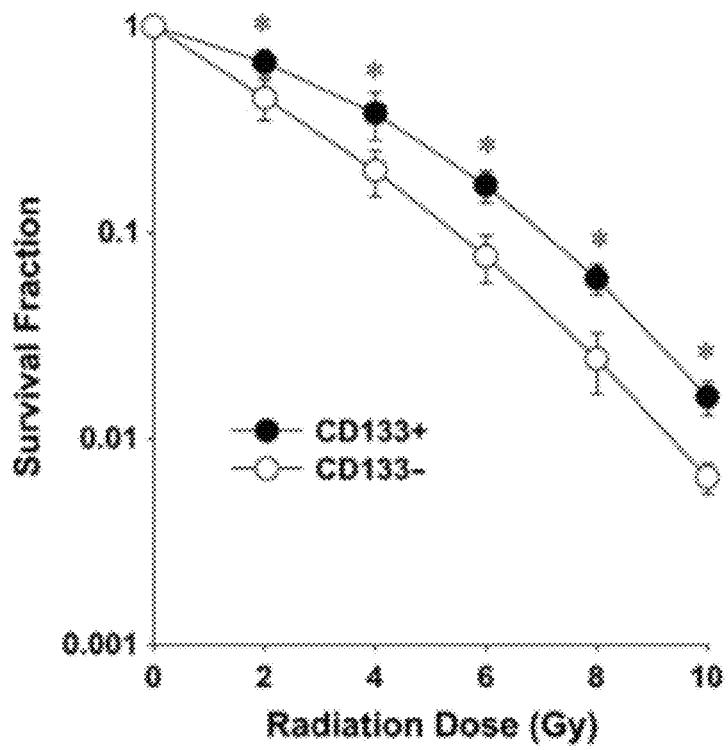
Figure 11C:
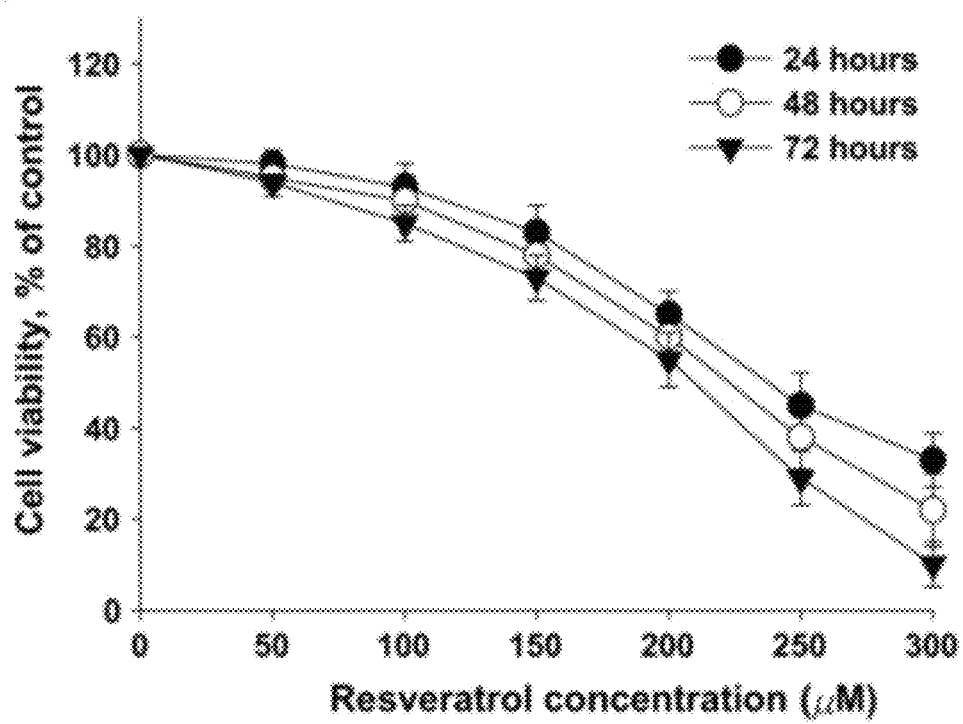
Figure 11D:
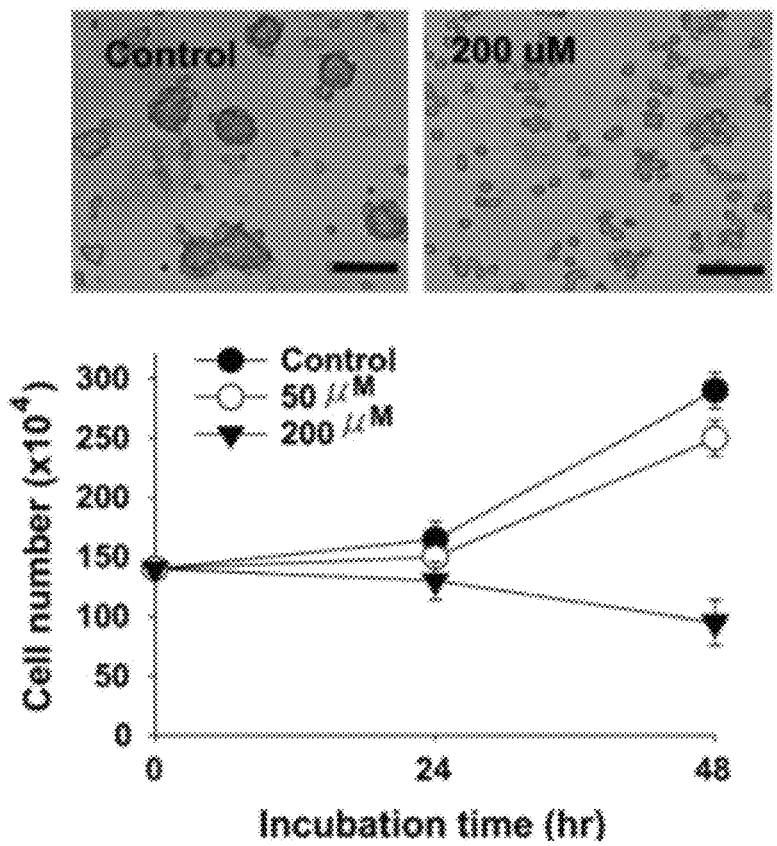

Our result showed that CD133$^+$ had a higher proliferation rate than CD133$^-$ as assessed by the MTT assay (p<0.05; FIG. 11A). By applying ionizing radiation (IR) dose from 0 to 10 Gy to the two groups of cells, the result further confirmed that CD133$^+$ show greater radioresistance than CD133$^-$ (FIG. 11B). RV has been recently suggested to inhibit tumor growth. However, it remains undetermined whether RV can inhibit the CSC properties of brain tumor-derived CD133$^+$ or AT/RT-CD133$^+$. To answer this question, AT/RT-CD133$^+$ were treated with different doses of RV and cell viability was analyzed using the MTT assay. As shown in FIG. 11C, AT/RT-CD133$^+$ were treated with RV at different concentrations (0, 10, 50, 100, 150, 200, 250, and 300 mM) for 24, 48, and 72 h. Cell viability was not significantly affected if the concentration of RV was lower than 50 mM (p>0.05; FIG. 11C). After 48 h treated with 200 mM RV, the spheroidlike CD133$^+$ detached from clusters and became a single suspension (FIG. 11D). The total number and growth rates of CD133$^+$ after treatment with 200 mM RV for 48 and 72 h were significantly decreased (p>0.05, FIG. 11D). Importantly, the xenotransplanted tumorigenicity analysis showed that 1,000 AT/RT-CD133$^+$, isolated from the 5 patient samples, treated with 200 mM RV for 72 h did not form tumors in transplanted SCID mice within 6 weeks after inoculation.

Figure 12A:
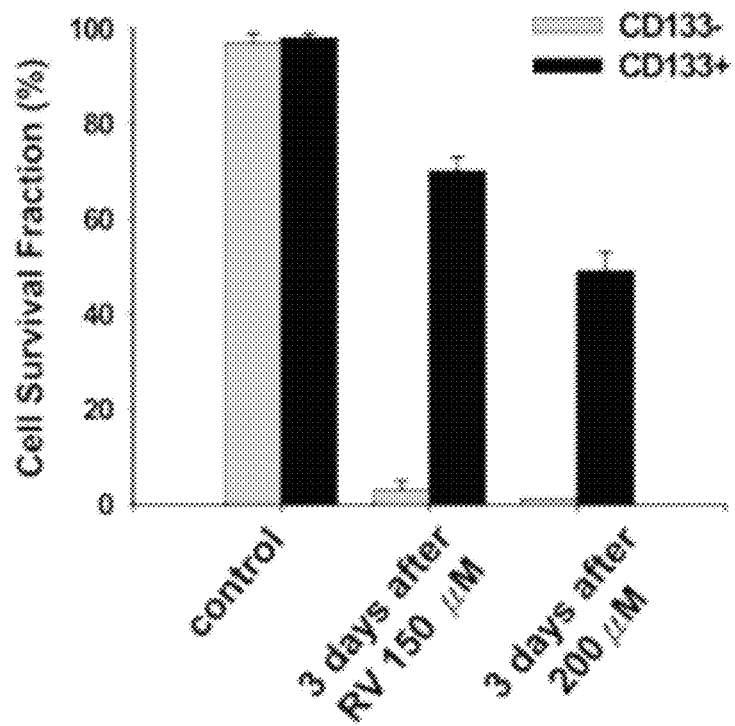
FIG. 12 is the CSCs derived from medulloblastoma (MB).
Figure 12B:
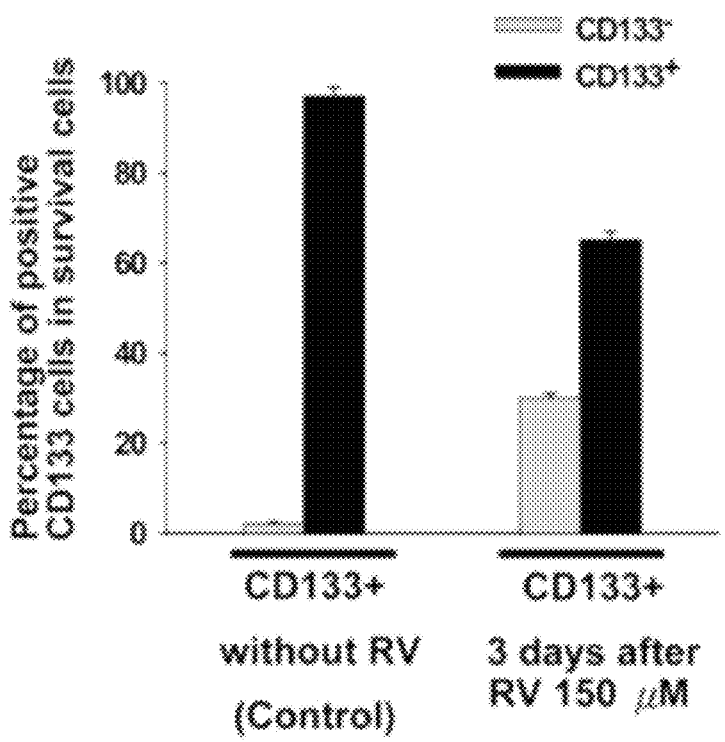
Figure 12C:
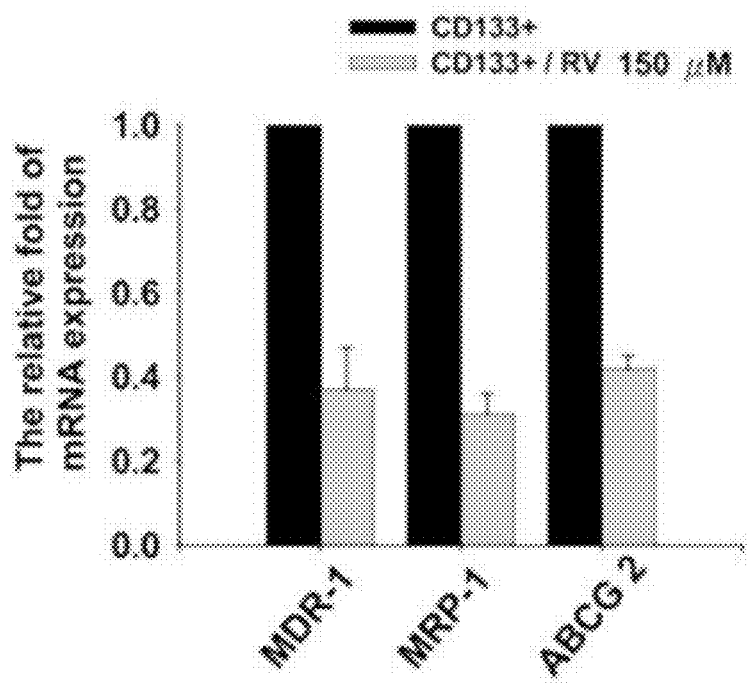

Investigation of Cytotoxic-Modulation Effects of 150 mMRV in AT/RT-CD133$^{+/-}$ In FIG. 11, it shown that 200 mM RV leads to a significant cytotoxic effect in treated AT/RT-CD133$^+$. To further investigate the role of RV in synergetic treatment for the clinical use of ATRT, the optimal concentration of RV for CD133$^{+/-}$ was further tested. Our data found that the viability of CD133$^+$ was reduced by 20-25% when the concentration of RV was 100 mM, and by about 40% when the concentration of RV was 150 mM for 72 h (FIG. 11A, 12A). Furthermore, the treatment of 150 mM RV for 72 h can totally block the proliferation and growth of CD133$^-$ (FIG. 12A). Importantly, we demonstrated that the treatment of 150 mMRV for 3 days can not only decrease the percentage of CD133-positive cells in ATRT-CD133$^+$, but also facilitate CD133$^+$ to differentiate into CD133$^-$ (FIG. 12B). In addition, 150 mM RV can further effectively inhibit the expression of drug-resistant genes (MDR-1, MRP-1, and ABCG2) in AT/RT-CD133$^+$ compared with CD133$^+$ without RV treatment (FIG. 12C).

Figure 12D:
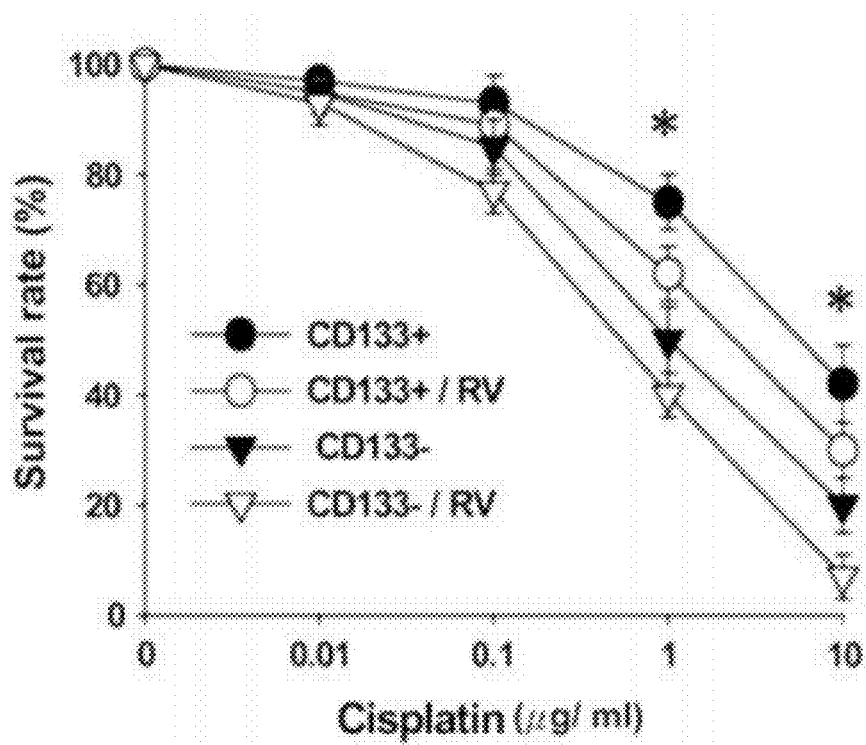
Figure 12E:
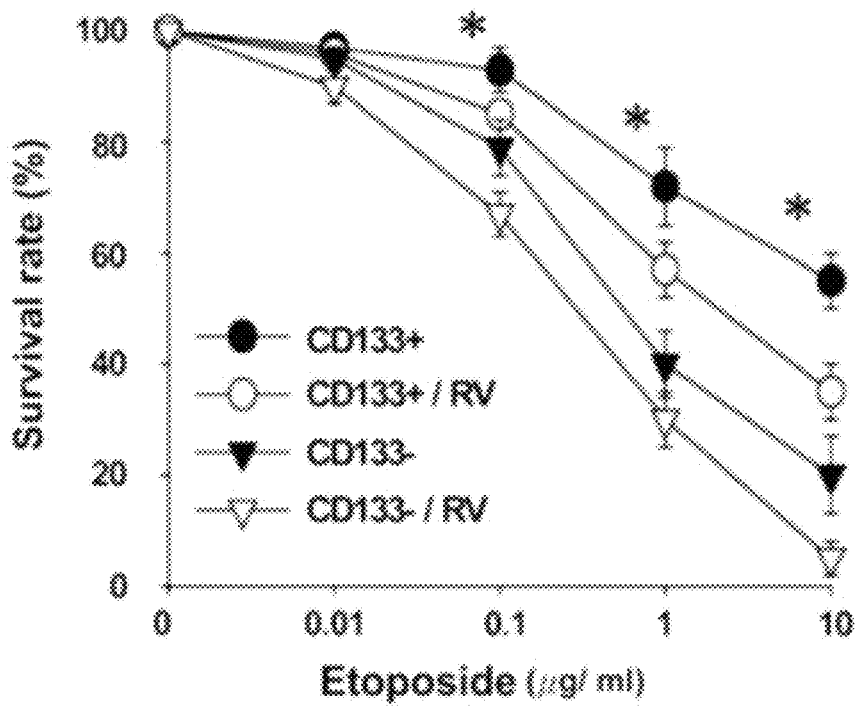
Figure 12F:
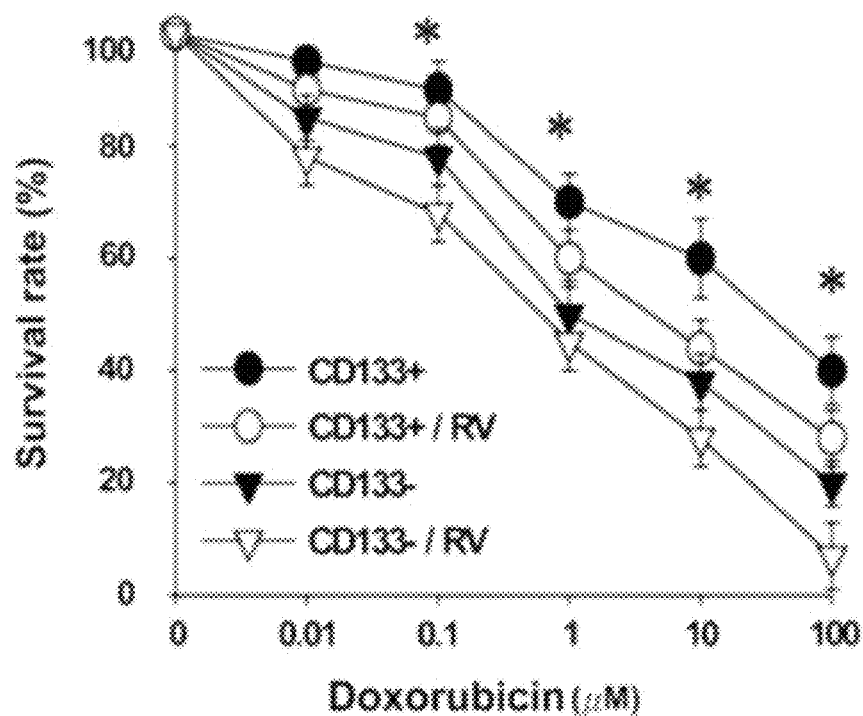
Figure 13A:
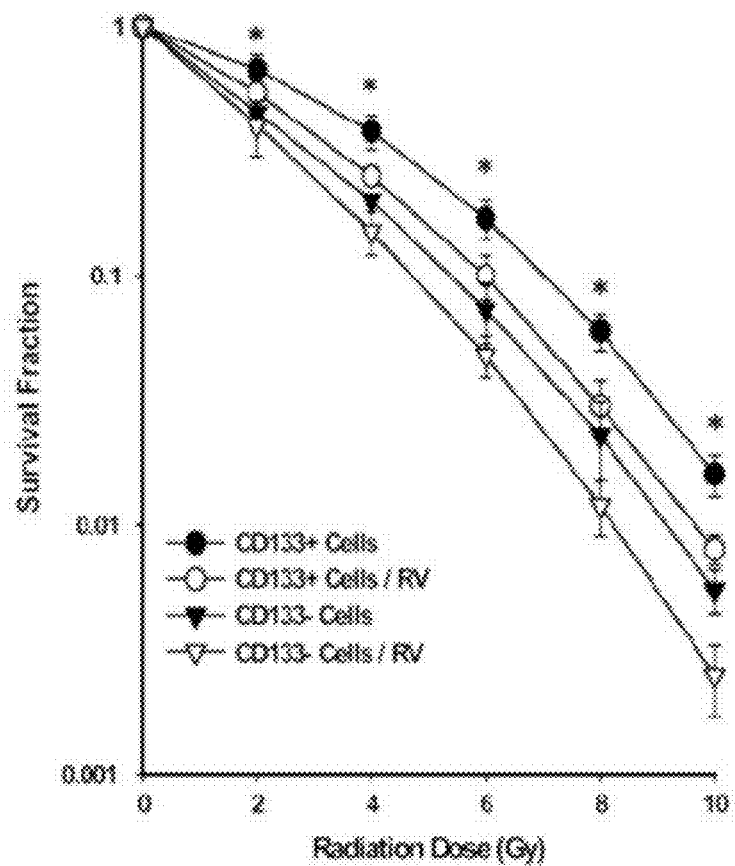
FIG. 13 is detection of the expression levels of stem cell markers in MB-CSCs and parental MB cells.
Figure 13B:
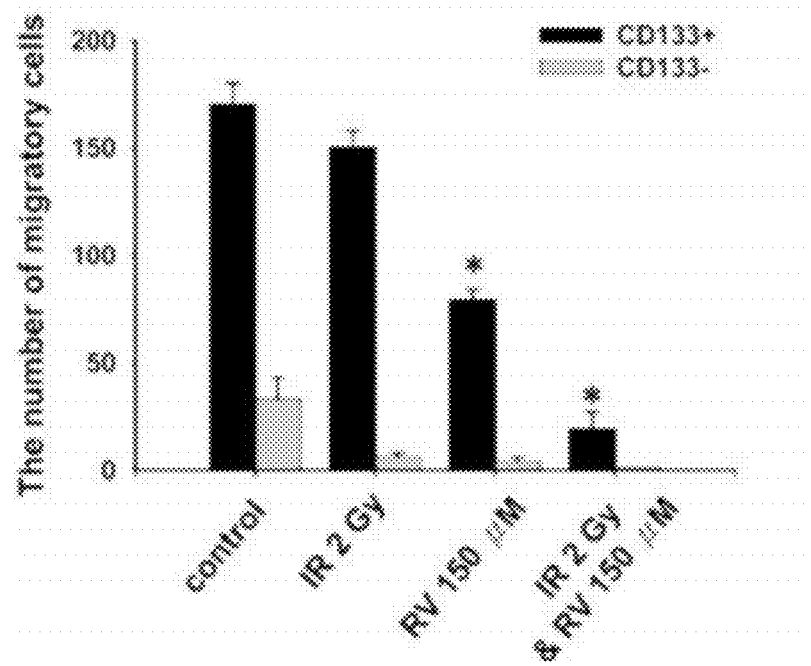
Figure 13C:
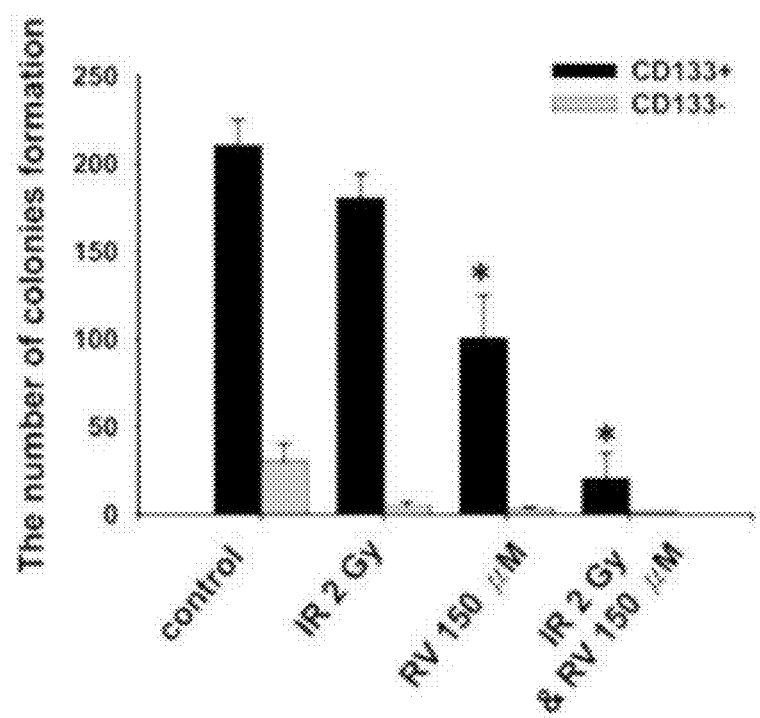

Enhanced Radiosensitivity of AT/RT-CD133$^{+/-}$ after Treatment with Resveratrol RV-mediated inhibition of AT/RT-CD133$^+$ growth and demonstration of CSC's properties led us to further investigate the role of RV (150 mM) as a sensitizer for chemotherapy and radiotherapy against CD133$^+$. First, we evaluated the chemosensitizing effects of RV in ATRTCD133$^{+/-}$, and of the three common chemotherapeutic agents used including cisplatin, VP-16 (etoposide), and doxorubicin. Compared with CD133$^-$, CD133$^+$ were significantly resistant to the three tested chemotherapeutic agents (p<0.01; FIG. 12D-F). The anti-cancer proliferation effect on ATRT-CD133$^{+/-}$ treated with single agent chemotherapy was significantly improved with the addition of 150 mM RV compared with cisplatin alone, VP-16 alone, and on AT/RT-CD133$^{+/-}$ was also significantly improved with the addition of RV-150 mM (p<0.01; FIG. 13A). Compared with IR treatment alone, migration/invasion (FIG. 13B) and tumor colony formation (FIG. 13C) showed the similar trend and were significantly inhibited in AT/RTCD133$^+$ treated with 150 mM RV alone or 150 mM RV combined with IR. These data provide evidence that the effectiveness of chemotherapy and radiation treatment for ATRT-CD133$^+$ can be improved with RV treatment.

Figure 14A:
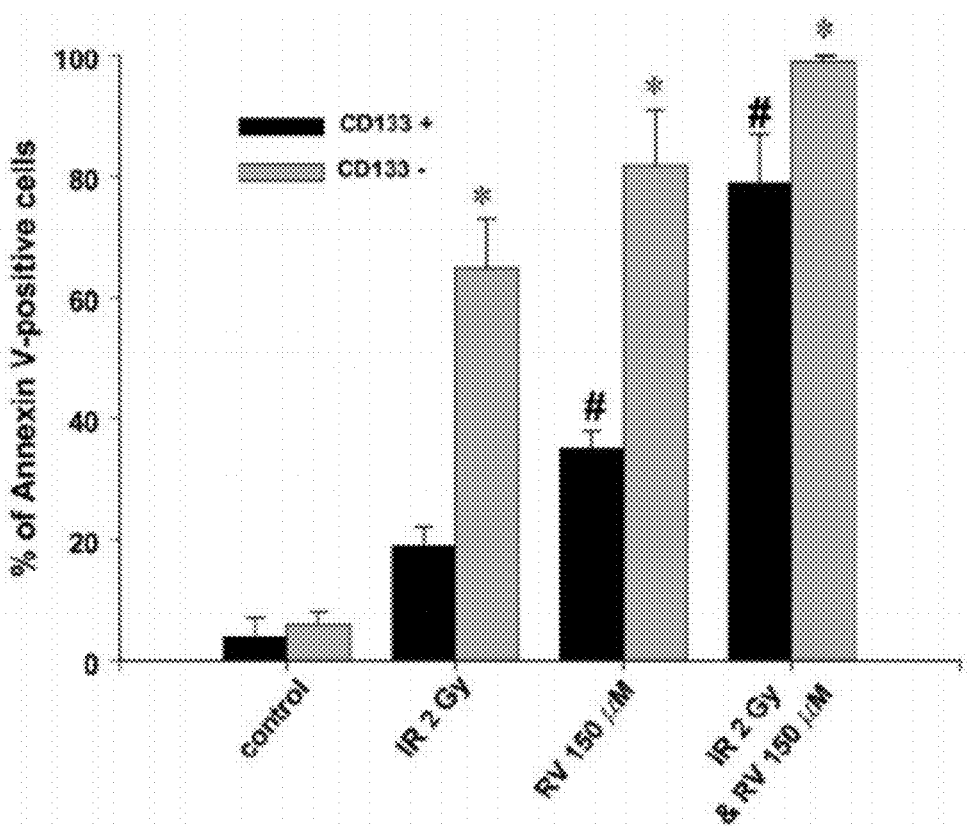
FIG. 14 is evaluation of cytotoxic effects of resveratrol (RV) in MB-CSCs and parental MB cells.
Figure 14B:
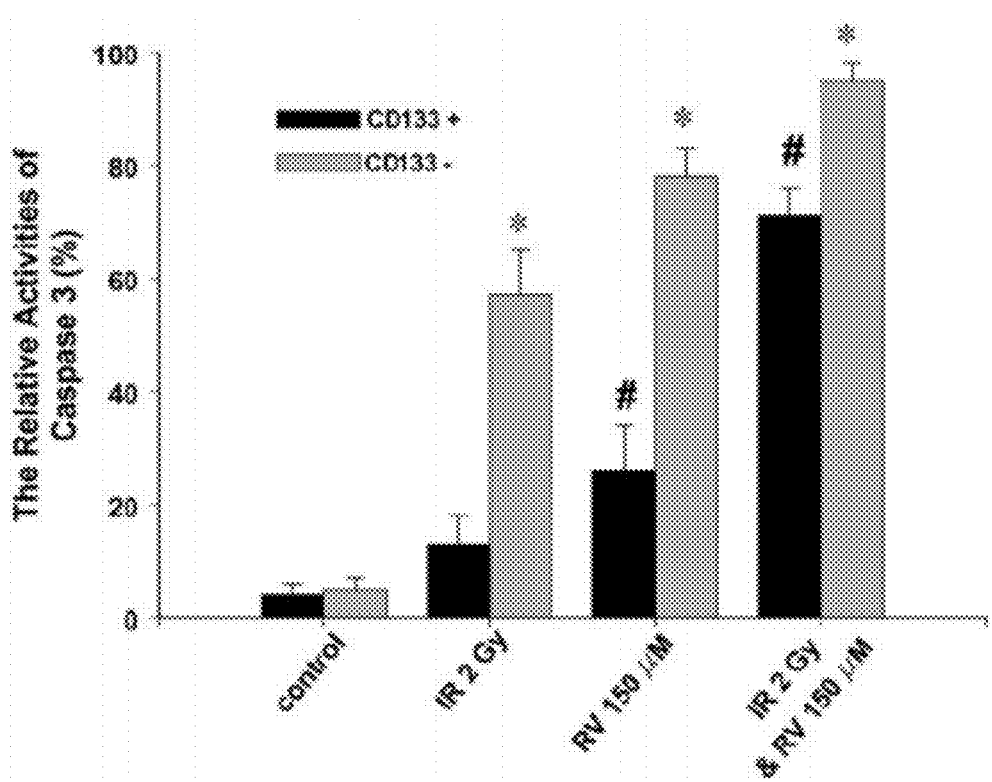
Figure 14C:
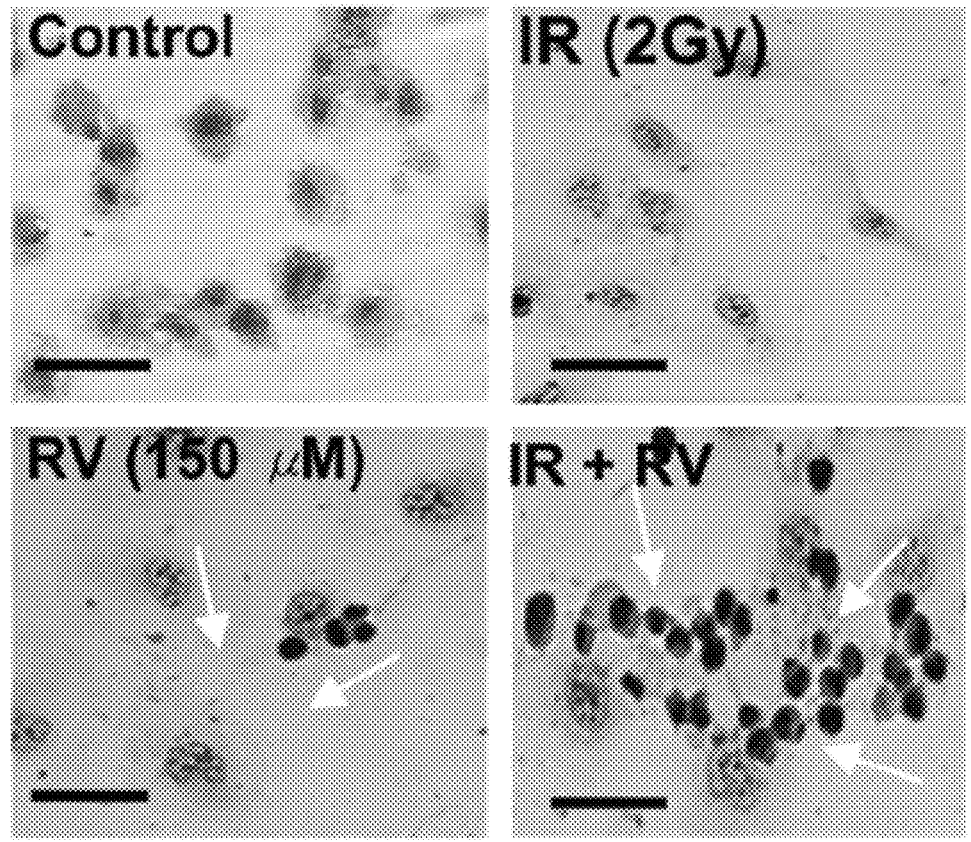
Figure 14D:
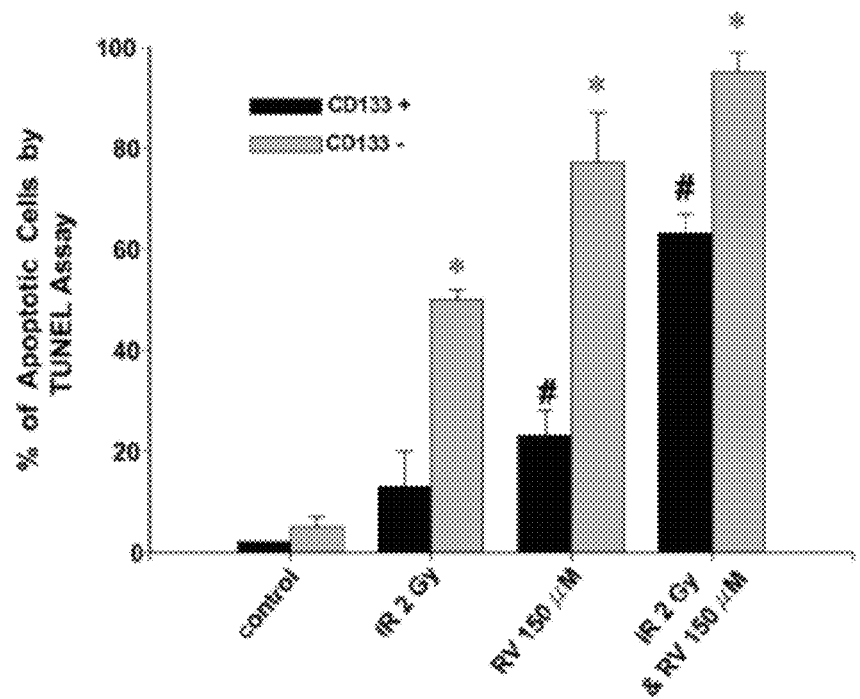

Resveratrol Increases IR-Induced Apoptotic Activity in Treated AT/RT-CD133$^{+/-}$ To determine whether 150 mM RV could induce apoptosis in AT/RT-CD133$^+$ and further increase the radiation effect, we used annexin V (FIG. 14A) and caspase 3 (FIG. 14B) to demonstrate the apoptotic activities in AT/RT-CD133$^{+/-}$ cells at 72 h after 150 mM RV. Furthermore, the TUNEL assay confirmed the formation of apoptotic bodies (FIG. 14C) and demonstrated that 150 mM RV could not only induce apoptosis, but also could increase IR (2 Gy)-mediated apoptotic activity in RV-treated AT/RTCD133$^{+/-}$ (FIG. 14D).

Figure 15A:
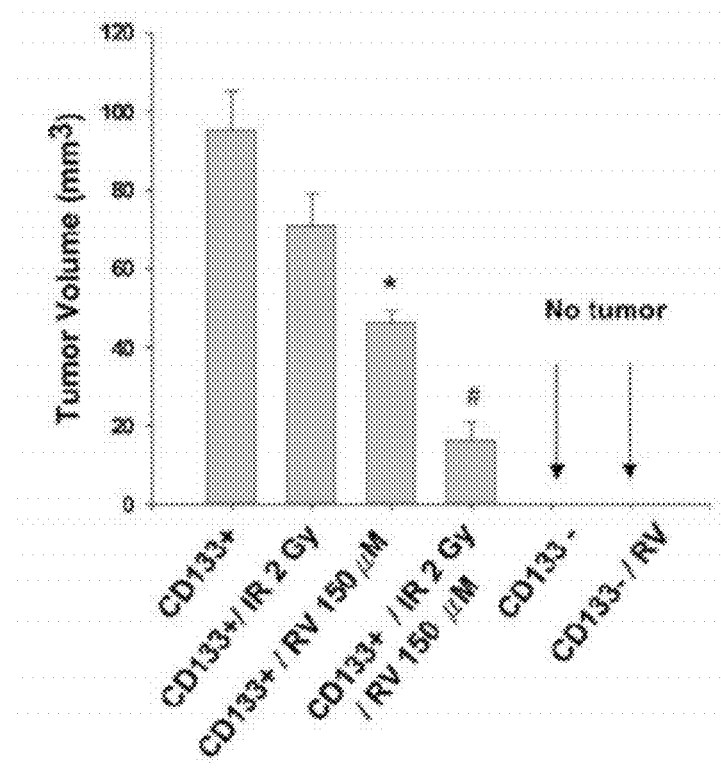
FIG. 15 is determination of radiotherapy effect in MB-CSCs and parental MB cells with or without RV.
Figure 15B:
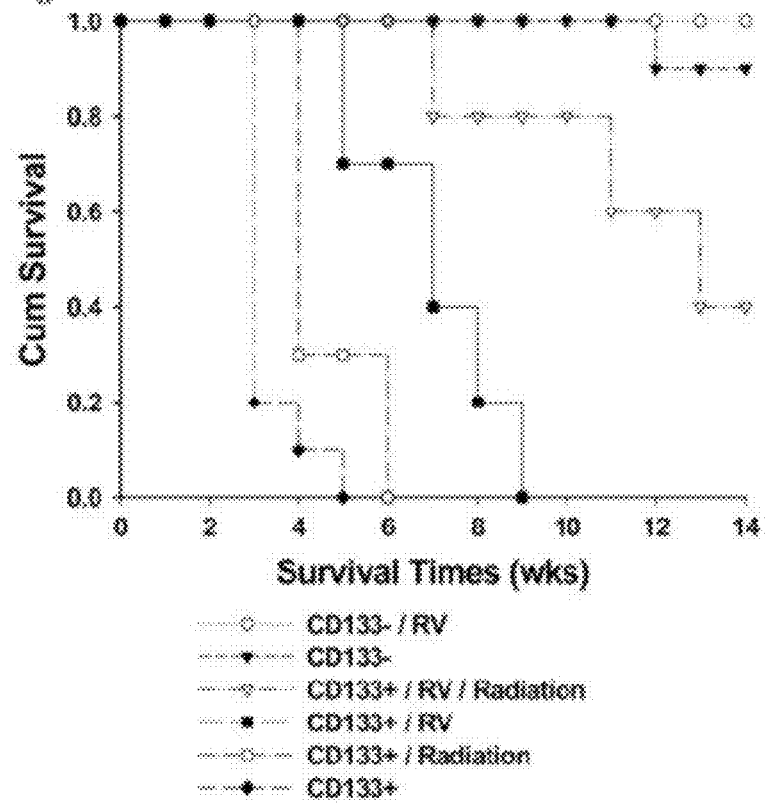

RV Treatment Increased In Vivo Radiosensitivity and Prolonged the Survival of AT/RT-CD133+ Xenotransplanted Mice To further confirm anti-proliferation and radiosensitization in AT/RT-CD133$^+$ in vivo, five groups of cells (CD133$^+$, only IR [2 Gy]-treated CD133+, only 150 mM RV-treated CD$^{133+}$, 150 mM RV combined with IR-treated CD133$^+$, CD133$^-$, and 150 mMRV-treated CD133$^-$) were individually injected into the tail vein of SCID mice and analyzed using xenotransplanted tumorigenicity assays. The tumor volumes for CD133$^+$ treated by RV/IR were significantly decreased as compared with those for CD133$^+$ or CD133$^+$ treated with only IR (p<0.01; FIG. 15A). By contrast, there was no tumor formation in CD133$^-$ and RV-treated CD133$^-$ groups (FIG. 15A). Kaplan-Meier survival analysis showed that the mean survival times for animals with CD133$^+$ and 150 mM RV/IR were significantly prolonged as compared to animals with untreated CD133$^+$ or only IR-treated CD133$^+$ (p<0.01; FIG. 15B). Our data suggest that RV can effectively inhibit the proliferation and tumorigenicity of AT/RT-CD133$^+$, and enhance radiosensitivity in RV-treated AT/RT-CD133$^+$.

Example 4

Resveratrol (RV) Treatment Increased Radiosensitivity of Medulloblastoma-Cancer-Related Stem Cell Isolation of the Subsets of Cancer Stem-Like Cells from Medulloblastoma Tissues Dissociated cells from the samples of medulloblastoma patients were cultured in serum-free DMEM/F12 (GIBCO) medium supplemented with N2 supplement (R&D), 10 ng/ml human recombinant bFGF (R&D) and 10 ng/ml EGF. Gamma radiation was delivered by a Theratronic cobalt unit T-1000 (Theratronic Internation, Inc., Ottawa, Canada) at a dose rate of 1.1 Gy/min (SSD=57.5 cm). For evaluation of cell proliferation, cells were seeded on 24-well plates at a density of 2×10$^4$ cells/well in medium, followed by the methyl thiazol tetrazolium assay (MTT assay; Sigma-Aldrich Co.).

Immunophenotypic Analysis

For cell surface antigen phenotyping, the different passage cells were detached and stained with anti-CD133 with secondary phycoerythrin (PE)-coupled antibodies (Miltenyi Biotec). BMSCs were fixed with 2% paraformaldehyde until they were ready for analysis using FACSCalibur apparatus (Becton-Dickinson).

Result

Isolation and Characterization of Cancer Stem-Like Cells from Medulloblastoma

Figure 16A:
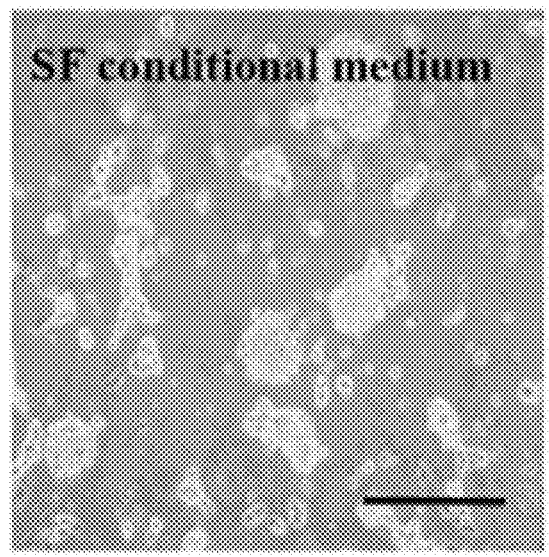
Figure 16B:
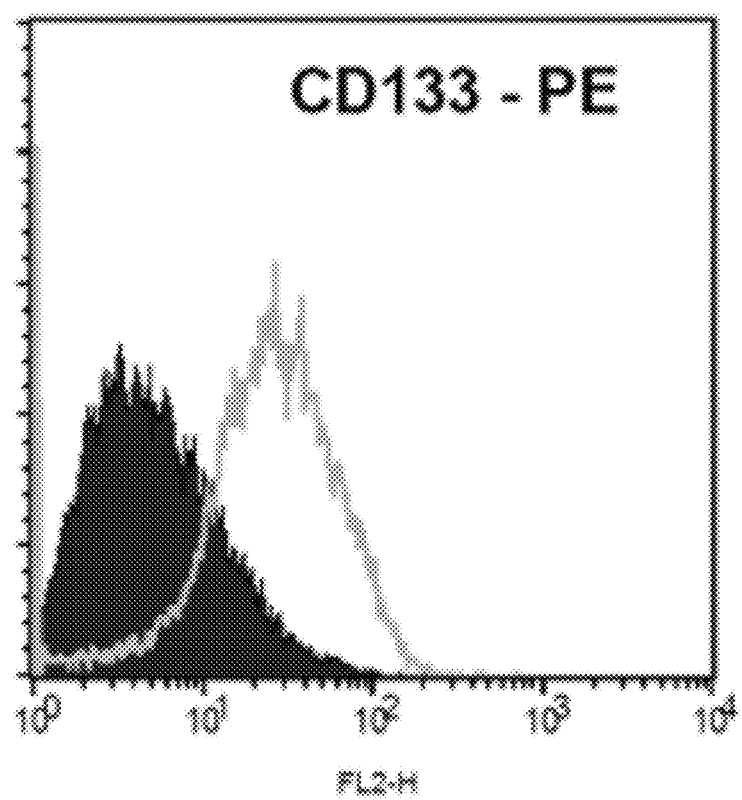
Figure 16C:
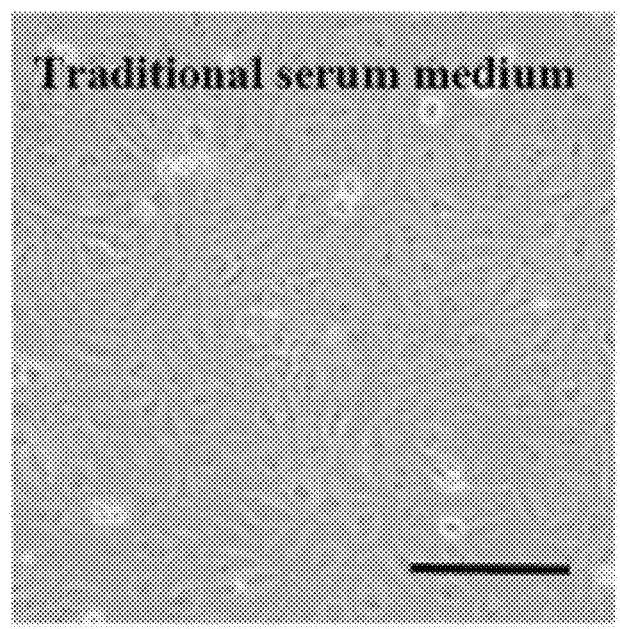
Figure 16D:
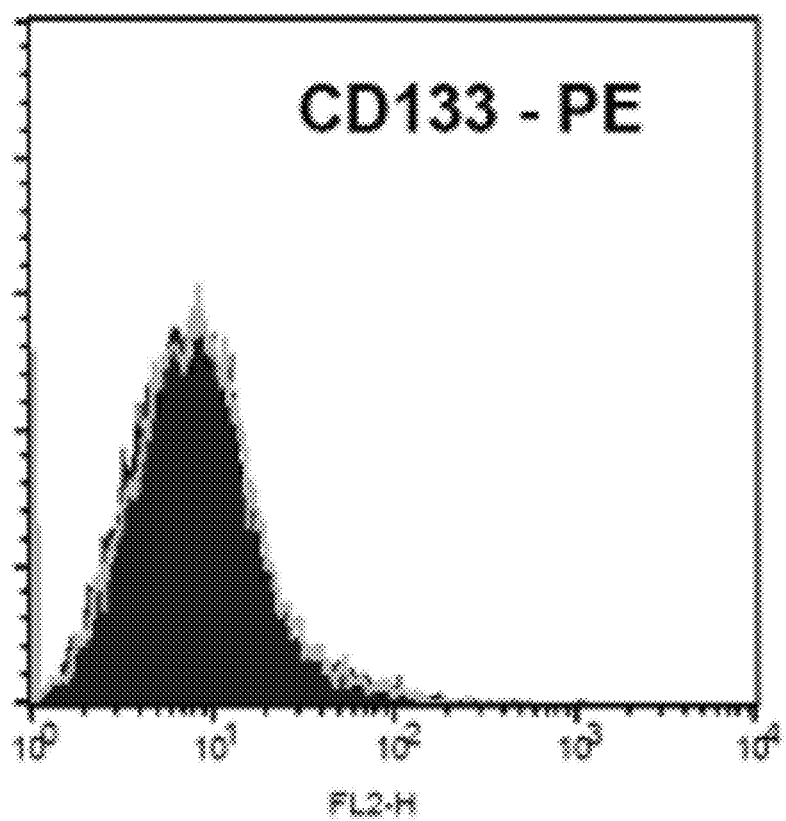
Figure 17A:
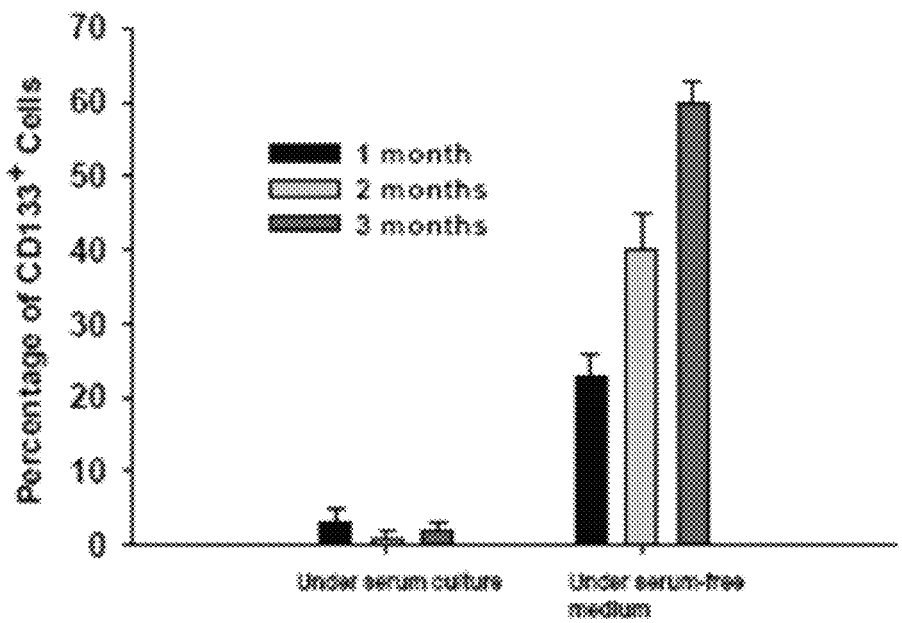
FIG. 17 shows MTT assay of GBMS1 and GBMS1R1 treated with different dosage of Taxol.
Figure 17B:
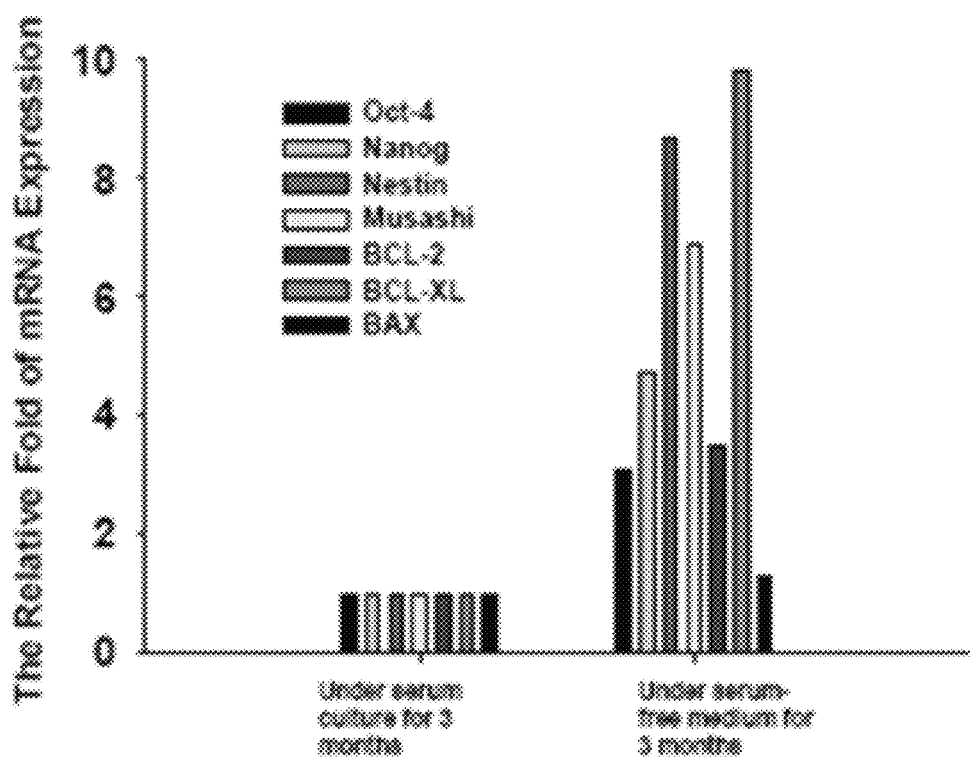

It has been known that cancer-related stem cells and glioma stem cells can be cultured and enriched in suspension to generate floating spheroid-like bodies (SB) and maintain the self-renewal capabilities in serum-free media with bFGF & EGF. For 1 month under DF-12 serum-free medium with bFGF and EGF, the suspended SB cancer stem-like cells (CSCs) were successfully isolated from medulloblastoma samples (FIG. 16A, 16B). These CSCs derived from medulloblastoma (MB) could stably proliferate to form SB in serum-free medium with bFGF and EGF. The result of a FACSscan showed that MB-CSCs derived from SB under serum-free/bFGF/EGF medium could be stained positively for the marker of brain tumor stem cell—CD133. In contrast, the parental tumor cells derived from MB were primarily cultured and attached on the dish under serum-contained medium (traditional formula; FIG. 16C). It only presented the very low level of CD133 antigen in these parental MB cells (FIG. 16D). Importantly, the percentage of CD133-positive cells in MB-CSC was gradually and significantly increased under serum-free media with bFGF & EGF for a 3-month culture (FIG. 17A; p<0.05), but not detected in primary parental cancer cells even after a 3-month serum-condition culture (FIG. 17A). Furthermore, quantitative real-time RT-PCR showed that the mRNA expression levels of stem cell-related genes (Oct-4, Oct-4A, Nanog, Sox-2, Nestin, and Musashi-1) and anti-apoptotic (Bcl-2 and Bcl-xL) were up-regulated in MB-CSC as compared to the parental MB cells (FIG. 17B; p<0.05). In sum, our data indicated that the spheroid-like MB cells (MB-CSCs) selected by serum-free media with bFGF & EGF present the characteristics of cancer stem-like cells.

Evaluation of Cytotoxic Effects of Resveratrol in MB-CSC and Parental Tumors

Figure 18A:
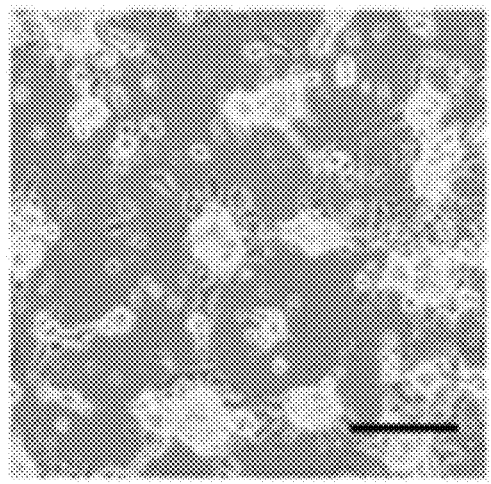
FIG. 18 shows MTT assay of GBMS1 and GBMS1R1 treated with different dosage of Taxol.
Figure 18B:
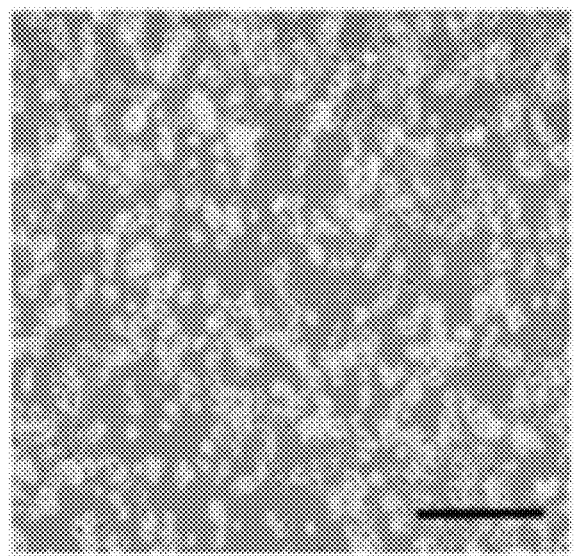

MB-CSCs were treated with different doses of RV and cell viability was analyzed using the MTT assay. As shown in FIG. 3, MB-CSC (FIG. 18A) were treated with RV at different concentrations (0, 10, 50, 100, and 150 μM) for 48 hours. Cell viability of MB-CSC was not significantly affected if the concentration of RV was lower than 50 μM (p>0.05; FIG. 18C). After being treated 48 hours treatment with 100 μM RV, the spheroid-like MB-CSCs detached and became a single-suspension (FIG. 18B). The total cell number and growth rates of MB-CSCs after being treated with 150 μM RV for 48 h were significantly decreased (p<0.001; FIG. 18C). In contrast, the cell viability of parental MB cells (serum-condition culture) could be moderately affected by 50 μM RV and significantly decreased by the treatment of 50 μM RV (p<0.001; FIG. 18C)

Enhanced Radiosensitivity of MB-CSCs after Treatment with Resveratrol

Figure 19:
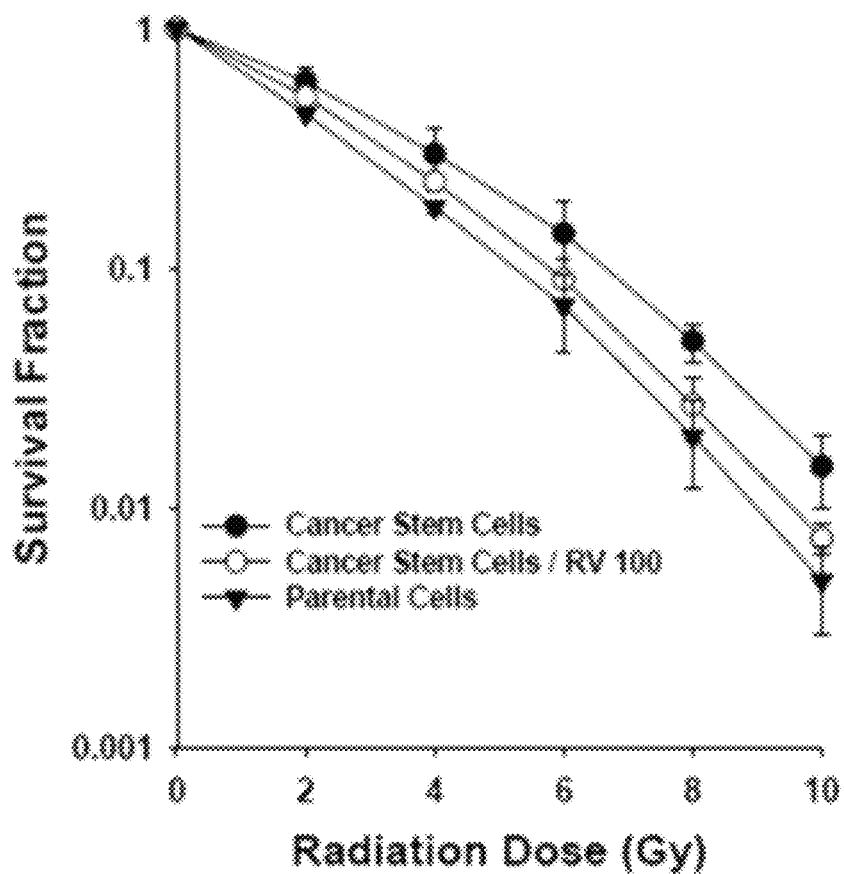
FIG. 19 shows MTT assay of GBMS1 and GBMS1R1 treated with different dosage of Doxorubicin.
Figure 20A:
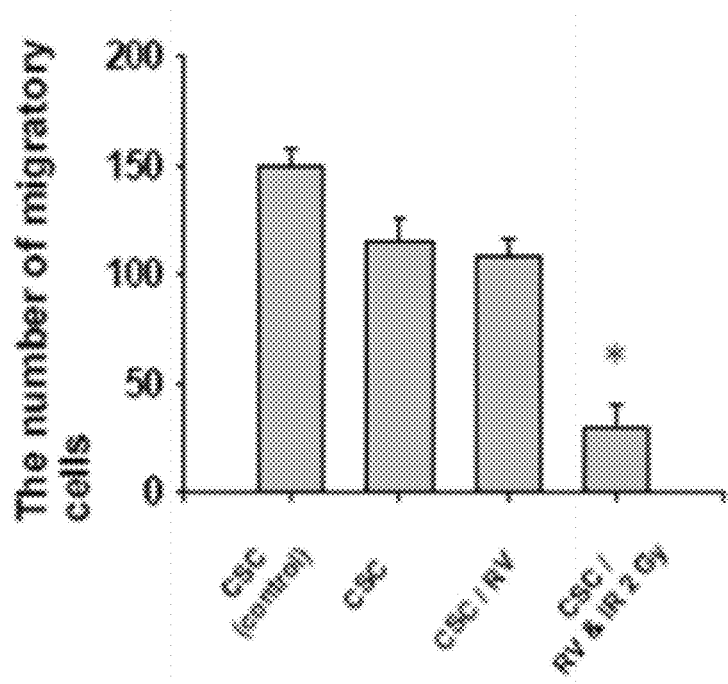
FIG. 20 shows MTT assay of GBMS1 and GBMS1R1 treated with different dosage of Doxorubicin.
Figure 20B:
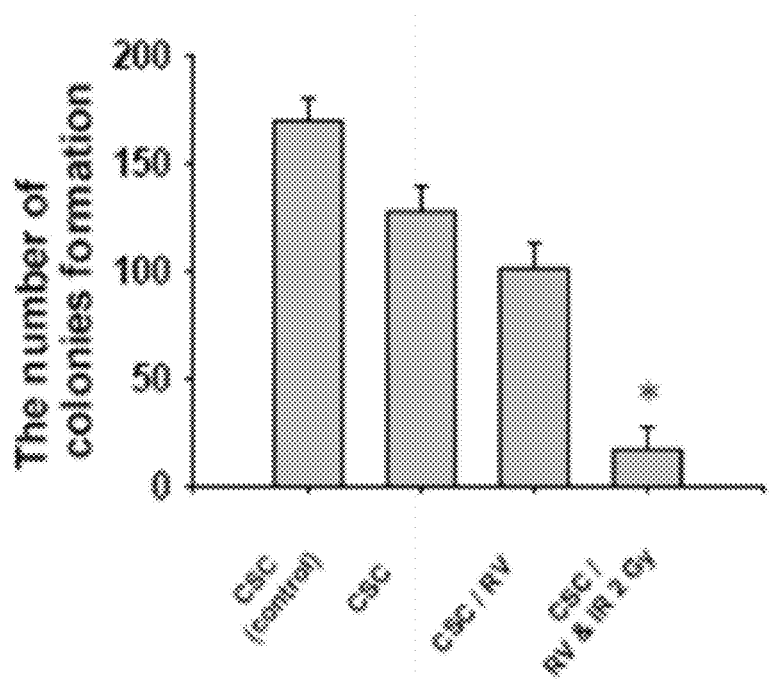
Figure 22A:
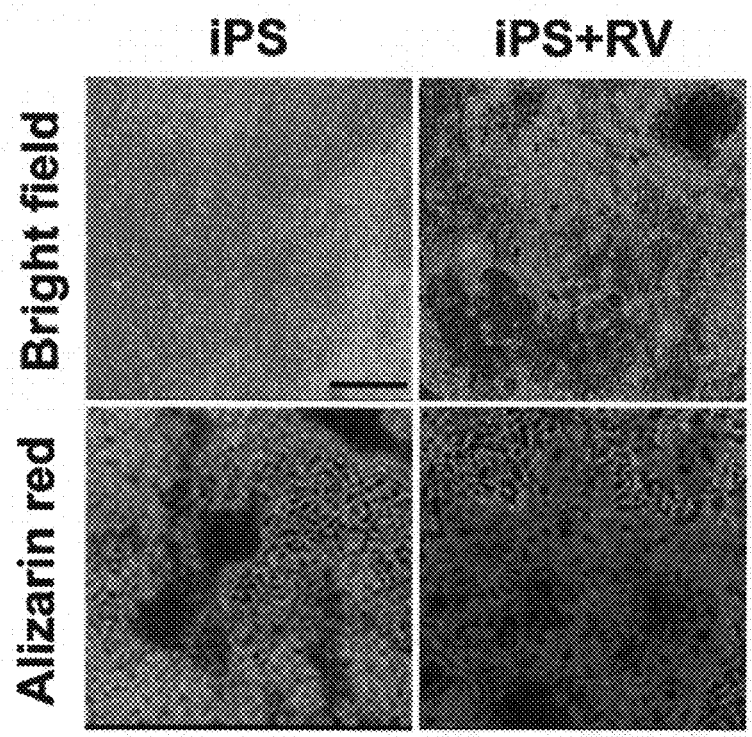
FIG. 22 shows effects of resveratrol (RV) on osteogenic differentiation in iPS and ES cells. (A,B) After 14 days of induction in osteogenic medium with or without 20 $\mu mol \cdot L^{-1}$ resveratrol (RV), the degree of mineralization in iPS and ES cells significantly increased, as detected by Alizarin red staining. Bar=150 μm. (C) Real-time RT-PCR showed that after 14 days of osteogenic induction, the expression of Runx2, OPN, and IBSP (three osteogenic markers) was significantly higher in iPS and ES cells treated with 20 $\mu mol \cdot L^{-1}$ resveratrol (RV) than in those without resveratrol treatment. Data shown here are the mean±SD of three independent experiments. *P<0.05.
Figure 22B:
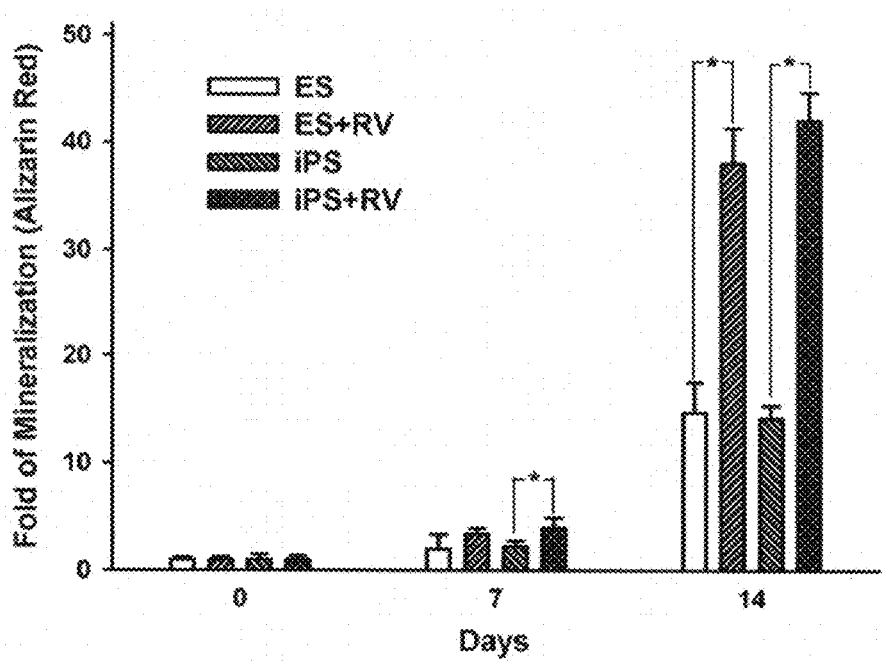
Figure 22C:
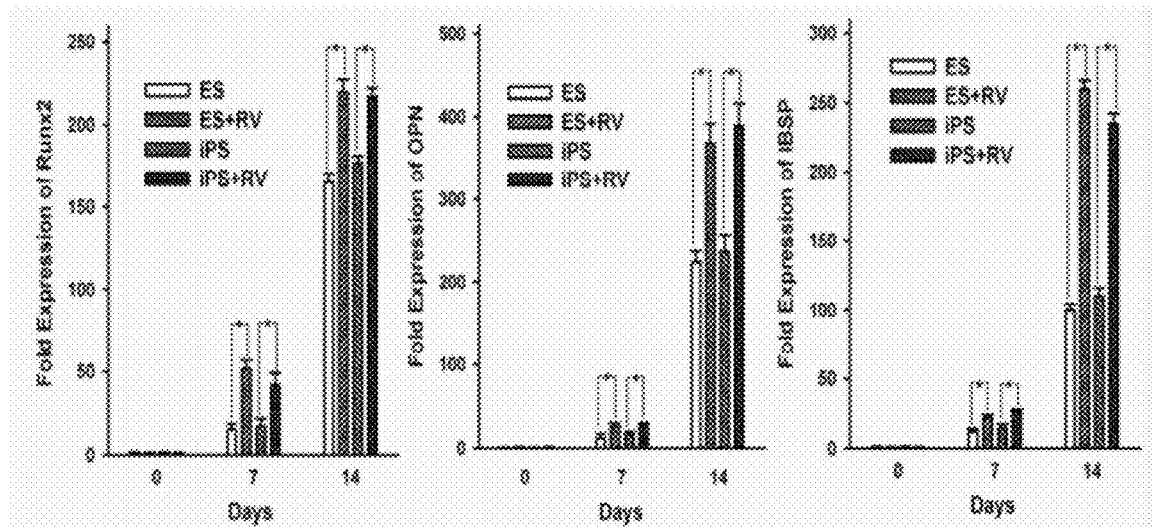
Figure 23A:
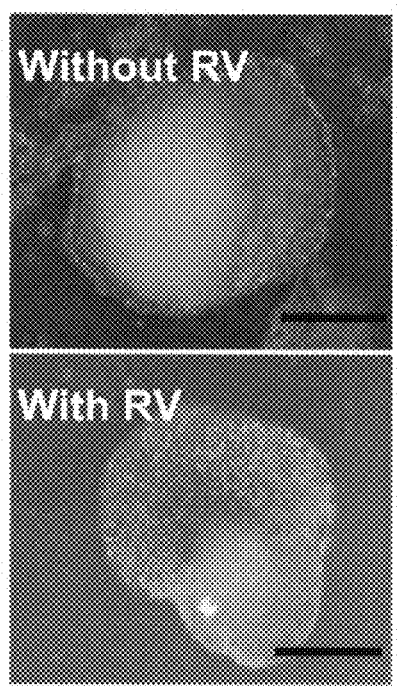
FIG. 23 shows in vivo effects of resveratrol on osteogenic differentiation of iPS cells transplanted to nude mice. (A) iPS cells were infected by lentivirus carrying the green fluorescent protein gene (GFP). EBs derived from GFP-positive iPS cells were cultured in osteogenic induction medium (OIM) for 7 days. (B) $2\times10^6$ iPS cells cultured either in control medium (iPS) or in OIM were injected into subcutaneous sites of nude mice fed with resveratrol (iPS+OIM+RV; 7.5 μg/ml; supplemented in drinking water daily) or control vehicle (iPS+OIM; Each group, N=6 mice). Six weeks after transplantation, the viable transplanted graft was visualized by in vivo GFP imaging (arrows). (C) Immunofluorescent analysis revealed that the expression of OPN in the graft was significantly higher in mice fed with resveratrol (iPS+OIM+RV) than in those from mice fed with vehicle (iPS+OIM). Bar=50 μm. Data shown here are the mean±SD of three independent experiments. *P<0.05.
Figure 23B:
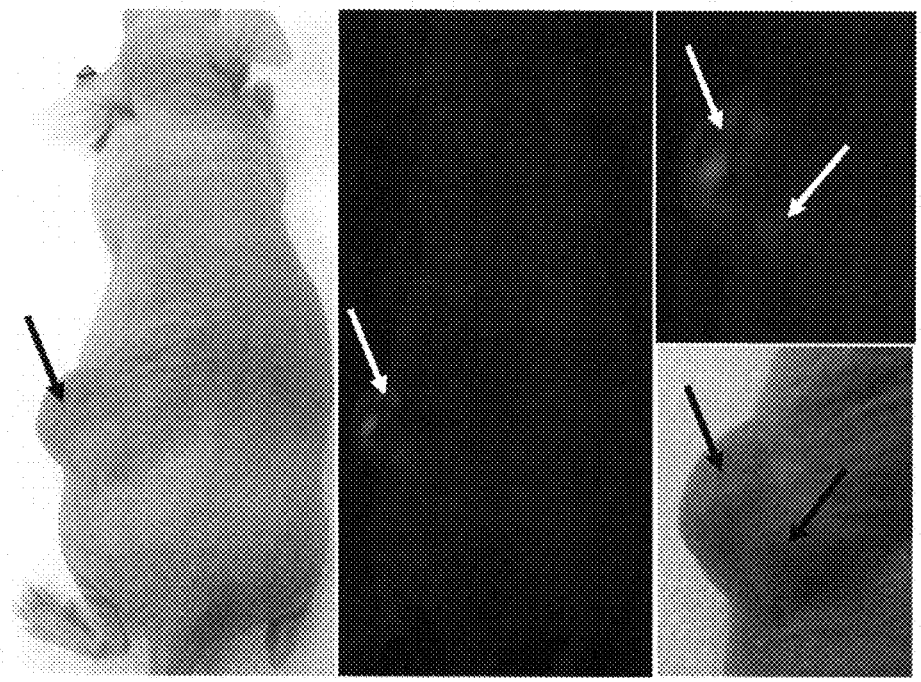
Figure 23C:
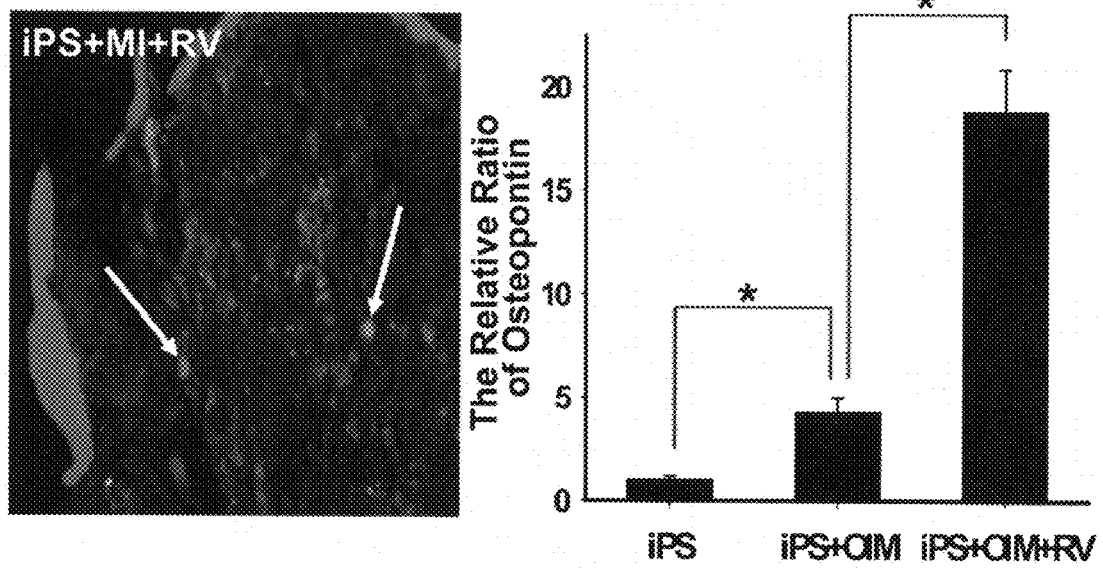
Figure 24A:
FIG. 24 shows iPS cells were cultured in osteogenic induction medium (OIM) for 7 days, followed by injection of $2\times10^6$ cells into subcutaneous sites of nude mice without resveratrol treatment. (A) Six weeks after transplantation, HE staining showed that some ostocyte-like cells were detected in the transplanted graft. However, the teratoma-like formation was still found in grafts from mice transplanted with OIM-treated iPS cells and fed without resveratrol. (B) Immunofluorescent assay further showed higher expression of Oct-4 protein in the tissue section of (A). Bar=50 μm.
Figure 24B:
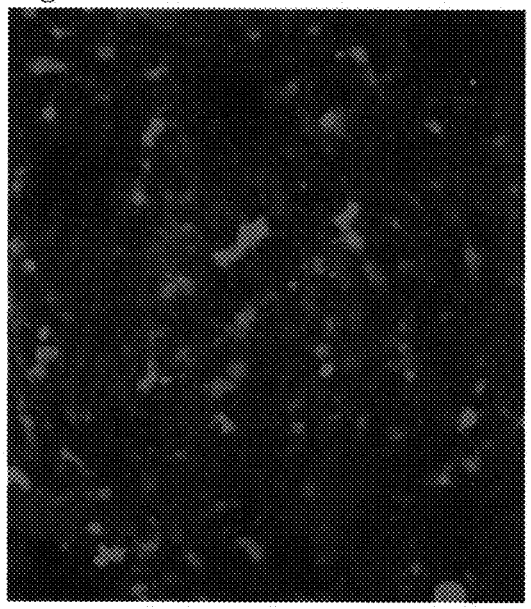
Figure 25A:
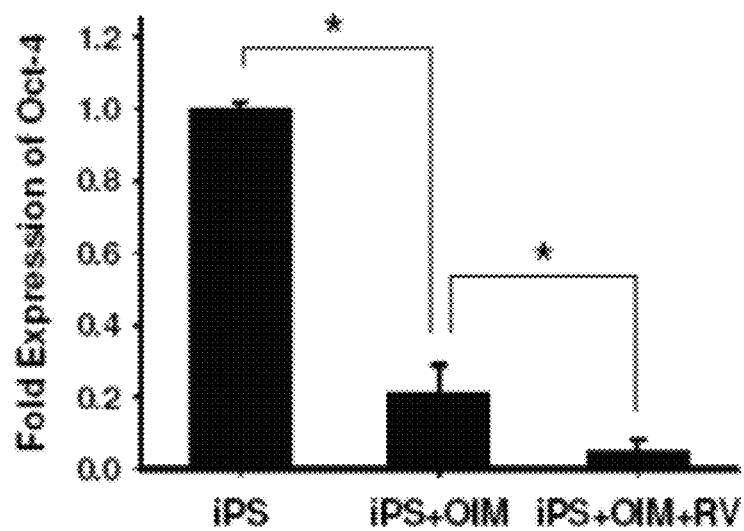
FIG. 25 is RV increased radiosensitivity and inhibited cell growth of MB-CSCs.
Figure 25B:
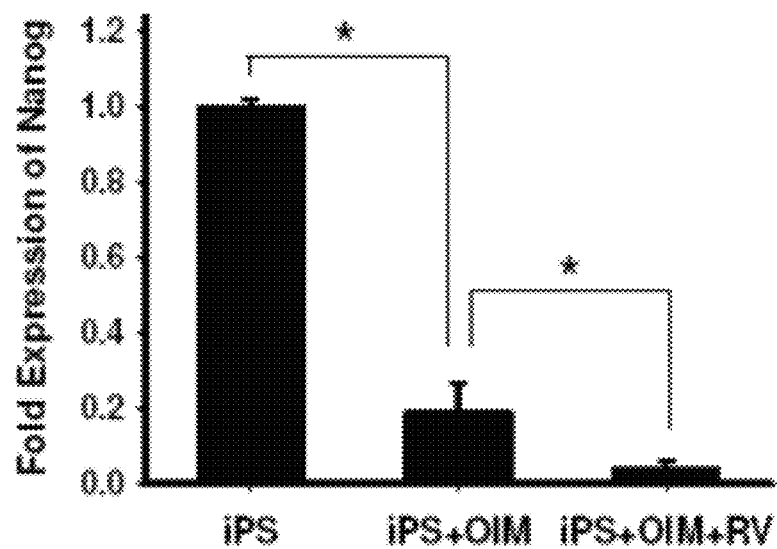
Figure 25C:
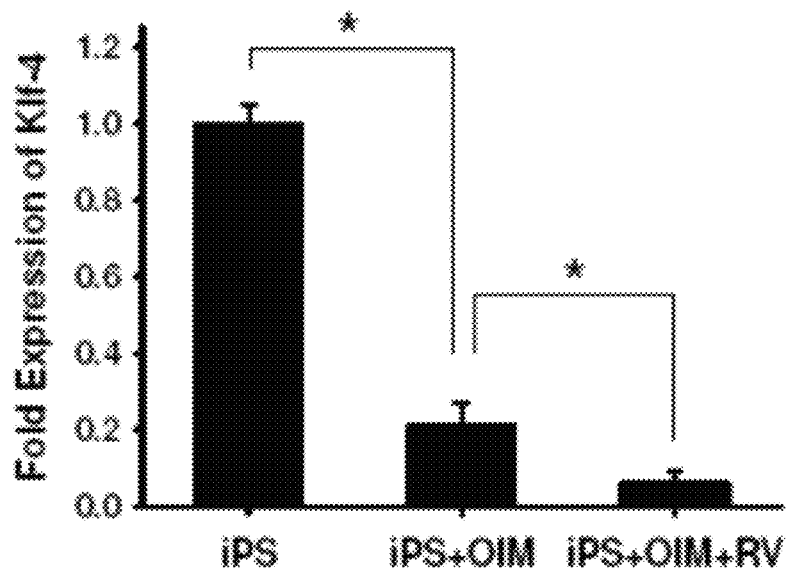
Figure 25D:
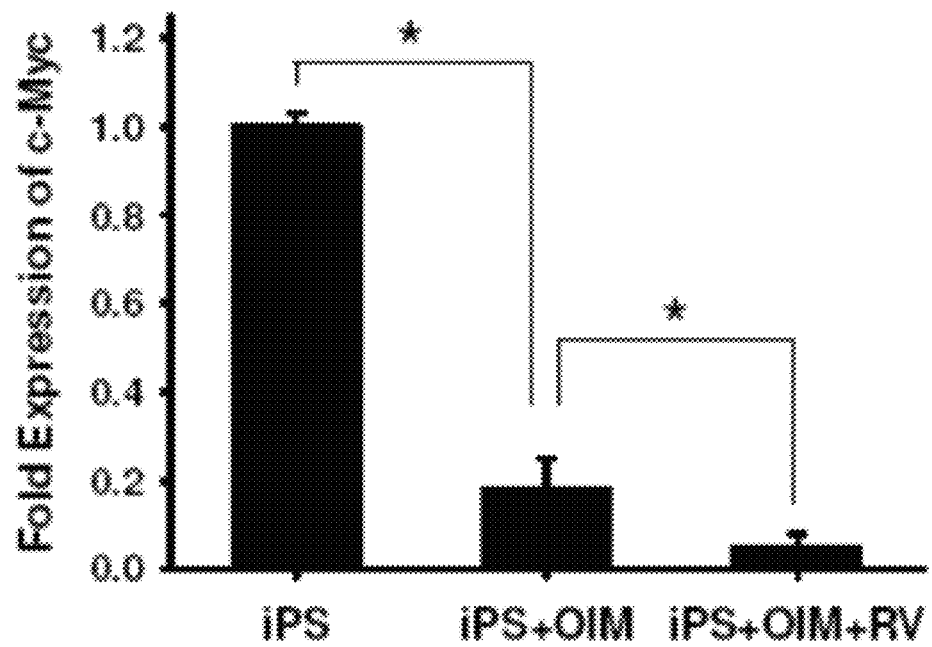

In FIG. 18, the viability of MB-CSCs was reduced by 40-45% when the concentration of RV was 100 μM, and these data suggested that 100 μM RV leads to a significant cytotoxic effect in treated MB-CSCs. To further investigate the role of RV in synergetic treatment for clinical use of MB and MB-CSCs, the optimal concentration of RV as a radiosensitizer for radiotherapy against MB-CSCs was further tested. By applying ionizing radiation (IR) doses from 0 to 10 Gy to the two groups of cells, the results further confirmed that MB-CSCs showed greater radioresistance than the parental MB cells (p<0.001; FIG. 19). Furthermore, the treatment effect of IR-2 Gy on MB-CSCs was also significantly improved with the addition of 100 μM RV (p<0.01; FIG. 4). We further evaluated the in vitro tumorigeneic ability of MB-CSCs before and after the RV treatment. Compared with the IR (2 Gy) treatment alone, migration/invasion (FIG. 20A) and tumor colony formation (FIG. 20B) were significantly inhibited in MB-CSCs treated with 100 μM RV alone or 100 μM RV combined with 2 Gy IR. These data provide evidence that the effectiveness and radiosensitivity of radiation treatment for MB-CSCs can be improved with RV treatment.

Example 5

Resveratrol Promotes Differentiation and Inhibit Teratoma/Tumor Formation in Induced Pluripotent Stem Cells (iPS) and Embryonic Stem Cells Osteogenic Differentiation For osteogenic induction, ES or iPS cells were cultured in DMEM-LG (Invitrogen) supplemented with 50 μg·ml$^{-1}$ ascorbate-2 phosphate, 10 nmol·L$^{-1}$ dexamethasone, and 10 mmol·L$^{-1}$ β-glycerophosphate (Sigma, St. Louis, Mo.) for 2 weeks. At the end of osteogenic induction, cells were washed twice with PBS, fixed for 10 min at room temperature with 3.7% paraformaldehyde, and stained with von Kossa stain and Alizarin red to assess osteogenic differentiation.

Real-Time RT-PCR

Real-time RT-PCR was performed as previously described. Briefly, total RNA (1 μg) of each sample was reverse-transcribed using 0.5 μg oligo dT and 200 U Superscript II RT (Invitrogen). The primer sequences for real-time RT-PCR were listed in Table 2. The amplification was carried out in a total volume of 20 μl containing 0.5 μmol·L$^{-1}$ of each primer, 4 mmol·L$^{-1}$ MgCl$_2$, 2 μl LightCycler™-FastStart DNA Master SYBR green I (Roche Molecular Systems, Alameda, Calif.) and 2 μl of 1:10 diluted cDNA. PCR reactions were prepared in duplicate and performed using the following program: 95° C. for 10 min, followed by 40 cycles of denaturation at 95° C. for 10 sec. annealing at 55° C. for 5 sec. and extension at 72° C. for 20 sec. Standard curves (cycle threshold values versus template concentration) were prepared for each target gene and for the endogenous reference gene (GAPDH) for each sample. Quantification of unknown samples was performed using LightCycler Relative Quantification Software version 3.3 (Roche).

TABLE 2

The primer sequences used for real-time RT-PCR in example 5

| Gene | Accession No. | Sequences (5' to 3') | Product size (in bp) | Tm (° C.) |
|---|---|---|---|---|
| PPARgamma 2 | NM_011146 | F: CAAAGGCATGGGGTCACTT<br>R: GGACAGCATATCCCTAACTTTCT | 219 | 55 |
| Runx2 | NM_009820 | F: TGGCAGCACGCTATTAAATC<br>R: TCTGCCGCTAGAATTCAAAA | 103 | 55 |
| Osteopontin | NM_009263 | F: CAAATTCAAAGATATCTTTGTTTC<br>R: CCCCACTATCTGATGTCTCT | 214 | 55 |
| Oct-4 | NM_013633 | F: TGTGGACCTCAGGTTGGACT<br>R: CTTCTGCAGGGCTTTCATGT | 201 | 55 |
| Nanog | NM_028016 | F: CATCTTCTGCTTCCTGGCAA<br>R: CTGGGAACGCCTCATCAA | 238 | 55 |
| integrin binding sialoprotein | NM_008318 | F: TTCCGCAAATGCTTTTGTTT<br>R: GCGCAGTTAGCAATAGCACA | 184 | 55 |
| GAPDH | NM_008084 | F: AGCCAAAAGGGTCATCATCT<br>R: GGGGCCATCCACAGTCTTCT | 240 | 55 |

In Vivo Analysis of Cell Growth and Green Fluorescence Protein Imaging

All procedures involving animals were performed in accordance with the institutional animal welfare guidelines of Taipei Veterans General Hospital. A total of 2×10$^6$ cells were injected into subcutaneous tissue of back skin in nude mice (BALB/c strain) aged 6 weeks and resveratrol (7.5 µg/ml) was supplemented in drinking water daily. In vivo GFP imaging was visualized and measured by an illuminating device (LT-9500 Illumatool TLS equipped with excitation illuminating source [470 nm] and filter plate [515 nm]). The integrated optical density of green fluorescence intensity was captured and then analyzed by Image Pro-plus software.

Statistical Analysis

The results were expressed as the mean±SD. Statistical analyses were performed by one-way or two-way ANOVA, followed by Tukey's test, as appropriate. A P-value less than 0.05 was considered as statistically significant.

Results

Potential for Adipogenic and Osteogenic Differentiation in iPS Cells

Figure 1B:
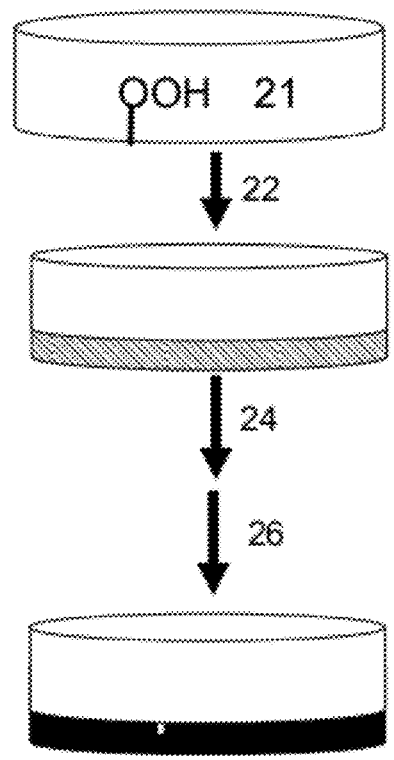

In previous studies, mesenchymal stem cells (MSCs) were successfully isolated from bone marrow and induced to differentiate into mesodermal lineages. Following the protocols used in the aforementioned studies, we were able to differentiate iPS cells and embryonic stem cells (ESC; data not shown) into adipocytes after 14 days of culture in adipogenic medium, as confirmed by positive staining with oil red O and up-regulated expression of PPARr2 mRNA (FIG. 1A). To test the potential for osteogenic differentiation, iPS EBs and ESC EBs (data not shown) were cultured in osteogenic medium containing 10 nmol·$L^{-1}$ dexamethasone, and 10 mmol·$L^{-1}$ β-glycerophosphate. After osteogenic induction for 14 days, the iPS cells and ESC (data not shown) exhibited osteocyte morphology and formed a mineralized matrix, as evidenced by von Kossa and Alizarin red staining (FIG. 1B). As measured by real-time RT-PCR, the expression of Runx2 (an osteoblast marker) and osteopontin (OPN; an osteogenesis-related gene) increased significantly after 7 and 14 days of osteogenic induction in iPS cells and ESC (data not shown), as compared with undifferentiated iPS cells (FIG. 1B). In contrast, Oct-4 and Nanog were highly expressed in undifferentiated iPS cells and ESC (data not shown), but their expression was significantly reduced in iPS cells and ESC (data not shown) after 7 and 14 days of osteogenic induction (FIG. 1C). To examine the effect of resveratrol on osteogenic induction in iPS and ES cells, 20 µmol·$L^{-1}$ resveratrol or the corresponding vehicle was added to the osteogenic medium. The addition of resveratrol to the osteogenic medium significantly increased calcium accumulation in iPS and ES cells, as shown by Alizarin red staining (orange-red areas; FIGS. 2A and B). After 7 or 14 days of induction, the expression of Runx2, OPN and IBSP (intergin binding sialoprotein, an osteogenesis-related gene) was significantly higher in iPS and ES cells treated with resveratrol than in those without resveratrol treatment (FIG. 2C).

In Vivo Effects of Resveratrol on Osteogenic Differentiation of iPS Cells (FIGS. 3-5)

To investigate the effects of resveratrol on osteogenic differentiation in vivo, iPS cells were additionally infected by a lentivector combined with GFP. iPS cells were cultured in osteogenic medium for 7 days (FIG. 3A), and then injected into subcutaneous sites of nude mice at 2×$10^6$ cells/mouse. The mice were fed with resveratrol (7.5 µg/ml; supplemented in drinking water daily) or control vehicle. Six weeks after transplantation, iPS cells were found to proliferate (FIG. 3B) and GFP signals were detected in the viable transplanted graft (FIG. 3B, arrows). Immunofluorecent assay showed that the expression of OPN was significantly higher in grafts from mice fed with resveratrol than in those from mice fed with vehicle (FIG. 3C). No teratoma-like formation was noted in grafts from mice transplanted with osteogenic medium-treated iPS cells and fed with resveratrol (FIG. 3C). Previous studies have shown that transplanted iPS cells are likely to form teratomas in vivo, a feature also found in ES cells. In the present invention, teratoma-like tissues with higher expression of Oct-4 were still detected in grafts from mice transplanted with osteogenic medium-treated iPS cells and fed without resveratrol (FIG. 4A). Results of quantitative RT-PCR further showed the expression of Oct-4, Nanog, Klf-4, and C-Myc, genes related to embryonic cell stemness and tumorigenicity, was significantly suppressed in grafts from mice transplanted with osteogenic medium-treated iPS cells and fed with resveratrol (FIG. 5). Taken together, these results of transplantation experiments demonstrated that resveratrol can effectively promote osteogenic differentiation and significantly inhibit tumorigenicity in vivo.

What is claimed is:

1. A method of treating or preventing atypical teratoid/rhabdoid tumor comprising administrating a therapeutically effective amount of resveratrol, wherein the resveratrol acts on both CD133-negative cells and CD133-positive cancer-related stem cells, wherein the CD133-negative cells and CD133-positive cancer-related stem cells are derived from atypical teratoid/rhabdoid tumor.

2. A method of enhancing radiosensitivity of atypical teratoid/rhabdoid tumor cells comprising radiotherapy with resveratrol, wherein the resveratrol acts on both CD133-negative cells and CD133-positive cancer-related stem cells, wherein the CD133-negative cells and CD133-positive cancer-related stem cells are derived from atypical teratoid/rhabdoid tumor.

3. The method of claim 2, wherein the resveratrol concentration is 50 to 150 μM.

4. The method of claim 2, wherein the cancer-related stem cells have elevated expression of ATP-Binding cassette transporter genes compared with CD133-negative cells.

5. The method of claim 4, wherein the ATP-binding cassette transporter genes are ABCC1, ABCG2 and ABCB1.

* * * * *

SEQUENCE LISTING

```
<160> NUMBER OF SEQ ID NOS: 38

<210> SEQ ID NO 1
<211> LENGTH: 18
<212> TYPE: DNA
<213> ORGANISM: Artificial
<220> FEATURE:
<223> OTHER INFORMATION: Oct-4 forward primer
<220> FEATURE:
<221> NAME/KEY: misc_feature
<222> LOCATION: (1)..(18)
<223> OTHER INFORMATION: Oct-4 forward primer

<400> SEQUENCE: 1
accgagtgag aggcaacc                                                 18

<210> SEQ ID NO 2
<211> LENGTH: 20
<212> TYPE: DNA
<213> ORGANISM: Artificial
<220> FEATURE:
<223> OTHER INFORMATION: Oct-4 reverse primer
<220> FEATURE:
```

```
<221> NAME/KEY: misc_feature
<222> LOCATION: (1)..(20)
<223> OTHER INFORMATION: Oct-4 reverse primer

<400> SEQUENCE: 2
tgagaaagga gacccagcag                                                    20

<210> SEQ ID NO 3
<211> LENGTH: 19
<212> TYPE: DNA
<213> ORGANISM: Artificial
<220> FEATURE:
<223> OTHER INFORMATION: Oct-4A forward primer
<220> FEATURE:
<221> NAME/KEY: misc_feature
<222> LOCATION: (1)..(19)
<223> OTHER INFORMATION: Oct-4A forward primer

<400> SEQUENCE: 3
gtggagagca actccgatg                                                     19

<210> SEQ ID NO 4
<211> LENGTH: 20
<212> TYPE: DNA
<213> ORGANISM: Artificial
<220> FEATURE:
<223> OTHER INFORMATION: Oct-4A reverse primer
<220> FEATURE:
<221> NAME/KEY: misc_feature
<222> LOCATION: (1)..(20)
<223> OTHER INFORMATION: Oct-4A reverse primer

<400> SEQUENCE: 4
tgctccagct tctccttctc                                                    20

<210> SEQ ID NO 5
<211> LENGTH: 21
<212> TYPE: DNA
<213> ORGANISM: Artificial
<220> FEATURE:
<223> OTHER INFORMATION: SOX-2 forward primer
<220> FEATURE:
<221> NAME/KEY: misc_feature
<222> LOCATION: (1)..(21)
<223> OTHER INFORMATION: SOX-2 foward primer

<400> SEQUENCE: 5
cgagtggaaa cttttgtcgg a                                                  21

<210> SEQ ID NO 6
<211> LENGTH: 16
<212> TYPE: DNA
<213> ORGANISM: Artificial
<220> FEATURE:
<223> OTHER INFORMATION: SOX-2 reverse primer
<220> FEATURE:
<221> NAME/KEY: misc_feature
<222> LOCATION: (1)..(16)
<223> OTHER INFORMATION: SOX-2 reverse primer

<400> SEQUENCE: 6
tgtgcagcgc tcgcag                                                        16

<210> SEQ ID NO 7
<211> LENGTH: 23
<212> TYPE: DNA
<213> ORGANISM: Artificial
<220> FEATURE:
<223> OTHER INFORMATION: Nanog forward primer
<220> FEATURE:
```

```
<221> NAME/KEY: misc_feature
<222> LOCATION: (1)..(23)
<223> OTHER INFORMATION: Nanog forward primer

<400> SEQUENCE: 7
attcaggaca gccctgattc ttc                                          23

<210> SEQ ID NO 8
<211> LENGTH: 22
<212> TYPE: DNA
<213> ORGANISM: Artificial
<220> FEATURE:
<223> OTHER INFORMATION: Nanog reverse primer
<220> FEATURE:
<221> NAME/KEY: misc_feature
<222> LOCATION: (1)..(22)
<223> OTHER INFORMATION: Nanog reverse peimer

<400> SEQUENCE: 8
tttttgcgac actcttctct gc                                           22

<210> SEQ ID NO 9
<211> LENGTH: 18
<212> TYPE: DNA
<213> ORGANISM: Artificial
<220> FEATURE:
<223> OTHER INFORMATION: Nestin forward primer
<220> FEATURE:
<221> NAME/KEY: misc_feature
<222> LOCATION: (1)..(18)
<223> OTHER INFORMATION: Nestin forward primer

<400> SEQUENCE: 9
aggaggagtt gggttctg                                                18

<210> SEQ ID NO 10
<211> LENGTH: 18
<212> TYPE: DNA
<213> ORGANISM: Artificial
<220> FEATURE:
<223> OTHER INFORMATION: Nestin reverse primer
<220> FEATURE:
<221> NAME/KEY: misc_feature
<222> LOCATION: (1)..(18)
<223> OTHER INFORMATION: Nestin reverse primer

<400> SEQUENCE: 10
ggagtggagt ctggaagg                                                18

<210> SEQ ID NO 11
<211> LENGTH: 16
<212> TYPE: DNA
<213> ORGANISM: Artificial
<220> FEATURE:
<223> OTHER INFORMATION: Musashi forward primer
<220> FEATURE:
<221> NAME/KEY: misc_feature
<222> LOCATION: (1)..(16)
<223> OTHER INFORMATION: Musashi forward primer

<400> SEQUENCE: 11
tccctcggcg agcaca                                                  16

<210> SEQ ID NO 12
<211> LENGTH: 17
<212> TYPE: DNA
<213> ORGANISM: Artificial
<220> FEATURE:
<223> OTHER INFORMATION: Musashi reverse primer
<220> FEATURE:
```

```
<221> NAME/KEY: misc_feature
<222> LOCATION: (1)..(17)
<223> OTHER INFORMATION: Musashi reverse primer

<400> SEQUENCE: 12
gacagccccc ccacaaa                                                    17

<210> SEQ ID NO 13
<211> LENGTH: 21
<212> TYPE: DNA
<213> ORGANISM: Artificial
<220> FEATURE:
<223> OTHER INFORMATION: Myc forward primer
<220> FEATURE:
<221> NAME/KEY: misc_feature
<222> LOCATION: (1)..(21)
<223> OTHER INFORMATION: Myc forward primer

<400> SEQUENCE: 13
ggaacgagct aaaacggagc t                                               21

<210> SEQ ID NO 14
<211> LENGTH: 23
<212> TYPE: DNA
<213> ORGANISM: Artificial
<220> FEATURE:
<223> OTHER INFORMATION: Myc reverse primer
<220> FEATURE:
<221> NAME/KEY: misc_feature
<222> LOCATION: (1)..(23)
<223> OTHER INFORMATION: Myc reverse primer

<400> SEQUENCE: 14 ggcctttttca ttgttttcca act                                            23

<210> SEQ ID NO 15
<211> LENGTH: 23
<212> TYPE: DNA
<213> ORGANISM: Artificial
<220> FEATURE:
<223> OTHER INFORMATION: MDR-1 forward primer
<220> FEATURE:
<221> NAME/KEY: misc_feature
<222> LOCATION: (1)..(23)
<223> OTHER INFORMATION: MDR-1 forward primer

<400> SEQUENCE: 15
tggcaaagaa ataaagcgac tga                                             23

<210> SEQ ID NO 16
<211> LENGTH: 17
<212> TYPE: DNA
<213> ORGANISM: Artificial
<220> FEATURE:
<223> OTHER INFORMATION: MDR-1 reverse primer
<220> FEATURE:
<221> NAME/KEY: misc_feature
<222> LOCATION: (1)..(17)
<223> OTHER INFORMATION: MDR-1 reverse primer

<400> SEQUENCE: 16
caggatgggc tcctggg                                                    17

<210> SEQ ID NO 17
<211> LENGTH: 21
<212> TYPE: DNA
<213> ORGANISM: Artificial
<220> FEATURE:
<223> OTHER INFORMATION: MRP-1 forward primer
<220> FEATURE:
```

```
<221> NAME/KEY: misc_feature
<222> LOCATION: (1)..(21)
<223> OTHER INFORMATION: MRP-1 forward primer

<400> SEQUENCE: 17
gcttcctctt ggtgatattc g                                               21

<210> SEQ ID NO 18
<211> LENGTH: 19
<212> TYPE: DNA
<213> ORGANISM: Artificial
<220> FEATURE:
<223> OTHER INFORMATION: MRP-1 reverse primer
<220> FEATURE:
<221> NAME/KEY: misc_feature
<222> LOCATION: (1)..(19)
<223> OTHER INFORMATION: MRP-1 reverse primer

<400> SEQUENCE: 18
gcagttcaac gcatagtgg                                                  19

<210> SEQ ID NO 19
<211> LENGTH: 25
<212> TYPE: DNA
<213> ORGANISM: Artificial
<220> FEATURE:
<223> OTHER INFORMATION: ABCG2 forward primer
<220> FEATURE:
<221> NAME/KEY: misc_feature
<222> LOCATION: (1)..(25)
<223> OTHER INFORMATION: ABCG-2 forward primer

<400> SEQUENCE: 19
catgtactgg cgaagaatat ttggt                                           25

<210> SEQ ID NO 20
<211> LENGTH: 21
<212> TYPE: DNA
<213> ORGANISM: Artificial
<220> FEATURE:
<223> OTHER INFORMATION: ABCG2 reverse primer
<220> FEATURE:
<221> NAME/KEY: misc_feature
<222> LOCATION: (1)..(21)
<223> OTHER INFORMATION: ABCG2 reverse primer

<400> SEQUENCE: 20
cacgtgattc ttccacaagc c                                               21

<210> SEQ ID NO 21
<211> LENGTH: 21
<212> TYPE: DNA
<213> ORGANISM: Artificial
<220> FEATURE:
<223> OTHER INFORMATION: Bmil forward primer
<220> FEATURE:
<221> NAME/KEY: misc_feature
<222> LOCATION: (1)..(21)
<223> OTHER INFORMATION: Bmil forward primer

<400> SEQUENCE: 21
aaatgctgga gaactggaaa g                                               21

<210> SEQ ID NO 22
<211> LENGTH: 19
<212> TYPE: DNA
<213> ORGANISM: Artificial
<220> FEATURE:
<223> OTHER INFORMATION: Bmil reverse primer
<220> FEATURE:
```

```
<221> NAME/KEY: misc_feature
<222> LOCATION: (1)..(19)
<223> OTHER INFORMATION: Bmil reverse primer

<400> SEQUENCE: 22
ctgtggatga ggagactgc                                                    19

<210> SEQ ID NO 23
<211> LENGTH: 18
<212> TYPE: DNA
<213> ORGANISM: Artificial
<220> FEATURE:
<223> OTHER INFORMATION: Beta-catenin forward primer
<220> FEATURE:
<221> NAME/KEY: misc_feature
<222> LOCATION: (1)..(18)
<223> OTHER INFORMATION: Beta-catenin forward primer

<400> SEQUENCE: 23
ccagccgaca ccaagaag                                                     18

<210> SEQ ID NO 24
<211> LENGTH: 21
<212> TYPE: DNA
<213> ORGANISM: Artificial
<220> FEATURE:
<223> OTHER INFORMATION: Beta-catenin reverse primer
<220> FEATURE:
<221> NAME/KEY: misc_feature
<222> LOCATION: (1)..(21)
<223> OTHER INFORMATION: Beta-catenin reverse primer

<400> SEQUENCE: 24
cgaatcaatc caacagtagc c                                                 21

<210> SEQ ID NO 25
<211> LENGTH: 19
<212> TYPE: DNA
<213> ORGANISM: Artificial
<220> FEATURE:
<223> OTHER INFORMATION: PPARgamma2 forward primer
<220> FEATURE:
<221> NAME/KEY: misc_feature
<222> LOCATION: (1)..(19)
<223> OTHER INFORMATION: PPARgamma2 forward primer

<400> SEQUENCE: 25
caaaggcatg gggtcactt                                                    19

<210> SEQ ID NO 26
<211> LENGTH: 23
<212> TYPE: DNA
<213> ORGANISM: Artificial
<220> FEATURE:
<223> OTHER INFORMATION: PPARgamma2 reverse primer
<220> FEATURE:
<221> NAME/KEY: misc_feature
<222> LOCATION: (1)..(23)
<223> OTHER INFORMATION: PPARgamma2 reverse primer

<400> SEQUENCE: 26
ggacagcata tccctaactt tct                                               23

<210> SEQ ID NO 27
<211> LENGTH: 20
<212> TYPE: DNA
<213> ORGANISM: Artificial
<220> FEATURE:
<223> OTHER INFORMATION: Runx2 forward primer
<220> FEATURE:
```

```
<221> NAME/KEY: misc_feature
<222> LOCATION: (1)..(20)
<223> OTHER INFORMATION: Runx2 forward primer

<400> SEQUENCE: 27
tggcagcacg ctattaaatc                                                 20

<210> SEQ ID NO 28
<211> LENGTH: 20
<212> TYPE: DNA
<213> ORGANISM: Artificial
<220> FEATURE:
<223> OTHER INFORMATION: Runx2 reverse primer
<220> FEATURE:
<221> NAME/KEY: misc_feature
<222> LOCATION: (1)..(20)
<223> OTHER INFORMATION: Runx2 reverse primer

<400> SEQUENCE: 28
tctgccgcta gaattcaaaa                                                 20

<210> SEQ ID NO 29
<211> LENGTH: 24
<212> TYPE: DNA
<213> ORGANISM: Artificial
<220> FEATURE:
<223> OTHER INFORMATION: Osteopontin forward primer
<220> FEATURE:
<221> NAME/KEY: misc_feature
<222> LOCATION: (1)..(20)
<223> OTHER INFORMATION: Osteopontin forward primer

<400> SEQUENCE: 29
caaattcaaa gatatctttg tttc                                            24

<210> SEQ ID NO 30
<211> LENGTH: 20
<212> TYPE: DNA
<213> ORGANISM: Artificial
<220> FEATURE:
<223> OTHER INFORMATION: Osteopontin reverse primer
<220> FEATURE:
<221> NAME/KEY: misc_feature
<222> LOCATION: (1)..(20)
<223> OTHER INFORMATION: Osteopontin reverse primer

<400> SEQUENCE: 30
ccccactatc tgatgtctct                                                 20

<210> SEQ ID NO 31
<211> LENGTH: 20
<212> TYPE: DNA
<213> ORGANISM: Artificial
<220> FEATURE:
<223> OTHER INFORMATION: Oct-4 forward primer
<220> FEATURE:
<221> NAME/KEY: misc_feature
<222> LOCATION: (1)..(20)
<223> OTHER INFORMATION: Oct-4 forward primer

<400> SEQUENCE: 31
tgtggacctc aggttggact                                                 20

<210> SEQ ID NO 32
<211> LENGTH: 20
<212> TYPE: DNA
<213> ORGANISM: Artificial
<220> FEATURE:
<223> OTHER INFORMATION: Oct-4 reverse primer
<220> FEATURE:
```

```
<221> NAME/KEY: misc_feature
<222> LOCATION: (1)..(20)
<223> OTHER INFORMATION: Oct-4 reverse primer

<400> SEQUENCE: 32
cttctgcagg gctttcatgt                                                      20

<210> SEQ ID NO 33
<211> LENGTH: 20
<212> TYPE: DNA
<213> ORGANISM: Artificial
<220> FEATURE:
<223> OTHER INFORMATION: Nanog forward primer
<220> FEATURE:
<221> NAME/KEY: misc_feature
<222> LOCATION: (1)..(20)
<223> OTHER INFORMATION: Nanog forward primer

<400> SEQUENCE: 33
catcttctgc ttcctggcaa                                                      20

<210> SEQ ID NO 34
<211> LENGTH: 18
<212> TYPE: DNA
<213> ORGANISM: Artificial
<220> FEATURE:
<223> OTHER INFORMATION: nanog reverse primer
<220> FEATURE:
<221> NAME/KEY: misc_feature
<222> LOCATION: (1)..(18)
<223> OTHER INFORMATION: nanog reverse primer

<400> SEQUENCE: 34
ctgggaacgc ctcatcaa                                                        18

<210> SEQ ID NO 35
<211> LENGTH: 20
<212> TYPE: DNA
<213> ORGANISM: Artificial
<220> FEATURE:
<223> OTHER INFORMATION: integrin binding sialoprotein forward primer
<220> FEATURE:
<221> NAME/KEY: misc_feature
<222> LOCATION: (1)..(20)
<223> OTHER INFORMATION: integrin binding sialoprotein forward primer

<400> SEQUENCE: 35
ttccgcaaat gcttttgttt                                                      20

<210> SEQ ID NO 36
<211> LENGTH: 20
<212> TYPE: DNA
<213> ORGANISM: Artificial
<220> FEATURE:
<223> OTHER INFORMATION: integrin binding sialoprotein reverse primer
<220> FEATURE:
<221> NAME/KEY: misc_feature
<222> LOCATION: (1)..(20)
<223> OTHER INFORMATION: integrin binding sialoprotein reverse primer

<400> SEQUENCE: 36
gcgcagttag caatagcaca                                                      20

<210> SEQ ID NO 37
<211> LENGTH: 20
<212> TYPE: DNA
<213> ORGANISM: Artificial
<220> FEATURE:
<223> OTHER INFORMATION: GAPDH forward primer
<220> FEATURE:
```

```
<221> NAME/KEY: misc_feature
<222> LOCATION: (1)..(20)
<223> OTHER INFORMATION: GAPDH forward primer

<400> SEQUENCE: 37
agccaaaagg gtcatcatct                                               20

<210> SEQ ID NO 38
<211> LENGTH: 20
<212> TYPE: DNA
<213> ORGANISM: Artificial
<220> FEATURE:
<223> OTHER INFORMATION: GAPDH reverse primer
<220> FEATURE:
<221> NAME/KEY: misc_feature
<222> LOCATION: (1)..(20)
<223> OTHER INFORMATION: GAPDH reverse primer

<400> SEQUENCE: 38
ggggccatcc acagtcttct                                               20
```